United States Patent [19]
Prutchi

[11] Patent Number: 6,152,882
[45] Date of Patent: Nov. 28, 2000

[54] APPARATUS AND METHOD FOR CHRONIC MEASUREMENT OF MONOPHASIC ACTION POTENTIALS

[75] Inventor: David Prutchi, Lake Jackson, Tex.

[73] Assignee: Impulse Dynamics N.V., Curacao, Netherlands Antilles

[21] Appl. No.: 09/237,568

[22] Filed: Jan. 26, 1999

[51] Int. Cl.[7] ........................................................ A61N 5/04
[52] U.S. Cl. .............................................. 600/509; 607/9
[58] Field of Search .................................... 600/509, 554; 604/820, 821; 607/9

[56] References Cited

U.S. PATENT DOCUMENTS

| | | |
|---|---|---|
| 4,506,680 | 3/1985 | Stokes . |
| 4,651,716 | 3/1987 | Forester et al. . |
| 4,679,572 | 7/1987 | Baker . |
| 4,682,603 | 7/1987 | Franz et al. . |
| 4,690,155 | 9/1987 | Hess . |
| 4,955,382 | 9/1990 | Franz et al. . |
| 4,979,510 | 12/1990 | Franz et al. . |
| 5,022,396 | 6/1991 | Watanabe . |
| 5,156,149 | 10/1992 | Hudrlik . |
| 5,398,683 | 3/1995 | Edwards et al. . |

(List continued on next page.)

FOREIGN PATENT DOCUMENTS

| | | |
|---|---|---|
| WO 97/25098 | 7/1997 | WIPO . |
| WO 98/10828 | 7/1997 | WIPO . |
| WO 98/10829 | 7/1997 | WIPO . |
| WO 98/10832 | 7/1997 | WIPO . |
| WO 98/10831 | 3/1998 | WIPO . |
| WO 99/03533 | 1/1999 | WIPO . |

OTHER PUBLICATIONS

"Method and Theory of Monophasic Action Potential Recording" by Michael R. Franz, in Progress in Cardiovascular diseases, vol. XXXIII, No. 6, pp. 347–368, 1991.

"Basic Biophysical Characteristics of Fractally–Coated Electrodes", by Bolz et al. published in "Monophasic Action Potentials", Franz, Schmitt and Zenner eds., pp. 40–57, Springer–Verlag, Berlin, 1997.

Zrenner et al., "Recording of Monophasic Action Potentials with Fractally–Coated Electrodes—Experimental and Initial Clinical Results", published in "Monophasic Action Potentials", Franz, Schmitt and Zenner eds., pp. 58–68, Springer–Verlag, Berlin, 1997.

"A Model Analysis of Aftereffects of High–Intensity DC Stimulation on Action Potential of Ventricular Muscle" published by Sakuma et al., in IEEE Transactions on Biomedical Engineering, 45(2) pp. 258–267, 1998.

(List continued on next page.)

*Primary Examiner*—William E. Kamm
*Attorney, Agent, or Firm*—Cowan, Liebowitz & Latman, P.C.; William H. Dippert

[57] ABSTRACT

Apparatus and methods adapted for in vivo chronic measurement of cardiac monophasic action potentials (MAPs). The methods include, inter alia, providing a sensing electrode in contact with cardiac tissue and a reference electrode in proximity to the sensing electrode, intermittently inducing a transient localized depolarization or transient injury-like electrical currents in at least some of the cells of the cardiac tissue underlying or adjacent to the sensing electrode and measuring the potential difference between the sensing electrode and the reference electrode during at least part of the duration of the depolarization or injury-like currents. Other methods for inducing depolarization or injury-like currents in the tissue include, inter alia, localized membrane electroporation, localized electrostatic production of depolarization using voltage clamp to produce a signal representative of MAPs, localized tissue heating, localized application of ultrasound and localized irradiation with light. The apparatus and methods may also be applied for non-chronic measurement of cardiac monophasic action potentials and for measurement of monophasic action potentials from other non-cardiac excitable tissues.

96 Claims, 21 Drawing Sheets

U.S. PATENT DOCUMENTS

| | | |
|---|---|---|
| 5,425,363 | 6/1995 | Wang . |
| 5,482,052 | 1/1996 | Lerner ................................... 600/554 |
| 5,531,764 | 7/1996 | Adams et al. . |
| 5,556,421 | 9/1996 | Prutchi et al. . |
| 5,587,200 | 12/1996 | Lorentz et al. . |

OTHER PUBLICATIONS

Horner et al. titled "Electrode for Recording Direction of Activation, Conduction Velocity and Monophasic Action Potential of Myocardium", published in American Journal of Physiology, vol. 272 (Heart Circ. Physiol. 41), pp. H1917–H1927, 1997.

Koller, et al., titled "Relation Between Repolarization and Refractoriness During Programmed Electrical Stimulation in the Human Right Ventricle", published in Circulation 91(9), 2378–2384, 1995.

P. Fu and B.J. Bardakjian, titled "System Identification of Electrically Coupled Smooth Muscle Cells: The Passive Electrical Properties", published in IEEE Transactions on Biomedical Engineering, 38(11), pp. 1130–1140, 1991.

"Cellular Electrophysiological Effects of Hyperthermia on Isolated Guinea Pig Papillary Muscle; Implications for Catheter Ablation", published by Nath et al. in Circulation, vol. 88;4 part 1, pp. 1826–1831, 1993.

"Effect of Light on Calcium Transport in Bull Sperm Cells", published by R. Lubart et al., in Journal of Photochemical Photobiology B, vol. 14, No. 4, pp. 337–341, 1992.

"Action of Ultrasound on Strength of Contraction and Action Potential of the Papillary Muscle of the Rat Heart" published by S.I. Zakharov et al. in Byull. Eksp. Biol. Med., vol. 107, No. 4, pp. 423–426, 1989.

ated by the contraction. Cardiac muscle cells are electrically coupled enabling the flow of currents between them. Normally, a group of pacemaker cells located at the Sino-Atrial node (SA node) generates rhythmic electrical activity in the form of cell depolarization which then spreads rapidly to the rest of the heart, first to the atria and then to the ventricles. The currents flowing from the depolarized pacemaker cells to the neighboring electrically coupled cardiac muscle cells cause a depolarization therein. When the depolarization reaches a threshold value the muscle cells will generate an action potential which will then similarly spread to other coupled muscle cells.

APPARATUS AND METHOD FOR CHRONIC MEASUREMENT OF MONOPHASIC ACTION POTENTIALS

FIELD OF THE INVENTION

The present invention relates generally to the field of measurement of electrical signals of excitable tissues and more specifically to the field of chronic measurements of cardiac monophasic action potentials.

BACKGROUND OF THE INVENTION

Cardiac muscle is an excitable tissue composed, inter alia, of electrically excitable cardiac muscle cells. Typically, upon intrinsic or artificial supra-threshold electrical excitation cardiac muscle cells generate an action potential which triggers a delayed contraction. Cardiac muscle cells are electrically coupled enabling the flow of currents between them. Normally, a group of pacemaker cells located at the Sino-Atrial node (SA node) generates rhythmic electrical activity in the form of cell depolarization which then spreads rapidly to the rest of the heart, first to the atria and then to the ventricles. The currents flowing from the depolarized pacemaker cells to the neighboring electrically coupled cardiac muscle cells cause a depolarization therein. When the depolarization reaches a threshold value the muscle cells will generate an action potential which will then similarly spread to other coupled muscle cells.

Some of the currently held theories of the ionic basis of cardiac muscle cell action potentials and of the spread of electrical excitation and contraction within the cardiac muscle tissue are disclosed in detail in PCT application, International Publication Number WO 97/25098 to Ben-Haim et al., titled "ELECTRICAL MUSCLE CONTROLLER", incorporated herein by reference.

Reference is now made to FIG. 1 which is a schematic graph illustrating the various phases of a typical transmembrane action potential (TAP) recorded intracellularly in a ventricular cardiac muscle cell in-vitro using a prior art intracellular electrode. Typically, The cell membrane is impaled using a suitable glass microelectrode and the electrical potential difference between the intracellular milieu and an extracellular reference electrode is recorded as a function of time. The vertical axis represents the potential difference between the inside and the outside of the cell and the horizontal axis represents time. The curve labeled 1 represents the TAP signal. Typically, the potential difference across the resting cell membrane also known as the "resting potential" is approximately −90 millivolts (mV). The resting phase 2 lasts until the cell is activated. The minus sign indicates that the cell's inside is negatively charged with respect to the cell's outside. If the potential difference is changed to a value more positive than the resting potential, the cell membrane is the to be depolarized.

When an activation signal such as a localized depolarizing current flows into the cell, the cell membrane locally depolarizes. If the local depolarization reaches a certain threshold value (The action potential threshold), the entire cell membrane will rapidly depolarize within a few milliseconds to a value of approximately +20 mV. This phase is the rapid depolarization phase 4. The cell then repolarizes by about 10 mV in a first repolarization phase 5. The cell then slowly repolarizes by about 20 mV over a period of approximately 200–300 milliseconds, called the plateau phase 6. During the plateau phase 6, the muscle contraction occurs. At the end of the plateau phase 6, the cell continues to repolarize in a rapid repolarization phase 8. Finally, the cell again reaches the resting potential of the resting phase 2.

In the beating heart, this cycle repeats at a rate which is coupled to the intrinsic rate of activation of the cardiac pacemaker cells. During the plateau phase 6 and the rapid repolarization phase 8, the cardiac muscle cell enters a state during which the action potential threshold is modified. This state is called a refractory period. The refractory period includes an absolute refractory period in which the cell cannot be re-excited by a depolarizing stimulus, regardless of the level of the stimulus. The absolute refractory period is followed by a relative refractory period in which the stimulus level required to elicit an action potential is larger than the stimulus level required to elicit an action potential during the resting phase 2. It is possible to experimentally assess the duration of the absolute and relative refractory periods in vitro by injecting depolarizing current pulses through the intracellular electrode at different times during the plateau phase 6 and the fast repolarization phase 8 to determine at which time point re-excitation can occur and generate an action potential. The time point at which no stimulus however strong can evoke an action potential will indicate the transition point between the absolute and the relative refractory points.

The cardiac effective refractory period (ERP) is an empirically determined value, generally defined as the time interval between the time of initiation of activation of an excitable cardiac cell or group of cells and the time at which this cell or group of cells can be reactivated by an electrical stimulus of specific predetermined characteristics. The ERP value is therefore stimulus specific. For example, a first reactivating stimulating pulse having a specific set of shape and duration parameters and a specific pulse amplitude value will have a first empirically determined ERP value, while a second reactivating stimulating pulse having the same set of parameters and an amplitude higher than the amplitude of the first stimulating pulse may have a shorter empirically determined second ERP value.

It is noted that, the reference numbers of the various cardiac TAP phases of FIG. 1 are arbitrarily chosen and are not necessarily equivalent to the common terminology used in the medical literature for describing various phases of the cardiac TAP.

Some of the parameters of the TAP such as, inter alia, the action potential duration (APD), the action potential amplitude and the ERP may have significant clinical relevance in assessing various cardiac pathological conditions and the effects of various cardioactive drugs on cardiac tissue. Unfortunately, the technique of microelectrode intracellular recording is currently limited to isolated in-vitro preparations and cannot be clinically used in human patients.

However, other techniques are available which permit use of extracellularly recorded waveforms from the in situ beating heart of patients. Such extracellularly recorded waveforms may provide information related to some of the clinically relevant parameters of the cardiac action potential. One such method is the method of in-situ recording of cardiac monophasic action potentials (MAPs) from the beating heart of a patient.

The article titled "METHODS AND THEORY OF MONOPHASIC ACTION POTENTIAL RECORDING" by Michael R. Franz, in Progress In Cardiovascular diseases, Vol. XXXIII, No. 6. Pp. 347–368, 1991, incorporated herein by reference discloses apparatus and methods for recording of cardiac MAPs in excised tissue and isolated heart preparations in-vitro and in experimental animals and human patients in-vivo, and discusses theoretical aspects of MAP generation.

Cardiac MAPs may be measured by differential recording from two separate electrodes. The first electrode is usually placed in proximity to or in contact with intact cardiac tissue, such as the epicardium or the endocardium and serves as a reference electrode. The other electrode, sometimes referred to as the "probe electrode" is placed in contact with or in close proximity to the cardiac tissue at or near a site of a damaged portion of the tissue which serves as a localized site of injury currents or a site in which injury-like currents are locally induced. The injury-like currents may be generated, among others, by applying negative pressure to the endocardium or epicardium through a suction electrode or by gently pressing a special contact electrode against the endocardium or epicardium as disclosed in detail by Franz in the above referenced article.

Reference is now made to FIG. 2 which is a graph schematically illustrating the shape of a cardiac MAP signal recorded using a prior art contact electrode. The vertical axis represents the amplitude of the extracellularly recorded signal and the horizontal axis represents time. The curve labeled 11 represents the MAP signal. As seen from FIG. 2, the MAP signal is somewhat similar but not identical in shape to the TAP signal. The dashed line 14 represents the potential difference level recorded prior to contact of the sensing electrode with the tissue and is arbitrarily assigned a null value of zero millivolts. Typically, after the sensing electrode contacts the tissue, the recorded potential difference drops until it stabilizes at a new resting level which is the MAP baseline 12.

The precise tissue and cellular events underlying MAP generation are not fully understood. The current hypothesis based on available data, disclosed by Franz in the above referenced article, assumes that mechanical pressure or suction exerted against the myocardium depolarizes and inactivates the group of cells subjacent to the probe electrode, while leaving the adjacent cells largely unaffected.

Because these adjacent normal cells retain their ability to depolarize and repolarize actively, there is an electrical gradient between the depolarized and unexcitable cells subjacent to the electrode and the adjacent normal cells. During electrical diastole, this gradient results in a source current emerging from the normal cells and a sink current descending into the depolarized cells subjacent to the MAP sensing electrode. Under the volume conductor conditions provided by the surrounding tissue and blood pool, the sink current near the MAP sensing electrode results in a negative electrical field that is proportional to the strength of current flow, which again is proportional to the potential gradient between the subjacent depolarized and the adjacent non-depolarized cells. During electrical systole, the normal cells adjacent to the MAP sensing electrode undergo complete depolarization which overshoots the zero potential by some 30 mV whereas the already depolarized, and therefore refractory, cells subjacent to the MAP sensing electrode cannot further depolarize and maintain their potential at the former reference level. As a result, the former current sink reverses to a current source, producing an electrical field of opposite polarity. The strength and polarity of the boundary current and the resulting electrical field reflect the potential gradient between the reference potential in the depolarized and refractory cells subjacent to the electrode and voltage changes in the normal adjacent cells undergoing periodic depolarization and repolarization. According to this hypothesis, the MAP recording reflects the voltage time course of the normal cells that bound the surface of the volume of cells depolarized by the contact pressure.

As disclosed in detail in the article by Franz referenced hereinabove, it was shown by simultaneous recording of TAPs and MAPs from the same isolated rabbit cardiac tissue that there is a close agreement in the general shape and duration of the TAP and MAP signals. While not all the parameters of the MAP signals can be used to assess the underlying TAP parameters, some of the TAP parameters such as the APD, ERP and the repolarization time course may be obtained by measuring corresponding MAP parameter values.

A number of highly relevant clinical applications for the measurement of cardiac Monophasic Action Potentials (MAP) have been proposed. For example, MAP recordings have been used, inter alia, for assessing myocardial viability, monitoring myocardial drug absorption and the effects of anti-arrhythmic drugs on APD, evaluating of atrial and ventricular arrhythmia, determining the effects of heart rate and rhythm on APD, detecting myocardial ischemia, mapping infarcts and other clinical applications.

Methods and devices for the measurement of MAP signals are known in the art. U.S. Pat. No. 5,398,683 to Edwards et al. discloses a combination catheter for detecting monophasic action potential and for ablating surface tissue in an in vivo heart.

U.S. Pat. No. 4,682,603 to Franz et al. discloses a probe having a reference electrode and a probe electrode for recording monophasic action potentials from an in vivo heart.

U.S. Pat. Nos. 4,955,382 and 4,979,510 to Franz et al. disclose probes having a reference electrode, a probe electrode and including a stylet for recording monophasic action potentials from an in vivo heart.

U.S. Pat. No. 4,690,155 to Hess discloses a compartmentalized contact electrode catheter for recording monophasic action potential.

U.S. Pat. No. 5,425,363 to Wang discloses a plunge electrode for recording multiple intramyocardial monophasic action potentials.

U.S. Pat. No. 5,022,396 to Watanabe discloses a catheter for simultaneously measuring monophasic action potentials and endocardiac cavity pressure.

A disadvantage of the in vivo use of the suction electrode method in human patients is that it is typically limited to short duration recordings lasting only a few minutes. This time limitation is mainly due to the danger of causing tissue injury and traumatizing the cardiac muscle by the suction electrode but is also exacerbated by the increased risk to the patient caused by the necessity to use a complicated valve system for controlling the application of negative pressure to the suction electrode resulting in a danger of releasing air bubbles into the cardiovascular circulation which may cause arterial embolism.

The contact electrode method disclosed by Franz et al. in the above referenced Article and in U.S. Pat. Nos. 4,682,603, 4,955,382 and 4,979,510 hereinabove, enables extending the clinically useful MAP recording time to a period lasting up to a few hours. However, extending the MAP recording time beyond a few hours is problematic.

One major reason for the difficulty of extending the recording time beyond a few hours stems from the nature of the cellular processes occurring in the excitable tissue. The injury-like currents and depolarization induced in the group of cells subjacent the probe electrode by the electrode pressure eventually lead to the electrical uncoupling of the depolarized group of cells from adjacent, electrically active muscle cells. While the reasons for this electrical uncoupling are not fully understood, it is believed that the uncoupling is at least partly due to changes in the electrical conductivity properties of the gap-junctions coupling the cardiac muscle cells. Such gap-junction changes may be triggered by the continued presence of injury-like currents and/or the extended depolarization in the cells. Accumulation of Calcium ions and protons may play a role in these changes.

Irrespective of the exact underlying mechanisms, the electrical uncoupling between the cells subjacent the contact electrode and the rest of the cells gradually modifies the currents flowing between the depolarized tissue and the adjacent non-depolarized tissue, resulting in a continuing change of the recorded MAP signals. Typically, during extended recording periods, MAP amplitudes decrease and MAP shape changes over time. This inherent instability and the accompanying distortion of the MAP signal morphology precludes the recording of stable clinically interpretable MAP signals over periods longer than a few hours.

In addition to the problem of electrical uncoupling, when extended recordings of MAPs in vivo are attempted by chronically implanting MAP recording devices such as leads and catheters, other problems interfering with the extended stable recording of MAP signals may include the formation of scar tissue and/or connective tissue in the area of contact between the electrode tip and the tissue. Such tissue changes, referred to as "electrode encapsulation" hereinafter may also contribute to the changes in MAP signal characteristics over time by relieving the mechanical stresses caused by the electrode on the target cardiac tissue as well as by changing the electrical resistance of the tissue and the current path therethrough.

In an article titled "BASIC BIOPHYSICAL CHARACTERISTICS OF FRACTALLY-COATED ELECTRODES", by Bolz et al. published in "Monophasic Action Potentials", Franz, Schmitt and Zenner eds., pp. 40–57, Springer-Verlag, Berlin, 1997, the authors describe MAP-like signals recorded from near-term chronic implant of fractally-coated iridium electrodes. Signals resembling MAPs were recorded from such fractally-coated electrodes, 3 months after implantation. Unfortunately, MAP features are highly distorted in these recordings.

Furthermore, in a follow-up article by Zrenner et al., titled "RECORDING OF MONOPHASIC ACTION POTENTIALS WITH FRACTALLY-COATED ELECTRODES—EXPERIMENTAL AND INITIAL CLINICAL RESULTS", published in "Monophasic Action Potentials", Franz, Schmitt and Zenner eds., pp. 58–68, Springer-Verlag, Berlin, 1997, the authors report that in such chronic implants the mean MAP amplitude is decreased to less than 4 millivolts even in ventricular recordings, and that the morphology of the chronic MAP signal showed a depressed MAP plateau and a pronounced phase 3 repolarization resembling a T wave. The authors conclude that " . . . at present, the question of the feasibility of long-term recording and long-term stability of MAP remains unanswered".

Thus, unfortunately, current MAP recording techniques including, among others, use of plunge electrodes, suction electrodes, and pressure contact electrodes are not suitable for performing stable long-term chronic measurement of MAPs.

SUMMARY OF THE INVENTION

There is thus provided, in accordance with a preferred embodiment of the present invention, a method for measurement of monophasic action potentials from an excitable tissue including a plurality of cells. The method includes the steps of providing at least one sensing electrode adjacent to or in contact with a portion of the excitable tissue and at least one reference electrode in proximity to the at least one sensing electrode, intermittently inducing a transient depolarization in at least some of the cells adjacent the sensing electrode, the depolarization lasting for a first time interval, and measuring a signal representing the potential difference between the sensing electrode and the reference electrode within at least part of the first time interval.

Furthermore, in accordance with still another preferred embodiment of the present invention, the step of intermittently inducing includes applying an electrical current pulse through the at least one sensing electrode and the at least one reference electrode to at least some of the cells. The current pulse has a pulse duration, pulse shape, pulse magnitude and pulse polarity sufficient for causing electroporation of cell membranes of at least some of the cells.

Furthermore, in accordance with yet another preferred embodiment of the present invention, the method includes, prior to the step of intermittently inducing, the step of providing at least one electroporating electrode in contact with at least a portion of the excitable tissue adjacent to the sensing electrode. The step of intermittently inducing includes intermittently applying a current pulse through at least one electroporating electrode and at least one reference electrode to at least some of the cells. The current pulse has a pulse duration, pulse shape, pulse magnitude and pulse polarity sufficient for causing electroporation of cell membranes of the at least some of the cells.

Furthermore, in accordance with yet another preferred embodiment of the present invention, the step of intermittently inducing includes the step of intermittently increasing the temperature of at least part of the portion of the excitable tissue adjacent to or in contact with the sensing electrode to a temperature value sufficient to produce a depolarization and injury-like currents in at least part of the portion of the excitable tissue.

Furthermore, in accordance with another preferred embodiment of the present invention, the temperature value is in the range of 42°–48° C.

Furthermore, in accordance with yet another preferred embodiment of the present invention, the step of intermittently increasing the temperature includes the step of controllably heating the at least one sensing electrode by controllably passing an electrical current through a resistive element thermally coupled to the at least one sensing electrode.

Furthermore, in accordance with yet another preferred embodiment of the present invention, the step of intermittently increasing the temperature further includes the step of determining the temperature of the resistive element by measuring the resistance of the resistive element.

Furthermore, in accordance with yet another preferred embodiment of the present invention, the step of intermittently increasing the temperature includes the step of controllably heating the portion of the excitable tissue by controllably passing a high frequency alternating current therethrough.

Furthermore, in accordance with yet another preferred embodiment of the present invention, the high frequency alternating current is applied to the portion of the excitable tissue by the at least one sensing electrode and the method further includes prior to the step of measuring the step of filtering the signal for removing high frequency signal components from the signal.

Furthermore, in accordance with yet another preferred embodiment of the present invention, the high frequency alternating current is a radio frequency alternating current having a frequency in the range of 10–1200 KHz.

Furthermore, in accordance with yet another preferred embodiment of the present invention, the step of intermittently increasing the temperature includes the step of controllably heating at least part of the portion of excitable tissue by controllably irradiating at least part of the portion with microwaves having a frequency in the range of 0.7–100 GHz.

Furthermore, in accordance with yet another preferred embodiment of the present invention, the step of intermittently increasing the temperature includes the step of controllably irradiating at least part of the portion of the excitable tissue with light to heat the portion.

Furthermore, in accordance with yet another preferred embodiment of the present invention, the light is infra-red light.

Furthermore, in accordance with yet another preferred embodiment of the present invention, the step of intermittently inducing includes the step of intermittently applying to at least part of the portion of the excitable tissue adjacent to or in contact with the at least one sensing electrode mechanical waves having a frequency and intensity suitable for inducing a localized depolarization in at least some cells of the excitable tissue.

Furthermore, in accordance with yet another preferred embodiment of the present invention, the mechanical waves are selected from sonic waves and ultrasonic waves.

Furthermore, in accordance with yet another preferred embodiment of the present invention, the step of intermittently inducing includes the step of intermittently irradiating at least part of the portion of the excitable tissue adjacent to or in contact with the at least one sensing electrode with light having a frequency and intensity suitable for inducing a non-thermal localized depolarization in at least some cells of the excitable tissue.

Furthermore, in accordance with yet another preferred embodiment of the present invention, the step of intermittently inducing includes the step of intermittently applying to at least part of the portion of the excitable tissue adjacent to or in contact with the at least one sensing electrode at least one substance capable of inducing a depolarization in at least some of the cells of the excitable tissue.

Furthermore, in accordance with yet another preferred embodiment of the present invention, the substance is a physiological solution including KCl at a concentration sufficient to cause a depolarization of 5–20 millivolts in myocardial cells in situ.

There is also provided, in accordance with yet another preferred embodiment of the present invention, a method for measurement of a signal representing monophasic action potentials of an excitable tissue including a plurality of cells. The method includes the steps of providing a sensing electrode adjacent to or in contact with a portion of the excitable tissue and a reference electrode in proximity to the sensing electrode, intermittently inducing a transient depolarization and injury-like currents in at least some of the cells of the excitable tissue adjacent the sensing electrode by clamping the potential difference between the sensing electrode and the reference electrode at a value sufficient to electrostatically modify the electrical charge distribution across at least portions of the membranes of at least some of the cells, the clamping lasts for a first time interval, and measuring the clamping current required to maintain the value of the potential difference within at least part of the first time interval to obtain the signal.

There is also provided, in accordance with yet another preferred embodiment of the present invention, a method for measurement of signals representing monophasic action potentials from an excitable tissue including a plurality of cells, the method includes the steps of providing at least one sensing electrode adjacent to or in contact with a portion of the excitable tissue and at least one reference electrode in proximity to the sensing electrode, intermittently inducing a depolarization and injury-like currents in at least some of the cells of the excitable tissue adjacent at least one sensing electrode by clamping the potential difference between the sensing electrode and the reference electrode at a value sufficient to electrostatically modify the electrical charge distribution across at least portions of the membranes of at least some of the cells, the clamping lasts for a first time interval, and measuring the clamping current required to maintain the value of the potential difference within at least part of the first time interval to obtain at least one of the signals.

There is further provided, in accordance with yet another preferred embodiment of the present invention, a method for measurement of signals representing monophasic action potentials from an excitable tissue, the method includes the steps of providing at least one sensing electrode adjacent to or in contact with a portion of the excitable tissue and at least one reference electrode in proximity to the at least one sensing electrode, clamping the potential difference between the at least one sensing electrode and the at least one reference electrode at a first value, measuring the clamping current required to maintain the first value of the potential difference to obtain biphasic or polyphasic signals representing biphasic or polyphasic action potentials in the excitable tissue, increasing the potential difference to a second value sufficient to obtain substantially monophasic signals representing the monophasic action potentials, maintaining the second value for a time interval sufficient for measuring at least one of the substantially monophasic signals, and measuring the clamping current required to maintain the second value of the potential difference to obtain at least one of the substantially monophasic signals.

Furthermore, in accordance with another preferred embodiment of the present invention, the step of increasing includes gradually increasing the potential difference to a second value sufficient to obtain substantially monophasic signals representing the monophasic action potentials.

There is also provided, in accordance with yet another preferred embodiment of the present invention, apparatus for measurement of monophasic action potentials from an excitable tissue including a plurality of cells, the apparatus includes at least one probe electrode placeable adjacent to or in contact with a portion of the excitable tissue, at least one reference electrode placeable proximate the at least one probe electrode, an electroporating unit electrically connected to at least one probe electrode and at least one reference electrode for controllably applying to at least some of the cells subjacent the at least one probe electrode electrical current pulses suitable for causing electroporation of cell membranes of at least some of the cells, and an amplifier unit electrically connected to the at least one probe electrode and to the at least one reference electrode for providing an output signal representing the potential difference between the probe electrode and the reference electrode.

Furthermore, in accordance with another preferred embodiment of the present invention, the apparatus further includes a sensing unit electrically connected to the at least one probe electrode and to the at least one reference electrode for receiving the output signal of the amplifier and for generating a trigger signal representing the detection of a monophasic action potential in the output signal.

Furthermore, in accordance with another preferred embodiment of the present invention, the apparatus further includes an analog to digital converter for digitizing the output signal of the amplifier to provide a digitized signal, and a processing unit connected to the analog to digital converter and to the electroporating unit for controlling the activation of the electroporating unit and for processing the digitized signal to provide data representing at least one of the monophasic action potentials.

Furthermore, in accordance with another preferred embodiment of the present invention, the apparatus further includes a telemetry unit in communication with the processing unit for wirelessly transmitting the data.

Furthermore, in accordance with another preferred embodiment of the present invention, the telemetry unit is capable of wirelessly receiving signals for externally controlling the apparatus.

Furthermore, in accordance with another preferred embodiment of the present invention, the telemetry unit is capable of wirelessly receiving signals for reprogramming the processing unit.

Furthermore, in accordance with another preferred embodiment of the present invention, the at least one probe electrode and the at least one reference electrode are disposed within an implantable lead or catheter-like device disposed within a cardiac chamber.

Furthermore, in accordance with another preferred embodiment of the present invention, the excitable tissue is myocardial tissue of a heart and the apparatus further includes a pacing device electrically connected to the at least one probe electrode for in-vivo pacing of the heart.

There is also provided, in accordance with yet another preferred embodiment of the present invention, apparatus for measurement of monophasic action potentials from an excitable tissue including a plurality of cells. The apparatus includes at least one sensing electrode placeable adjacent to or in contact with a portion of the excitable tissue for sensing the potential of the portion, at least one reference electrode placeable proximate the at least one sensing electrode for sensing a reference potential, at least one electroporating electrode adjacent to the sensing electrode, the at least one electroporating electrode is placeable adjacent the portion of the excitable tissue or in contact with a part thereof, and an electroporating unit electrically connected to the at least one electroporating electrode for controllably applying to at least some of the cells adjacent the at least one electroporating electrode electrical current pulses suitable for causing electroporation of cell membranes of at least some of the cells.

There is also provided, in accordance with yet another preferred embodiment of the present invention, apparatus for measurement of monophasic action potentials from an excitable tissue including a plurality of cells. The apparatus includes a probe electrode placeable adjacent to or in contact with a portion of the excitable tissue, a reference electrode disposed proximate the probe electrode, and a voltage clamp unit electrically connected to the probe electrode and to the reference electrode for intermittently clamping the potential difference between the probe electrode and the reference electrode at a value sufficient to electrostatically modify the electrical charge distribution across at least portions of the membranes of at least some of the cells to generate injury-like currents in at least some of the cells adjacent the probe electrode, and for providing a signal representing the clamping current required to maintain the value of the potential difference. The signal includes at least one of the monophasic action potentials.

Furthermore, in accordance with another preferred embodiment of the present invention, the apparatus further includes a sensing unit electrically connected to the at least one probe electrode and to the at least one reference electrode for receiving the output signal of the voltage clamp unit and for generating a trigger signal representing the detection of a monophasic action potential in the output signal.

Furthermore, in accordance with another preferred embodiment of the present invention, the apparatus further includes an analog to digital converter for digitizing the output signal of the voltage clamp unit to provide a digitized signal, and a processing unit connected to the analog to digital converter and to the voltage clamp unit for controlling the activation of the voltage clamp unit and for processing the digitized signal to provide data representing at least one of the monophasic action potentials.

Furthermore, in accordance with another preferred embodiment of the present invention, the apparatus further includes a telemetry unit in communication with the processing unit for wirelessly transmitting the data.

Furthermore, in accordance with another preferred embodiment of the present invention, the telemetry unit is capable of wirelessly receiving signals for externally controlling the apparatus.

Furthermore, in accordance with another preferred embodiment of the present invention, the telemetry unit is capable of wirelessly receiving signals for reprogramming the processing unit.

Furthermore, in accordance with another preferred embodiment of the present invention, the apparatus according to claim 48 wherein the at least one probe electrode and the at least one reference electrode are disposed within an implantable lead or catheter-like device disposed within a cardiac chamber.

Furthermore, in accordance with another preferred embodiment of the present invention, the excitable tissue is the myocardium of a heart and the apparatus further includes a pacing device electrically connected to the at least one probe electrode for in-vivo pacing of the heart.

There is also provided, in accordance with yet another preferred embodiment of the present invention, apparatus for measurement of monophasic action potentials from an excitable tissue including a plurality of cells. The apparatus includes at least one probe electrode placeable adjacent to or in contact with a portion of the excitable tissue, at least one reference electrode disposed proximate the at least one probe electrode, and a voltage clamping unit electrically connected to the at least one probe electrode and to the at least one reference electrode for intermittently clamping the potential difference between the at least one probe electrode and the at least one reference electrode at a value sufficient to electrostatically modify the electrical charge distribution across at least portions of the membranes of the at least some of the cells to induce a transient depolarization in at least some of the cells adjacent the at least one probe electrode, and for providing a signal representing the clamping current required to maintain the value of the potential difference. The signal includes at least one of the monophasic action potentials.

There is also provided, in accordance with yet another preferred embodiment of the present invention, apparatus for measurement of monophasic action potentials from an excitable tissue including a plurality of cells. The apparatus includes at least one sensing electrode placeable adjacent to or in contact with a portion of the excitable tissue, at least one reference electrode disposed proximate the at least one probe electrode, a controllable depolarizing unit for intermittently inducing a transient depolarization in at least some of the plurality of cells of the portion, and an amplifier unit electrically connected to the at least one sensing electrode and to the at least one reference electrode for providing an output signal representing the potential difference between the at least one probe electrode and the at least one reference electrode.

Furthermore, in accordance with another preferred embodiment of the present invention, the controllable depolarizing unit is a controllable heating device capable of controllably heating at least some of the plurality of cells of the portion to induce the transient depolarization.

Furthermore, in accordance with another preferred embodiment of the present invention, the heating device includes a resistive element thermally coupled to the at least one sensing electrode and a controllable current source electrically connected to the resistive element for controllably flowing electrical current through the resistive element to controllably heat the resistive element and the at least one sensing electrode.

Furthermore, in accordance with another preferred embodiment of the present invention, the heating device further includes a temperature control unit for determining the temperature of the resistive element by measuring the resistance of the resistive element and for controlling current flow through the resistive element based on the temperature.

Furthermore, in accordance with another preferred embodiment of the present invention, the heating device further includes a temperature sensor thermally coupled to the at least one sensing electrode, and a temperature control unit electrically connected to the temperature sensor, for determining the temperature of the at least one sensing electrode and for controlling current flow through the resistive element based on the temperature.

Furthermore, in accordance with another preferred embodiment of the present invention, the heating device includes a high frequency electromagnetic energy source coupled to the portion of the excitable tissue for heating the portion.

Furthermore, in accordance with another preferred embodiment of the present invention, the high frequency electromagnetic energy source includes a high frequency oscillator and a variable gain high frequency amplifier electrically connected to the oscillator, the high frequency amplifier is electrically coupled to the at least one sensing electrode by a capacitor for passing high frequency alternating electrical currents therethrough.

Furthermore, in accordance with another preferred embodiment of the present invention, the high frequency alternating electrical current is a radio frequency alternating current having a frequency in the range of 10–1200 KHz.

Furthermore, in accordance with another preferred embodiment of the present invention, the apparatus further includes a high frequency filter electrically connected to the at least one sensing electrode, the at least one reference electrode and the amplifier unit for filtering out high frequency signal components generated by the high frequency amplifier.

Furthermore, in accordance with another preferred embodiment of the present invention, the high frequency electromagnetic energy source is a microwave energy source coupled to the excitable tissue by a wave-guide and capable of producing microwave radiation having a frequency in the range of 0.7–100 GHz for controllably heating at least part of the portion.

Furthermore, in accordance with another preferred embodiment of the present invention, the heating device includes a controllable light source for controllably directing light onto at least part of the portion of the excitable tissue to heat the portion.

Furthermore, in accordance with another preferred embodiment of the present invention, at least some of the wavelengths of the light are absorbable by the portion to heat the portion.

Furthermore, in accordance with another preferred embodiment of the present invention, the light source includes a light emitting diode electrically connected to a control unit for controlling the emission of light by the light emitting diode.

Furthermore, in accordance with another preferred embodiment of the present invention, the light emitting diode is an infra-red light emitting diode.

Furthermore, in accordance with another preferred embodiment of the present invention, the light source is optically coupled to the portion by an optical fiber.

Furthermore, in accordance with another preferred embodiment of the present invention, the light source is selected from a coherent light source and an incoherent light source.

Furthermore, in accordance with another preferred embodiment of the present invention, the apparatus is an implantable apparatus and the light source is an implantable light source.

Furthermore, in accordance with another preferred embodiment of the present invention, the apparatus is implantable in a patient and the light source is an external light source disposed out of the patient.

Furthermore, in accordance with another preferred embodiment of the present invention, the apparatus is implantable in a patient and wherein the light source is an internal light source disposed within the implantable apparatus.

Furthermore, in accordance with another preferred embodiment of the present invention, the optical fiber is optically coupled to the portion by at least one optical element.

Furthermore, in accordance with another preferred embodiment of the present invention, the controllable depolarizing unit includes a source of mechanical waves.

Furthermore, in accordance with another preferred embodiment of the present invention, the source of mechanical waves is selected from a source of sonic waves and a source of ultrasonic waves.

Furthermore, in accordance with another preferred embodiment of the present invention, the source of mechanical waves includes an ultrasound frequency generator and an ultrasonic transducer electrically connected to the ultrasound frequency generator and mechanically coupled to the portion of the excitable tissue.

Furthermore, in accordance with another preferred embodiment of the present invention, the controllable depolarizing unit includes a light source for controllably directing light onto at least part of the portion of the excitable tissue to induce a non-thermal localized depolarization in the portion.

Furthermore, in accordance with another preferred embodiment of the present invention, at least some of the wavelengths of the light are absorbable by the excitable tissue to induce a non-thermal depolarization in at least part of the portion.

Furthermore, in accordance with another preferred embodiment of the present invention, the light source includes a light emitting diode electrically connected to a control unit for controlling the emission of light by the light emitting diode.

Furthermore, in accordance with another preferred embodiment of the present invention, the light source is optically coupled to the portion by an optical fiber.

Furthermore, in accordance with another preferred embodiment of the present invention, the light source is selected from a coherent light source and an incoherent light source.

Furthermore, in accordance with another preferred embodiment of the present invention, the apparatus is an implantable apparatus and the light source is an implantable light source.

Furthermore, in accordance with another preferred embodiment of the present invention, the apparatus is implantable in a patient and wherein the light source is an external light source disposed out of the patient.

Furthermore, in accordance with another preferred embodiment of the present invention, the optical fiber is optically coupled to the portion by at least one optical element.

Furthermore, in accordance with another preferred embodiment of the present invention, the controllable depolarizing unit includes a controlled release unit capable of releasing at least one substance capable of depolarizing the excitable tissue near at least part of the portion of the excitable tissue.

Furthermore, in accordance with another preferred embodiment of the present invention, the controlled release unit includes a reservoir for storing a fluid including the at least one substance and a hollow member having one end connected to the reservoir and a second end disposed near at least part of the portion for applying at least some of the fluid to the at least part of the portion.

Furthermore, in accordance with another preferred embodiment of the present invention, the controlled release unit further includes a controllable valve disposed at the second end of the hollow member for controlling the applying of the fluid from the second end.

Furthermore, in accordance with another preferred embodiment of the present invention, the controlled release unit further includes a controllable pump for assisting the applying of the fluid from the second end.

Furthermore, in accordance with another preferred embodiment of the present invention, the excitable tissue is an in-vivo heart, the cells are cardiac muscle cells and the monophasic action potentials are cardiac monophasic action potentials and wherein the fluid includes a physiological solution including a concentration of potassium chloride suitable for inducing a depolarization in the portion, the depolarization being sufficient for recording at least one of the cardiac monophasic action potentials.

Further, in accordance with another preferred embodiment of the present invention, the excitable tissue is cardiac muscle of an in-vivo heart of a patient and the plurality of cells includes cardiac muscle cells.

Finally, in accordance with another preferred embodiment of the present invention, the cardiac muscle is selected from endocardial muscle, epicardial muscle, mid-myocardial muscle and any combination thereof.

BRIEF DESCRIPTION OF THE DRAWINGS

The invention is herein described, by way of example only, with reference to the accompanying drawings, in which like components are designated by like reference numerals, wherein.

DETAILED DESCRIPTION OF THE INVENTION

Notation Used Throughout

Figure 1:
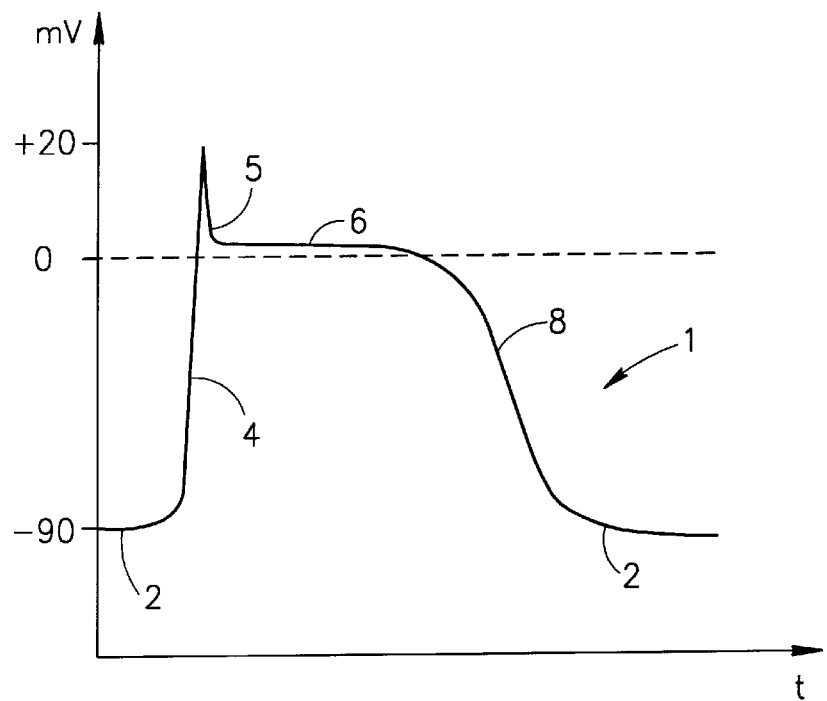
FIG. 1 is a schematic graph illustrating the various phases of a typical transmembrane action potential (TAP) recorded intracellularly in a ventricular cardiac muscle cell in-vitro using a prior art intracellular recording method.

The following notation is used throughout this document.

| Term | Definition |
| --- | --- |
| MAP | Monophasic Action Potential |
| ERP | Effective Refractory Period |
| APD | Action Potential Duration |
| HR | Heart Rate |
| ETC | Excitable tissue controller |
| IEGM | Intra-cardiac Electrogram |
| TAP | Trans-membrane Action Potential |
| VT | Ventricular Tachycardia |
| VF | Ventricular Fibrillation |

It is noted that the term MAPs as used throughout the present application is a broad term generally referring to extracellularly-recorded waveforms that reproduce the depolarization and repolarization time-course of TAPs.

While MAPs often appear as approximately monophasic signals, the term MAP as used throughout the present application is not intended to be limited to truly monophasic signals but also refers to signals having a biphasic or polyphasic shape as long as one of the components of the signal includes information representing at least one clinically useful TAP parameter. For example, under certain recording conditions, electrical potentials generated at a cardiac site such as an ischemic cardiac tissue region distal to the recording region may lead to a superimposing of an additional signal on the main monophasic signal resulting in a biphasic or polyphasic signal. Such signals are also regarded as included in the broad definition of the term MAP as long as they can be used to obtain a clinically useful parameter of the TAP, such as the plateau duration or the effective refractory period or any other clinically useful TAP parameter.

Additionally, the term MAP is also intended to include extracellularly recorded action potentials which have a biphasic shape having a signal part representing a hyperpolarizing after-potential more negative than the resting potential of the underlying TAP.

It is further noted that, the term "recording" is used throughout this application in a broad sense similar to it's accepted use in terms such as "intracellular recording". Thus, the term "recording" is broadly interpreted to include activities such as measuring and monitoring, and may also include but is not limited to actual recording on a recording medium such as a tape recorder or other analog or digital recording devices. For example, the recorded MAP signals may be displayed on an analog or digital oscilloscope screen for analysis, recorded on an analog or digital recording device for off-line analysis and may also be digitized and stored as digital data in a suitable memory device for on-line or off-line processing, analysis and display. All the above forms of data handling are implied by the term recording.

The contact electrodes known in the art of MAP recording must exert a continuous pressure on the cardiac tissue in order to evoke the injury-like currents and depolarization. It is probably the continuous presence of the injury-like currents and depolarization that eventually lead to the cellular electrical uncoupling disclosed hereinabove preventing long term stable chronic recording of MAPs.

The inventor of the present invention has noticed that it may be possible to perform stable chronic recording of MAPs by shortening the periods of induction of injury-like currents and depolarization in the tissue. Short periods of injury-like currents and depolarization may be intermittently induced in the cardiac tissue by different methods as disclosed in detail hereinafter. The duration of each period of induction of the injury-like currents and depolarization need be long enough to enable obtaining a number of MAP signals which is sufficient for obtaining clinically meaningful data. However, since the injury-like currents and depolarization are not permanently maintained in the tissue but are allowed to subside or are controllably terminated, the development of electrical tissue uncoupling is substantially prevented.

Various methods may be used for intermittently and reversibly inducing short periods of injury-like currents and depolarization in the cardiac tissue. Such inducing methods may include, inter alia, reversible membrane electroporation of cardiac muscle cells by current pulse application and electrostatic induction of local depolarization in cardiac cells. Other methods may also include non-destructive thermal induction of injury-like currents using a contact heating device, a laser heating device or a radio frequency (RF) heating device. Additional methods may also include the use of localized ultrasonic induction of injury-like currents and local depolarization in cardiac cells. The methods may further include the induction of light-induced local depolarization and injury-like currents by locally irradiating the tissue with of pulsed or continuous, coherent or non-coherent light radiation.

Finally, additional methods may include localized induction of injury-like currents and local depolarization in cardiac cells by locally and controllably releasing near the cardiac tissue substances capable of producing injury-like currents and depolarization in the tissue as disclosed in detail hereinbelow.

Electrical-Induction of Localized Myocardial Depolarization

Figure 3:
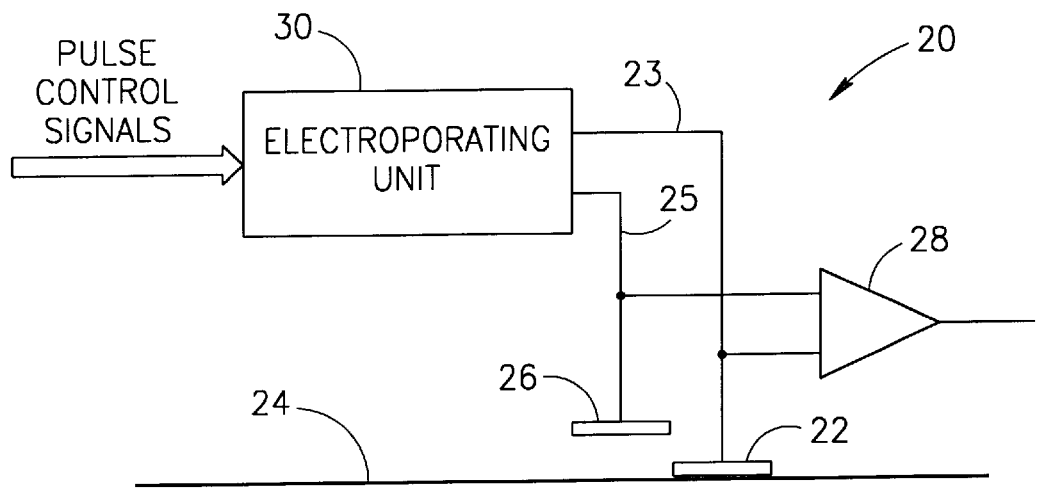
FIG. 3 is a schematic diagram illustrating apparatus for chronic recording of MAPs using a membrane electroporating unit, in accordance with a preferred embodiment of the present invention.

Reference is now made to FIG. 3 which is a schematic diagram illustrating apparatus for chronic measurement of cardiac MAPs using a membrane electroporating unit, in accordance with a preferred embodiment of the present invention. The MAP measuring apparatus 20 includes a probe electrode 20 which is placed in contact with or adjacent to a portion of the surface of an electrically excitable cardiac muscle tissue 24. The apparatus 20 further includes a reference electrode 26 which is positioned proximate the probe electrode 22. Preferably, the reference electrode 26 is in contact with an electrically passive cardiac tissue or with a fluid such as intra-cardiac blood or with interstitial fluid in the case of epicardial electrode placement, for minimizing the pick-up of electrical activity from an electrically active region unrelated to the active region subjacent the probe electrode 22. The probe electrode 22 and the reference electrode 26 are electrically connected to an amplifier 28. The output of the amplifier 28 represents the potential difference between the probe electrode 22 and the reference electrode 26.

The probe electrode 22 and the reference electrode 26 are also connected to the output terminals 23 and 25, respectively, of an electroporating unit 30. The electroporating unit 30 may be any suitable circuitry capable of controllably applying to the electrodes 22 and 26 electrical current pulses having a pulse duration, pulse shape, pulse polarity and pulse magnitude selected to impose on cardiac muscle cells subjacent the probe electrode 22 a potential sufficient to cause reversible dielectric breakdown of the cell membranes of some of these cells. The electroporating unit 30 receives control signals which may determine the timing of pulse application and the duration, amplitude and polarity of the current pulses which are applied to the tissue.

The dielectric breakdown causes the flow of a net ionic current into the cells, and depolarizes these cells. Typically, when the external field is large enough to produce a critical imposed potential of approximately 200 mV to 1V on the cells subjacent the probe electrode 22 membrane dielectric breakdown occurs as disclosed in detail in an article titled "A MODEL ANALYSIS OF AFTEREFFECTS OF HIGH-INTENSITY DC STIMULATION ON ACTION POTENTIAL OF VENTRICULAR MUSCLE" published by Sakuma et al., in IEEE Transactions on Biomedical Engineering, 45(2) pp. 258–267, 1998, incorporated herein by reference.

This dielectric breakdown phenomenon, also termed "electroporation" has a transient effect, since the membranes tend to gradually reseal after the cessation of the electroporating pulse, and the physiological ionic distribution across the membrane is restored with time by active transport mechanisms.

The transient depolarization of the cells under the recording electrode which is achieved through the electroporating pulses enables MAP signals to be recorded for several minutes before the excitability and electrical activity of the depolarized cells is restored.

When using the prior art contact electrode method disclosed hereinabove, electrode encapsulation adversely affects MAP signal characteristics over time by relieving the mechanical stresses caused by the electrode on the target cardiac tissue and possibly by changing the electrical resistance of the tissue and the current path therethrough. Thus, the pressure exerted on the tissue which is the main cause for the injury-like currents enabling MAP recording, gradually varies after implantation contributing to MAP signal distortion.

In the method of the present invention, after implantation, electrode encapsulation may still occur as disclosed hereinabove and electrical uncoupling of one or a few cell layers subjacent the electrode may also occur. However, membrane electroporation can still be induced in the viable cell layer or layers underlying the uncoupled layer(s) by applying suitable current pulses as disclosed hereinabove. The resulting induced currents and depolarization last for a limited period of time after which the electroporated cells are restored to their former condition, preventing the development of the electrical uncoupling phenomena.

The application of the electroporating pulses can be intermittently repeated at a rate which is sufficient for obtaining clinically useful MAP data without development of significant uncoupling phenomena.

Thus, replacing the constant mechanical pressure by the use of intermittent application of electroporating current pulses to induce localized injury-like currents, the chronic post-implantation distortion of MAP shape is substantially reduced or avoided.

It is noted that, the application of the electroporating current pulses to the tissue must be carefully controlled and timed with respect to the intrinsic or paced cardiac muscle activation cycle to prevent electroporation induced tissue excitation from undesirably interfering with the intrinsic or paced cardiac excitation cycle. The electroporating unit 30 of FIG. 3 is therefore triggered by a trigger signal applied thereto. The trigger signal may be generated manually, by a pacemaker controller, or by other suitable synchronizing circuits as is disclosed in detail hereinafter.

It is further noted that, while typically the electroporating current pulses are square current pulses, other current pulses may be used having other pulse shapes. Some non-limiting examples of current pulse shapes are half sine pulses, triangular pulses sawtooth shaped pulses, but other different pulse shapes may also be used. Furthermore, brief pulse trains of various shapes may also be used for electroporation. Additionally, symmetric and non-symmetric bipolar pulses may also be used for electroporation.

Figure 4:
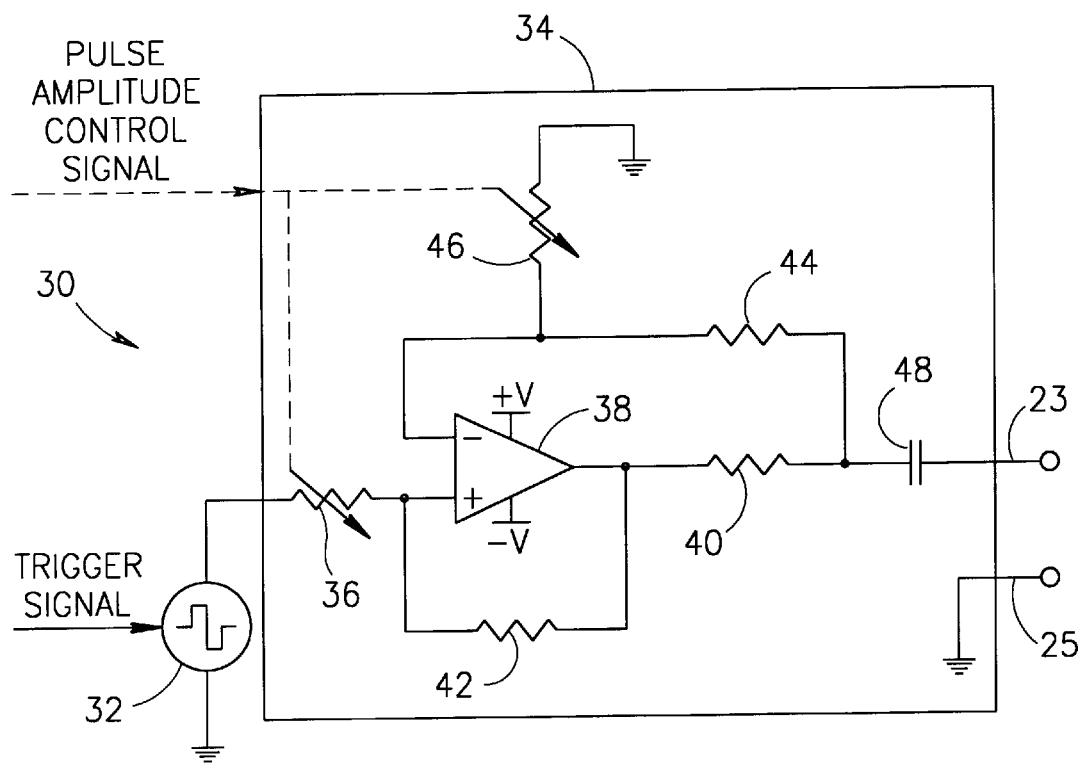
FIG. 4 is a schematic diagram illustrating details of the electroporation unit 30 of FIG. 3.

Reference is now made to FIG. 4 which is a schematic diagram illustrating details of the electroporating unit 30 of FIG. 3.

The electroporating unit 30 includes a pulse generator 32 and a voltage to current converter unit 34. The voltage to current converter 34 includes an operational amplifier 38. The pulse generator 32 is connected to the non-inverting terminal of the amplifier 38 through a control potentiometer 36. The output terminal of the amplifier 38 is connected to the non-inverting input terminal thereof through a feedback resistor 42. The output terminal of the amplifier 38 is further connected to a current sensing resistor 40. The resistor 40 is connected in series to a direct current (DC) blocking capacitor 48. The capacitor 48 is connected to the output terminal 23 of the electroporating unit 30. A feedback resistor 44 is connected between the current sensing resistor 40 and the inverting input terminal of the amplifier 38. A grounded control potentiometer 46 is connected to the inverting input terminal of the amplifier 38 and to the feedback resistor 44. The output terminal 25 of the electroporating unit 30 is grounded. The amplitude of the current pulse delivered between the output terminals 23 and 25 is controlled by a pulse amplitude control signal which adjusts the control potentiometers 36 and 46. The pulse amplitude control signal may be a manual mechanical adjustment of the control potentiometers 36 and 46 but may also be a control signal which is the output of a control unit (not shown) for manually or automatically controlling the pulse amplitude.

Figure 5:
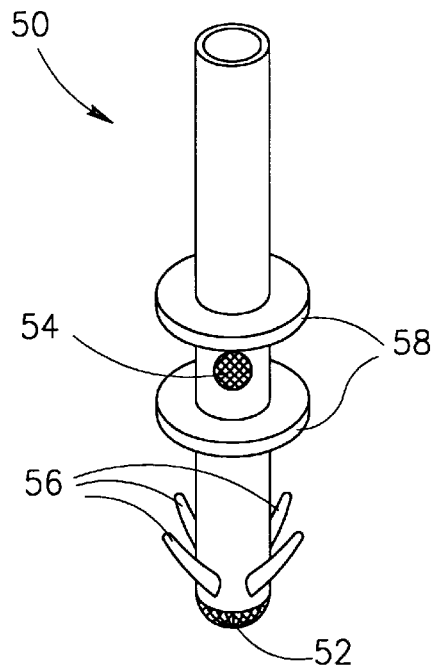
FIGS. 5–6 are schematic isometric views each illustrating a part of a different implantable probe connectable to the apparatus of FIGS. 3–4 and useful for intra-cardiac chronic MAP recording, in accordance with a preferred embodiment of the present invention.
Figure 6:
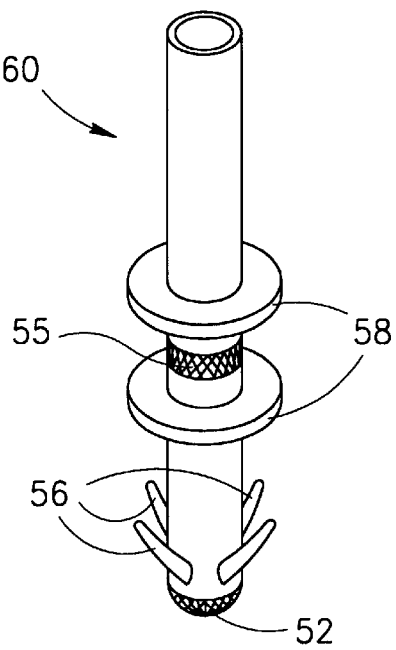

Reference is now made to FIGS. 5–6 which are schematic isometric views each illustrating a part of a different implantable probe connectable to the apparatus of FIGS. 3–4 and useful for intra-cardiac chronic MAP recording, in accordance with a preferred embodiment of the present invention. The probe of FIG. 5 is an implantable lead or catheter 50 which includes a probe electrode 52 attached at one end thereof and a dot-like reference electrode 54 having an exposed area of approximately 1–3 square millimeters attached to the catheter proximate the probe electrode 52.

The catheter 50 also includes a fixation mechanism including a plurality of tines 56 for anchoring the end of the catheter to cardiac tissue. The tines 56 are preferable to "active fixation" screws, since they cause most of the tissue reaction at a certain distance from the probe electrode 52. The catheter 50 also includes contact guards 58 for preventing the reference electrode 54 from closely approaching or contacting the cardiac tissue. The grommet-like contact guards 58 ensure that the reference electrode 54 is in contact with blood and inactive tissue (e.g. connective tissue) rather than with electrically-active myocardium so as not to contaminate the MAP signal. This prevents pick-up of unwanted signals from tissue regions other than the tissue subjacent the probe electrode 52. Typically, the distance between the probe electrode 52 and the reference electrode 54 is approximately 5 millimeters. However, other suitable distances in the range of a few millimeters may also be used. The area of the probe electrode is typically 2 to 8 square millimeters.

Preferably, the probe electrode 52 and the reference electrode 54 are low-impedance, low-polarization, low-reactivity electrodes such as the fractally coated iridium electrodes disclosed by Bolz et al. in the article referenced hereinabove. However, other types of suitable electrodes may be used. For example, the iridium oxide coated electrodes disclosed in U.S. Pat. No. 4,679,572 to Baker, or the titanium nitride coated electrodes disclosed in U.S. Pat. No. 5,587,200 to Lorentz et al. may also be used in the present invention.

FIG. 6 illustrates part of a catheter 60 which is similar to the catheter 50 of FIG. 5, except that the catheter 60 has a ring-like reference electrode 55 having a size of approximately 2–10 square millimeters surface instead of the dot-like reference electrode 54 of FIG. 5.

In accordance with one of the methods of the present invention, the catheter 50 is implanted intracardially using minimally invasive implantation methods known in the art. The probe electrode 52 is placed in contact with the ventricular or atrial cardiac muscle (not shown in FIG. 5). The probe electrode 52 and the reference electrode 54 are suitably connected to the electroporating unit 30 and to the amplifier 28 as illustrated in FIG. 3. Upon receiving an appropriate pulse control signal, the electroporating unit 30 delivers an electroporating current pulse to the tissue subjacent the probe electrode 52. After the electroporating pulse is terminated, the probe electrode 52 is used as a sensing electrode to record MAPs from the tissue. A number of MAPs are recorded while the cellular membranes are sufficiently electroporated for MAP recording. After the cessation of the electroporating pulse the membranes gradually reseal.

The brief electroporating pulses are applied intermittently to the tissue to prevent prolonged cell depolarization and injury-like currents from causing electrical uncoupling of the cell layers subjacent the probe electrode 52. In a non-limiting example, an electroporating pulse may be applied and MAPs recorded once every 24 hours to monitor the condition of a transplanted heart in a patient. However, electroporating pulse application and MAP recording may be performed periodically at a variety of desired frequencies or may be performed a-periodically on demand for other clinical applications as is disclosed hereinafter. Care should be taken to assure that the frequency and number of electroporations performed periodically and non-periodically will not exceed values which may lead to excessive electrical un-coupling of electrically coupled myocardial cells.

It is noted that the structural details of the catheters 50 and 60 and are not the subject of the present invention. Many types of MAP recording catheters and/or pacemaker leads known in the art may be used as the implantable catheter or lead of the chronic MAP recording apparatus of the present invention.

Figure 7:
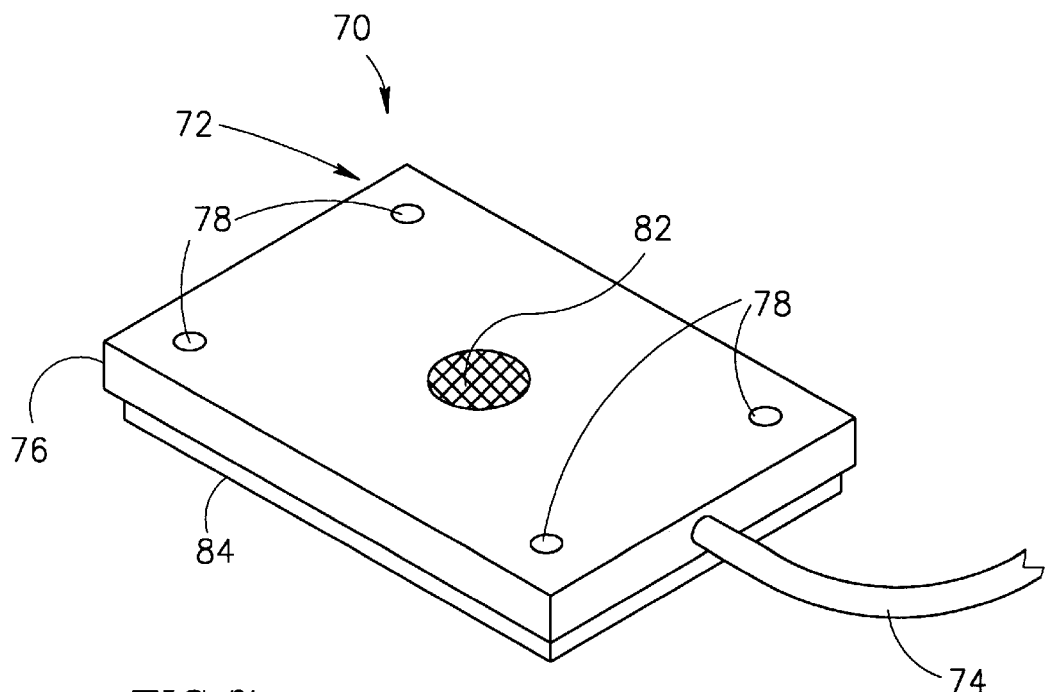
FIG. 7 is an isometric view of part of a probe connectable to the apparatus of FIGS. 3–4 and useful for chronic epicardial MAP recording, in accordance with a preferred embodiment of the present invention.

Reference is now made to FIG. 7 which is an isometric view of part of a probe 70 connectable to the apparatus of FIGS. 3–4 and useful for chronic epicardial MAP recording, in accordance with a preferred embodiment of the present invention.

The probe 70 includes an electrode assembly 72 and a lead 74 connected thereto. The electrode assembly 72 includes a member 76 made of a flexible electrically isolating material, such as a block of silicone elastomer or any other suitable electrically insulating biocompatible material. The member 76 has suture holes 78 passing therethrough which can be used for suturing the electrode assembly 72 onto the epicardium for long-term chronic MAP recordings.

The electrode assembly 72 includes a probe electrode 82 embedded within the member 76. The surface of the probe electrode 82 can be placed in contact with the epicardial tissue (not shown). The electrode assembly 72 further includes a reference electrode 84. The reference electrode 84 is a flat rectangular shaped electrode attached to a side of member 76 which is positioned opposite the side including the probe electrode 82.

Figure 8A:
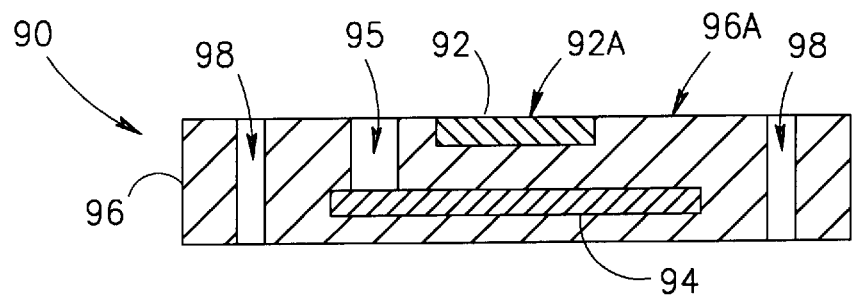
FIGS. 8A and 8B are schematic cross sectional views of two probes connectable to the apparatus of FIGS. 3–4 and useful for chronic epicardial MAP recording, in accordance with another preferred embodiment of the present invention.
Figure 8B:
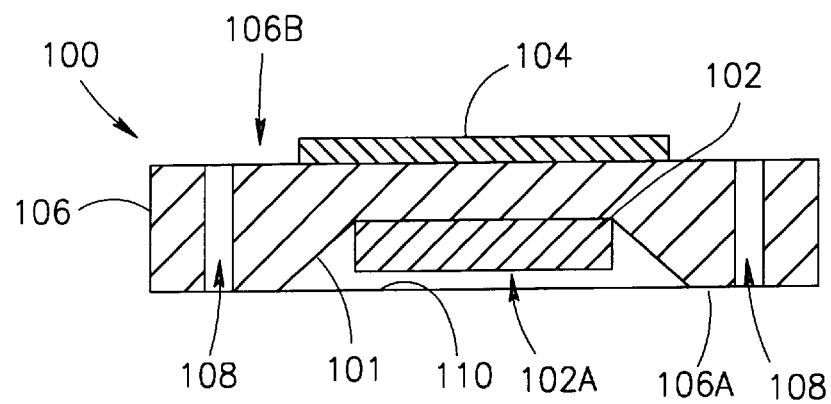

Reference is now made to FIGS. 8A and 8B which are schematic cross sectional views of two probes connectable to the apparatus of FIGS. 3–4 and useful for chronic epicardial MAP recording, in accordance with a preferred embodiment of the present invention.

The probe 90 of FIG. 8A includes a member 96 made of a flexible, electrically isolating material similar to the material of which the member 76 of FIG. 7 is made. The reference electrode 94 is embedded within the member 96 and is exposed to the interstitial fluid (not shown) through one or more small hollow passages 95 opening in the member 96. The probe electrode 92 is also embedded in the member 96 with it's surface 92A flush with the surface 96A of the member 96. For the sake of clarity of illustration, the lead and the electrically conducting wires connected to the reference electrode 94 and the probe electrode 92 are not shown.

Turning to FIG. 8B, the probe 100 includes a member 106 made of a flexible, electrically isolating material similar to the material of which the member 76 of FIG. 7 is made. The member 106 has a flat side 106B and a recessed side 106A. The reference electrode 104 is attached to the flat side 106A of the member 106 and is exposed to the interstitial fluid. The probe electrode 102 is attached within a recess 101 formed within the member 106. Suture holes 108 pass through the member 106. When the probe 100 is sutured onto the epicardium (suture not shown), the recessed side 106A contacts the epicardial surface 110 but the surface 102A of the probe electrode 102 is not in contact with the epicardial surface 110 but lies close thereto. The electroporating pulse parameters are adjusted to a level sufficient to enable electroporation of the membrane subjacent the probe electrode surface 102A. For the sake of clarity of illustration, the electrically conducting wires connected to the reference electrode 104 and the probe electrode 102 are not shown.

Figure 9:
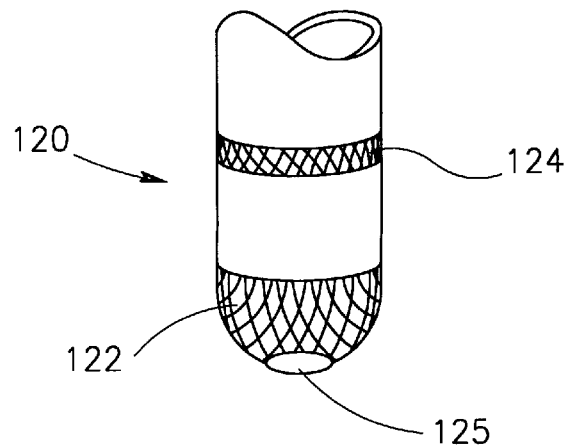
FIG. 9 is a schematic diagram of part of a drug infusing catheter useful for chronic MAP recording, in accordance with a preferred embodiment of the present invention.

Reference is now made to FIG. 9 which is a schematic diagram of part of a drug infusing catheter useful for chronic MAP recording, in accordance with a preferred embodiment of the present invention. The distal end of a catheter 120 includes a probe electrode 122 having drug dispensing capability and a ring-like reference electrode 124. The probe electrode 122 includes a drug elution path 125 which serves to dispense a desired drug onto the tissue subjacent the probe electrode 122. The structure and operation of drug dispensing electrodes is known in the art and is not the subject of the present invention. Preferably, the probe electrode 122 is of the steroid-eluting type disclosed in U.S. Pat. No. 4,506,680, to Stokes, titled "DRUG DISPENSING BODY IMPLANTABLE LEAD", incorporated herein by reference. The steroid eluted from the probe electrode 122 has the advantage of reducing the thickness of the layer of electrically decoupled cells and the amount of connective tissue formed between the probe electrode 122 and the electrically-viable, electrically-coupled myocardial cells. This reduction of tissue inflammatory processes and electrode encapsulation may improve the stability of the MAP recording and may reduce MAP signal distortion. The steroid drug may be a sodium salt of dexamethasone phosphate. However, other clinically acceptable steroid or non-steroid drugs which are found useful in chronic lead or catheter implantation and in MAP recording may be used.

Figure 10:
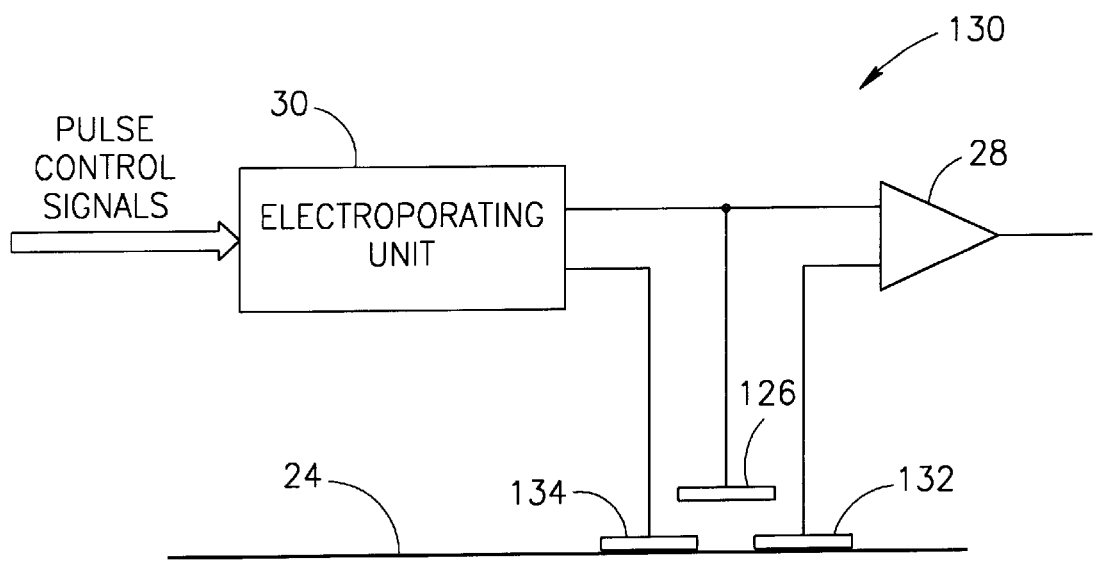
FIG. 10 is a schematic diagram of an apparatus for chronic measurement of cardiac MAPs having a sensing electrode and an electroporating electrode, in accordance with a preferred embodiment of the present invention.

Reference is now made to FIG. 10 which is a schematic diagram of an apparatus for chronic measurement of cardiac MAPs having a sensing electrode and an electroporating electrode, in accordance with a preferred embodiment of the present invention. The MAP measuring apparatus 130 includes an electroporating unit 30 and an amplifier 28. The apparatus 130 further includes a reference electrode 126, a sensing electrode 132 and an electroporating electrode 134. The reference electrode 126 and the electroporating electrode 134 are electrically connected to the output terminals of the electroporating unit 30 for controllably delivering electroporating current pulses to the cardiac muscle tissue 24 as disclosed in detail hereinabove. The sensing electrode 132 and the reference electrode 126 are connected to the amplifier 28 for measuring the potential difference therebetween and for recording MAP signals as disclosed hereinabove. The apparatus 130 of FIG. 10 has the advantage that use of a small-area electroporating electrode 134 enables better control of the volume of myocardium which is temporarily depolarized to generate injury-like currents.

Figure 11:
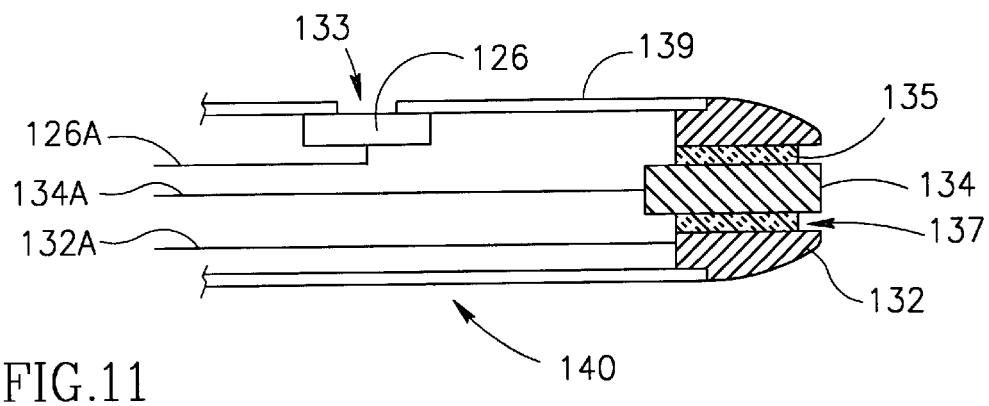
FIG. 11 is a schematic cross-sectional view illustrating part of a catheter having separate sensing and electroporating electrodes useful with the apparatus of FIG. 10.

Reference is now made to FIG. 11 which is a schematic cross-sectional view illustrating part of a catheter having separate sensing and electroporating electrodes useful with the apparatus of FIG. 10. The distal part of the catheter 140 includes a sensing electrode 132 which has a passage 137 therein. An electroporating electrode 134 is disposed within the passage 137 and is electrically isolated from the sensing electrode by an insulating member 135. The catheter 140 further includes a reference electrode 126 which is attached to the catheter body 139 and is exposed to the blood (not shown) through an opening 133 in the catheter body 139. Isolated electrically conducting wires 126A, 134A and 132A are electrically connected to the electrodes 126, 134 and 132, respectively, and are used for connecting the electrodes 126 and 134 to the electroporating unit 30 and the electrodes 126 and 132 to the amplifier 28 as illustrated in detail in FIG. 10. An advantage of using separate sensing and electroporating electrodes is that it reduces electrode polarization artifacts, since the electroporating currents are passed through the electroporating electrode 134 only and do not polarize the sensing electrode 132. Polarization artifacts occurring at the common reference electrode 126 can be reduced by increasing the effective surface area of the reference electrode 126. In a non-limiting example, the surface area of the reference electrode 126 can be increased by using a fractally coated iridium reference electrode as disclosed hereinabove. Electrode polarization reduction may also be achieved by using other types of suitable biocompatible high effective area electrode materials or electrode coating materials or by physically increasing the size of the reference electrode 126.

Figure 12:
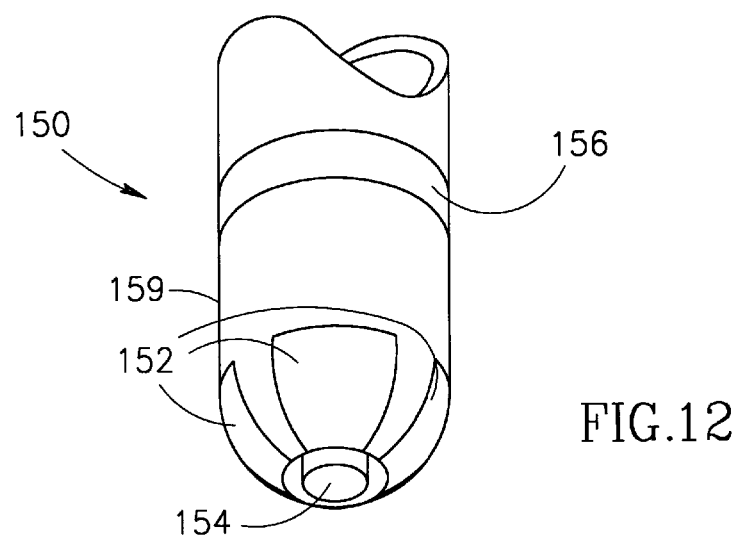
FIG. 12 is a schematic isometric view illustrating part of a catheter having a plurality of sensing electrodes and a common reference electrode, in accordance with a preferred embodiment of the present invention.

Reference is now made to FIG. 12 which is a schematic isometric view illustrating part of a catheter having a plurality of sensing electrodes and a common reference electrode, in accordance with a preferred embodiment of the present invention. The distal end of the catheter 150 includes a ring-like reference electrode 156 and a plurality of sensing electrodes 152. The sensing electrodes 152 are attached to the catheter wall 159 and are electrically isolated from each other. The sensing electrodes 152 surround an electroporating electrode 154 and are electrically isolated therefrom. The sensing electrodes 152 are equidistantly spaced from the electroporating electrode 154. However, other geometrical arrangements (not shown) of the sensing electrodes 152 relative to the electroporating electrode 154 are possible, depending on the specific application required.

Figure 13:
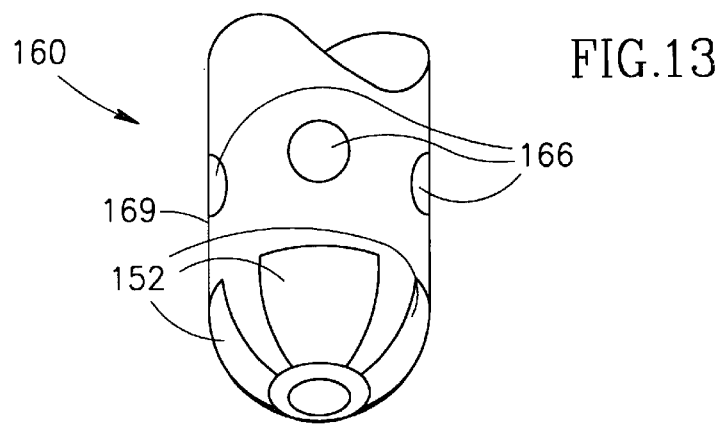
FIG. 13 is a schematic isometric view illustrating part of a catheter having a plurality of sensing electrodes and a plurality of reference electrodes, in accordance with another preferred embodiment of the present invention.

Reference is now made to FIG. 13 which is a schematic isometric view illustrating part of a catheter having a plurality of sensing electrodes and a plurality of reference electrodes, in accordance with another preferred embodiment of the present invention. The catheter 160 of FIG. 13 is similar to the catheter 150 of FIG. 12, except that the distal end of the catheter 160 includes a plurality of dot-like reference electrodes 166 instead of the ring-like reference electrode 156 of catheter 150. The reference electrodes 166 and the sensing electrodes 152 are arranged in pairs. The distance between the reference electrode 166 and the sensing electrode 152 of each pair is identical for all pairs.

It is noted that, while the plurality of the sensing electrodes 152 of the catheters 150 and 160 are shown as having a generally trapezoidal shape, and are geometrically symmetrically arranged relative to the electroporating electrode 154, many other sensing electrode shapes and geometrical arrangements are possible which are within the scope of the present invention. For example, the sensing electrodes may be a plurality of cylindrical structures (not shown) having annular cross-sectional areas and concentrically arranged around a central rod-like electroporating electrode (not shown). Alternatively, the sensing electrodes 152 may have rectangular or circular shapes or other desired shapes. The precise shapes, cross-sectional areas and geometrical arrangement of the plurality of sensing electrodes is determined, inter alia, by the specific application and by manufacturing considerations.

When using catheters having multiple sensing electrodes such as the catheters 150 and 160 of FIGS. 12 and 13, respectively, each of the sensing electrodes 152 may be used to record MAPs from the cardiac tissue underlying it by using a plurality of amplifiers (not shown), or a single amplifier coupled to appropriate multiplexing or switching circuits (not shown). The catheters 150 and 160 have an advantage, that during chronic long-term MAP recording if one sensing electrode 152 malfunctions or if the recorded MAP signals of one sensing electrode 152 develop an instability or exhibits distorted signal shape due to electrode encapsulation artifacts or due to any other reason, the remaining sensing electrodes may still be used for reliable MAP signal recording. This electrode redundancy may contribute to the reliability and fault tolerance of the apparatus and may increase the usability and lifetime of such chronically implanted catheters.

An additional advantage of catheters having a plurality of sensing electrodes is that they can also be used for simultaneous recording of MAP parameters and additional clinically relevant data such as the direction of activation of myocardial muscle and the conduction velocity of the myocardial propagating excitation wave adjacent the catheter contact region.

Figure 14:
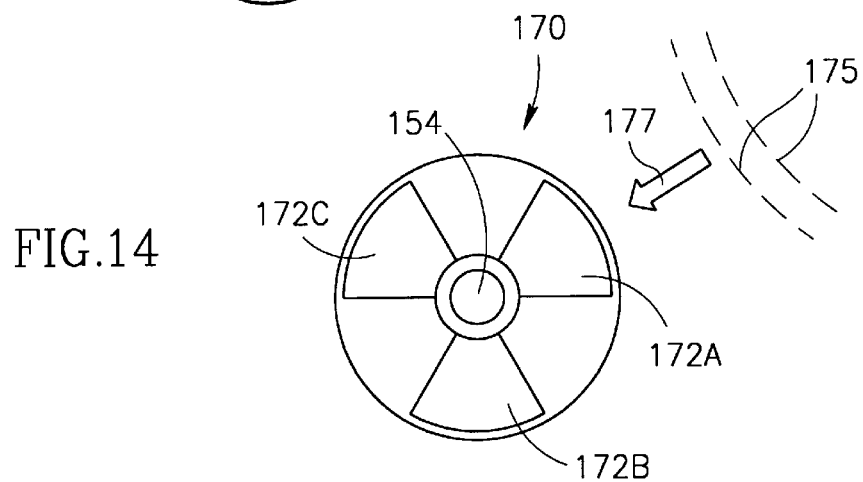
FIG. 14 is a schematic diagram illustrating the use of multi-electrode arrays in simultaneous determination of MAP parameters, direction of activation of myocardial muscle and conduction velocity of the activation wave in myocardial muscle, in accordance with a preferred embodiment of the present invention.

Reference is now made to FIG. 14 which is a schematic diagram illustrating the use of multi-electrode arrays in simultaneous determination of MAP parameters, direction of activation of myocardial muscle and conduction velocity of the activation wave in myocardial muscle, in accordance with a preferred embodiment of the present invention.

FIG. 14 illustrates the distal end of a catheter 170 as viewed from the surface of the myocardial tissue which is contacted thereby. The tissue surface is represented by the plane of the paper. The catheter 170 includes three sensing electrodes 172A, 172B and 172C, and an electroporating electrode 154. The reference electrode (preferably of the ring-like type) of the catheter 170 in not shown as it is disposed above the tissue surface.

A depolarization wave represented by the dashed lines labeled 175 is approaching the distal end of the catheter 170 in the general direction represented by the arrow labeled 177. The electroporating electrode 154 is used to deliver an electroporating pulse to the tissue for inducing injury-like currents as disclosed in detail hereinabove. The three sensing electrodes 172A, 172B and 172C are used to simultaneously record MAP signals as is disclosed in detail hereinafter. The depolarization wave, also referred to as the activation wave, first reaches the tissue region subjacent the sensing electrode 172A and only later reaches the tissue regions subjacent the sensing electrodes 172B and 172C. Due to the finite conduction velocity of the activation wave within the cardiac tissue, the MAP signals recorded by the sensing electrodes 172A and 172B are delayed relative to the MAP signal recorded by the sensing electrode 172C. The time of arrival of the activation wave at each of the electrodes 172A, 172B and 172C and the known distances and angles between the electrodes 172A, 172B and 172C may be used for calculating the direction of propagation of the activation wave relative to the electrodes 172A, 172B and 172C and the conduction velocity of the activation wave within the cardiac tissue.

Methods for calculating the conduction velocity and the direction of the activation wave using electrode arrays are known in the art and are not the subject matter of the present invention. For example, the conduction velocity and the direction of the activation wave may be calculated using the method disclosed by Horner et al. in an article titled "ELECTRODE FOR RECORDING DIRECTION OF ACTIVATION, CONDUCTION VELOCITY AND MONOPHASIC ACTION POTENTIAL OF MYOCARDIUM", published in American Journal of Physiology, Volume 272 (Heart Circ. Physiol. 41), pp. H1917–H1927, 1997, incorporated herein by reference. The above referenced method of Horner et al., uses a large suction electrode arrangement and is therefore limited to short term epicardial use. In contrast, the use of a chronically implantable electrode array catheter of the present invention, such as, but not limited to, the catheters 150, 160 and 170 of FIGS. 12, 13 and 14, respectively, may enable long term simultaneous recording and monitoring of the activation wave's direction and conduction velocity and of MAP signal parameters which may be clinically useful, inter alia, for predicting, diagnosing and or detecting reentry-linked tachyarrhythmias and other types of arrhythmias and for evaluation of anti-arrhythmic drug treatment in patients.

Figure 15:
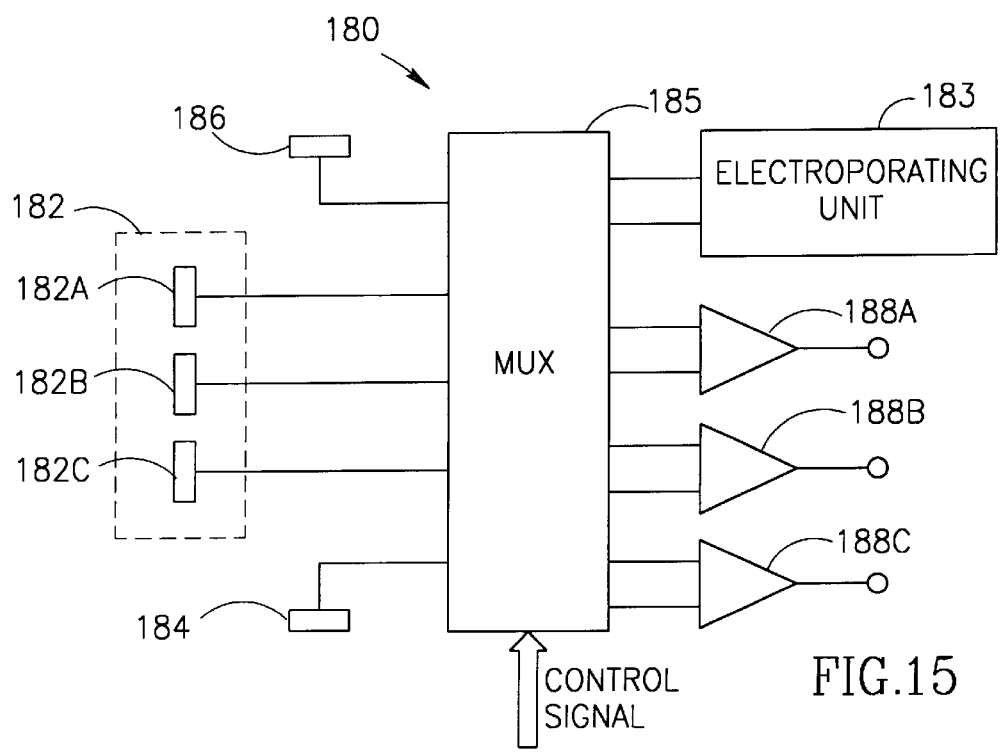
FIG. 15 is a schematic diagram of a MAP recording apparatus usable with catheters having a plurality of electrodes, in accordance with a preferred embodiment of the present invention.

Reference is now made to FIG. 15 which is a schematic diagram of MAP recording apparatus usable with catheters having a plurality of electrodes, in accordance with a preferred embodiment of the present invention. The apparatus 180 includes an electroporating unit 183 similar to the electroporating unit 30 of FIGS. 3 and 10. The apparatus 180 further includes a reference electrode 186, an electrode array 182 including three sensing electrodes 182A, 182B and 182C, and an electroporating electrode 184. The apparatus 180 further includes a multiplexer 185 and three amplifiers 188A, 188B and 188C. The amplifiers 188A, 188B and 188C, the reference electrode 186, the sensing electrodes 182A, 182B and 182C and the electroporating electrode 184 are electrically connected to the multiplexer 185. The apparatus 180 may be controllably switched by appropriate control signals between various different functional modes.

Figure 16:
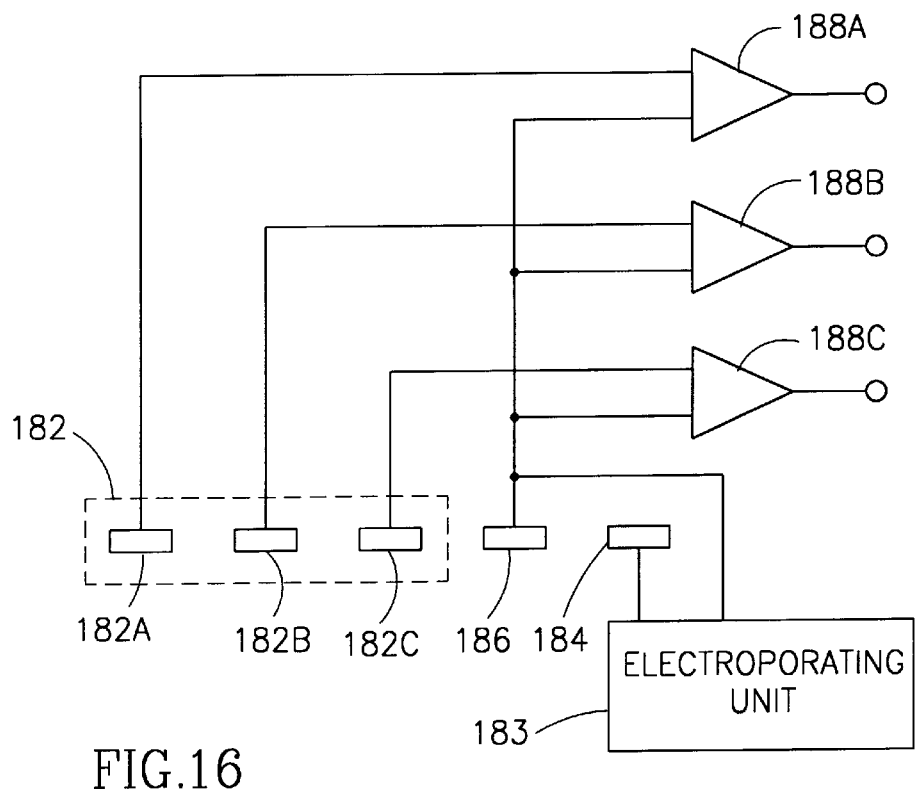
FIGS. 16 and 17 are schematic diagrams illustrating two functional modes of the apparatus 180 of FIG. 15.
Figure 17:
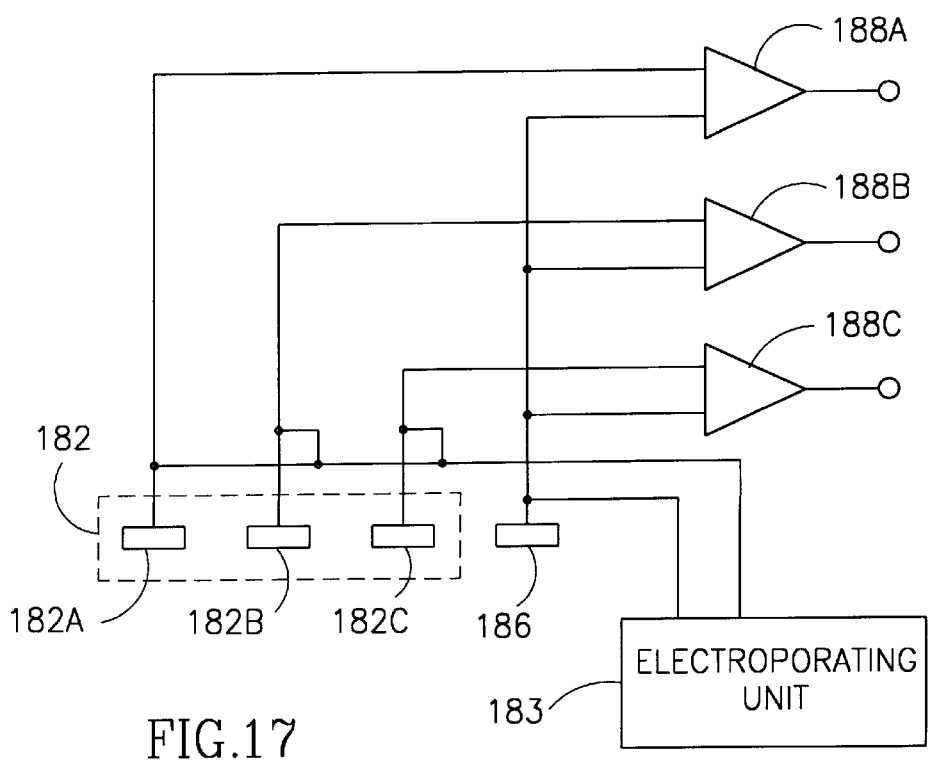

Reference is now made to FIGS. 16 and 17 which are schematic diagrams illustrating two different functional modes of the apparatus 180 of FIG. 15.

FIG. 16 illustrates a first functional mode which is useful for the determination of the velocity and direction of the cardiac activation wave. In the first functional mode, the sensing electrodes 182A, 182B and 182C are connected to amplifiers 188A, 188B and 188C, respectively. The reference electrode 186 is connected to the amplifiers 188A, 188B and 188C. The electroporating unit 183 is connected to the electroporating electrode 184 and to the reference electrode 186. All the connections are formed by the multiplexer 185 (not shown in FIG. 16). The first functional mode of FIG. 16 allows the use of the electrode array 182 of the apparatus 180 for determining the velocity and direction of the cardiac activation wave as disclosed in detail hereinabove.

FIG. 17 illustrates a second functional mode which is useful for recording MAP signals simultaneously from all the sensing electrodes of the electrode array 182. In the second functional mode, the sensing electrodes 182A, 182B and 182C are connected to amplifiers 188A, 188B and 188C, respectively. The reference electrode 186 is connected to all the amplifiers 188A, 188B and 188C and to the electroporating unit 183. The electroporating unit 183 is also connected to the sensing electrodes 182A, 182B and 182C. All the connections are formed by the multiplexer 185 (not shown in FIG. 17).

In the second functional mode, the electroporating electrode 184 (not shown in FIG. 17) is not used for tissue electroporation. The electroporating unit 183 simultaneously passes electroporating current pulses through all three sensing electrodes 182A, 182B and 182C. Thus, in the second functional mode, the sensing electrodes 182A, 182B and 182C operate as electroporating and sensing probe electrodes and MAP signals are recorded at the output of the amplifiers 188A, 188B and 188C. This mode may be used, inter alia, in cases where the electroporating electrode 184 malfunctions. For example, if scar tissue formation or electrode encapsulation selectively affects the current passing capability of the electroporating electrode 184, one or more of the sensing electrodes 182A, 182B and 182C, may still be used for electroporation and sensing by suitably controlling the multiplexer 185 (FIG. 15).

It is noted that, the apparatus 180 may be operated in additional functional modes (not shown) which are different from the first and second functional modes disclosed hereinabove. For example, a single sensing electrode selected from the sensing electrode array 182 may be connected to one amplifier selected from the three amplifiers 188A, 188B and 188C. This selected electrode may then be used for sensing MAPs, while the electroporating electrode 184 is used for electroporation. Alternatively, the multiplexer 185 may be configured to use a single electrode selected from the electrodes 182A, 182B, 182C and 184 for both electroporating and sensing. Similarly, other functional modes are possible using different combinations and permutations of pairs of electrodes selected from the electrode array 182 and used for sensing, or for electroporating and sensing as disclosed hereinabove.

One advantage of the plurality of functional modes is the increased electrode redundancy of the apparatus 180. The apparatus 180 may be reconfigured by application of the appropriate control signals to the multiplexer 185 to overcome malfunctioning of one or two of the amplifiers 188A, 188B and 188C, or malfunctioning or instability of one or more of the electrodes 182A, 182B, 182C and 184.

Another additional configuration (not shown) of the apparatus 180 of FIG. 15 involves the connecting of two of the electrodes 182A, 182B, 182C of the electrode array 182 to the electroporating unit 183 for tissue electroporation, and the connecting of the third remaining electrode of the electrode array 182 and the reference electrode 186 to one of the amplifiers 188A, 188B and 188C for MAP sensing. This configuration has the advantage of reducing electrode polarization artifacts.

It is noted that, while the preferred embodiments disclosed hereinabove include endocardial and epicardial surface contacting leads and/or catheters suitable for intracardiac and epicardial chronic recording of MAPs, other embodiments of the present invention may use leads having plunge electrodes suitable for recording MAPs from mid-myocardial cells. For example, the plunge electrode disclosed in U.S. Pat. No. 5,425,363 to Wang, incorporated herein by reference, may be modified to adapt it for use in chronic MAP recording. Over the extended time interval required for chronic MAP measurements, the plunge electrode disclosed by Wang may be dislodged from the myocardium or moved therewithin by the repetitive myocardial contractions. The plunge electrode disclosed by Wang may have to be adapted by adding an anchoring device (not shown) thereto. Such an anchoring device may be a screw type device (not shown) surrounding the plunge electrode, tines (not shown) suitably positioned and spaced apart from the plunge electrode tip, or any other suitable anchoring device capable of anchoring the plunge electrode to the myocardium after the plunge electrode has been pushed into the myocardium to bring the recording electrodes thereof into a position enabling the recording of MAPs from mid-myocardial tissue.

It is further noted that, the modified plunge electrodes disclosed hereinabove may also be adapted for recording any desired combination of epicardial, endocardial and mid-myocardial MAPS by suitably designing the recording electrode to enable multiple recordings from desired combinations of endocardial, epicardial and mid-myocardial sites.

Figure 18:
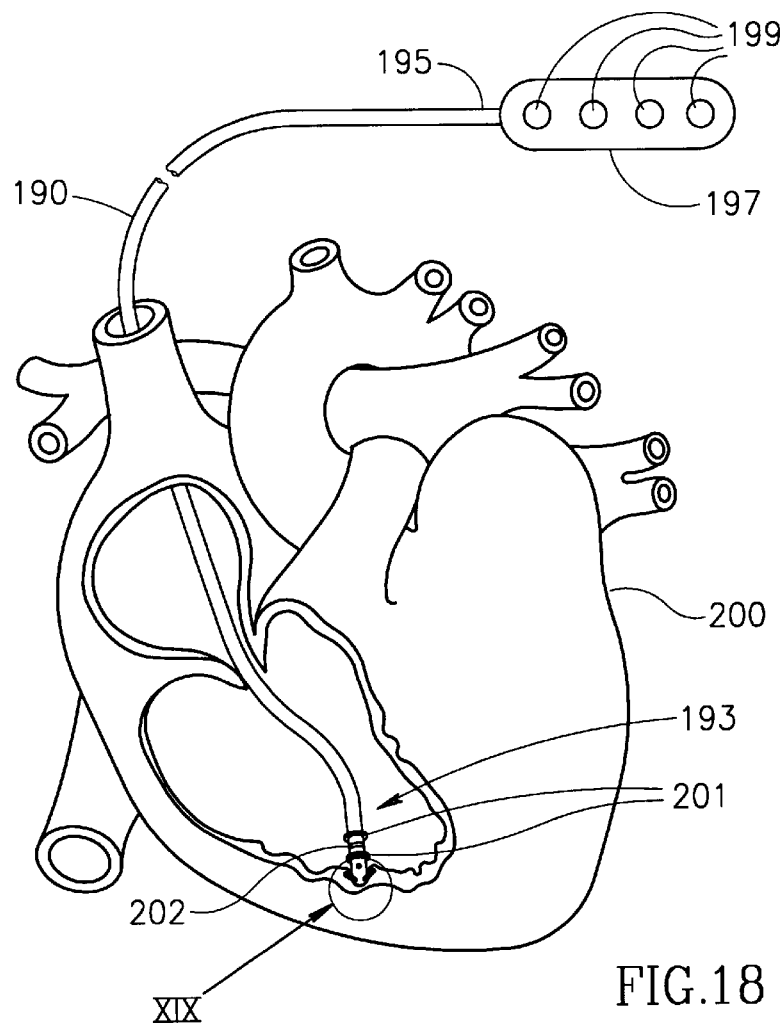
FIG. 18 is a schematic diagram illustrating an implantable pacing lead for minimally invasive heart transplant monitoring, in accordance with a preferred embodiment of the present invention.
Figure 19:
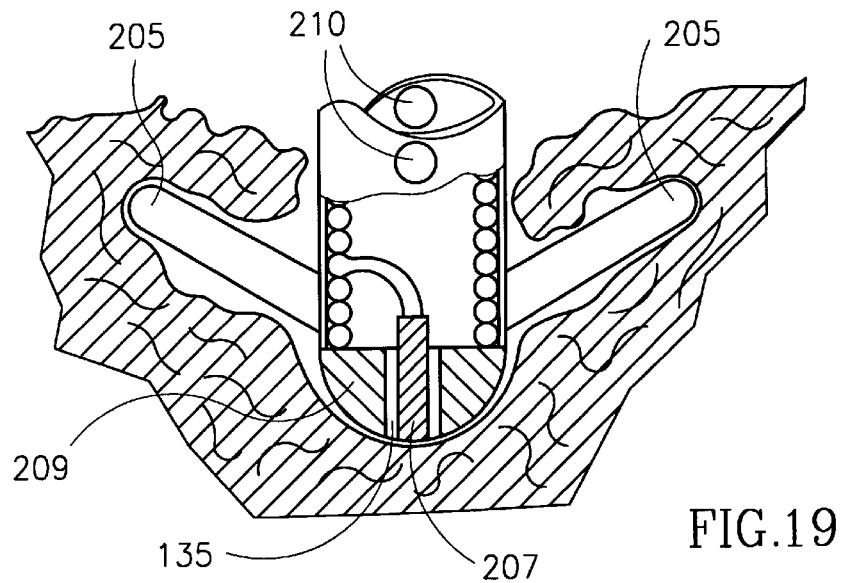
FIG. 19 is a schematic, part isometric part cross-sectional view illustrating part of the lead of FIG. 18 in detail.

Reference is now made to FIGS. 18 and 19. FIG. 18 is a schematic diagram illustrating an implantable pacing lead for minimally invasive heart transplant monitoring, in accordance with a preferred embodiment of the present invention. FIG. 19 is a schematic part isometric part cross-sectional view illustrating in detail the part of the lead of FIG. 18 and the part of the cardiac region within the circle labeled XIX of FIG. 18.

FIG. 18 illustrates a lead 190 which is implanted in a transplanted heart 200. The distal portion 193 of the lead 190 is inserted into the right ventricle of the heart 200 and contacts the apical ventricular end of the right ventricle. The proximal end 195 of the lead 190 is connected to a transcutaneous electrical access port 197. The access port 197 includes four electrically conducting contacts 199. The lead 190 includes two contact guards 201, a reference electrode 202 and a plurality of tines 205 for fixating the distal portion 193 of the lead 190 to the cardiac tissue. The lead 190 also includes an electroporating electrode 207 (FIG. 19) which is electrically connected to one of the contacts 199, a sensing electrode 209 (FIG. 19) which is electrically connected to another of the contacts 199, the reference electrode 202 (FIG. 18) which which is electrically connected to a third of the contacts 199 and two pacing electrodes 210 (FIG. 19) connected to a fourth one of the contacts 199.

Figure 20:
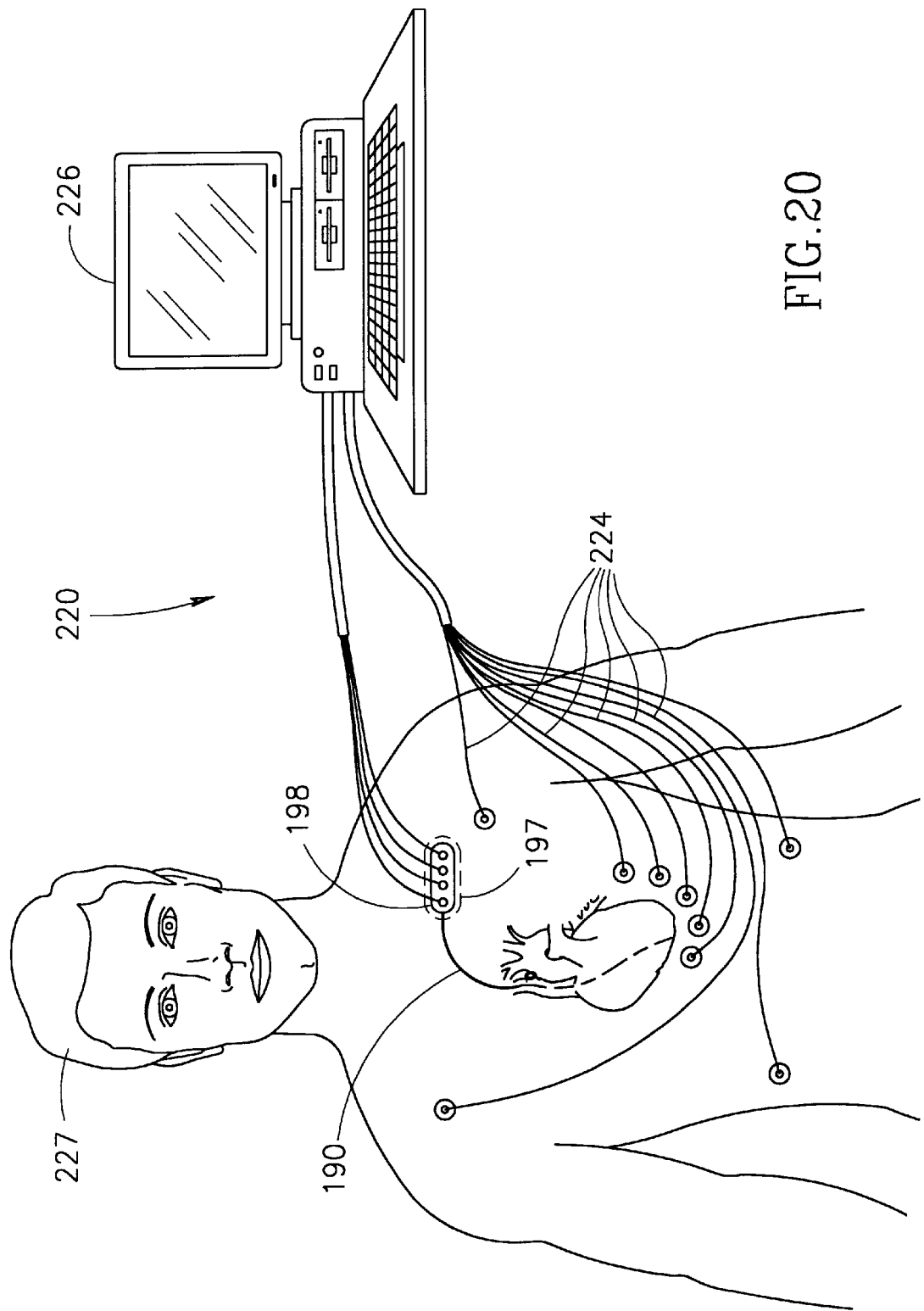
FIGS. 20–21 are schematic diagrams illustrating a system for minimally invasive heart transplant monitoring using the implantable pacing lead of FIG. 19, in accordance with a preferred embodiment of the present invention.
Figure 21:
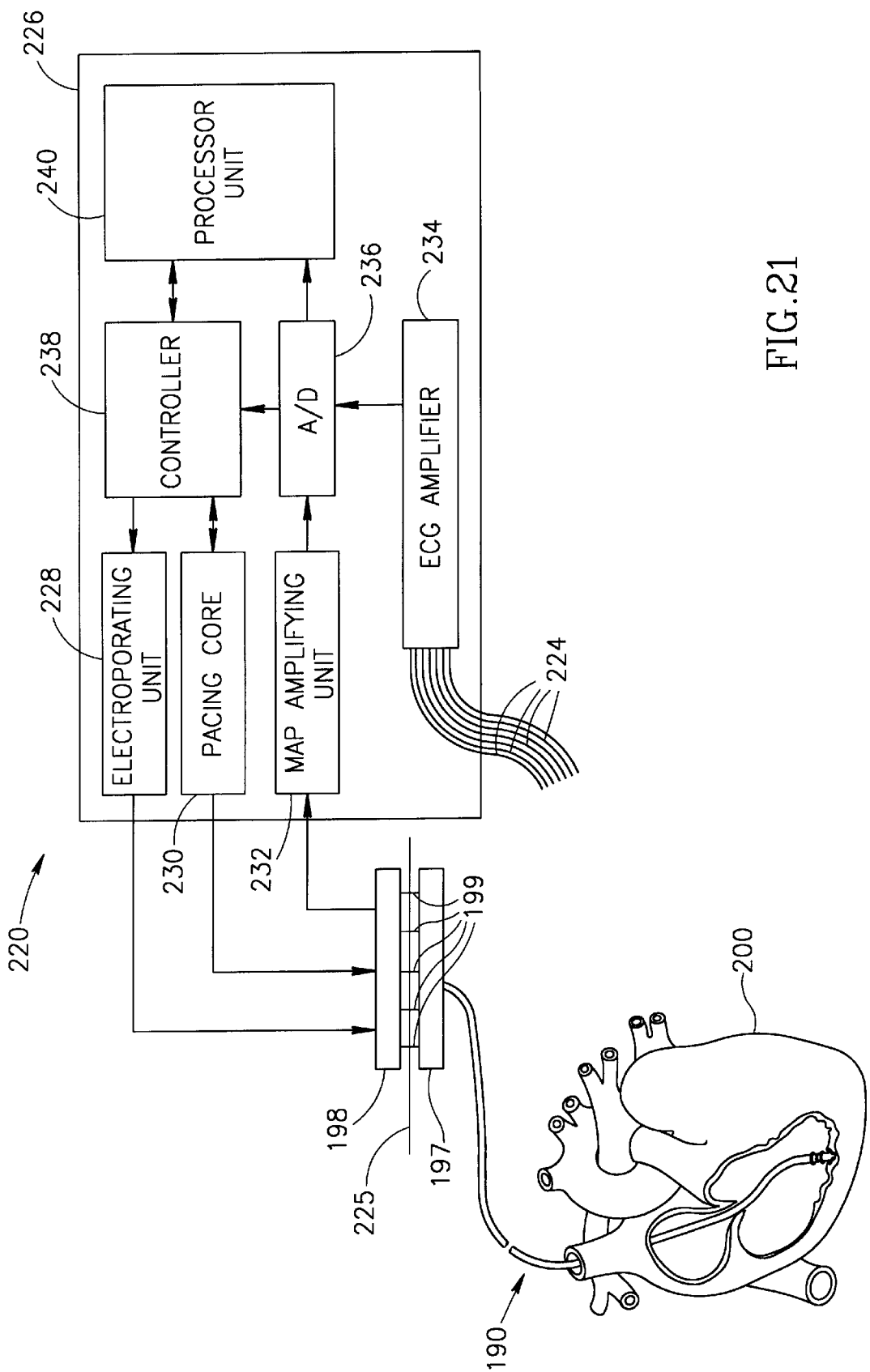

Reference is now made to FIGS. 20–21 which are schematic diagrams illustrating a system for minimally invasive heart transplant monitoring using the implantable pacing lead 190 of FIG. 18, in accordance with a preferred embodiment of the present invention. The system 220 includes the implantable lead 190 shown implanted in a transplanted heart 200 of a patient 227 and the trans-cutaneous electrical access port 197. It is noted that, the contour of the trans-cutaneous electrical access port 197 is illustrated in a broken line to indicate that it is subcutaneously implanted. The system 220 further includes a plurality of surface electrocardiogram (ECG) electrodes 224 shown to be attached to the patient for ECG monitoring. The plurality of ECG electrodes 224 are connected to an analyzer/controller unit 226. The analyzer/controller unit 226 is electrically connected to the electroporating electrode 207, the sensing electrode 209, the pacing electrodes 210 and the reference electrode 202 of the lead 190, by a trans-cutaneous connector 198 which is tran-cutaneously electrically connected to the contacts 199 of the trans-cutaneous electrical access port 197. The analyzer/controller unit 226 sends pacing signals to the pacing electrodes 210 and electroporating signals to the electroporating electrode 207 through the lead 190. The analyzer/controller unit 226 also receives MAP signals sensed by the sensing electrode 209 through the lead 190. The analyzer/controller unit 226 further receives ECG signals sensed by the ECG electrodes 224. The system 220 may be used for simultaneously monitoring the surface ECG of the patient 227 and the endocardially sensed MAP signals. The parameters of the recorded MAP signals may be used to monitor transplant rejection based on changes in recorded MAP parameters such as, inter alia, MAP DC baseline, MAP amplitude and APD and on the calculated ERP/APD ratio which is sensitive to changes in myocardial tissue viability.

Reference is now made to FIG. 21 which is a schematic functional diagram illustrating the analyzer/controller unit 226 of FIG. 20 in detail. The analyzer/controller unit 226 includes an electroporating unit 228 for delivering electroporating current pulses to the cardiac tissue subjacent the electroporating electrode 207. The analyzer/controller unit 226 also includes a MAP amplifying unit 232 for amplifying the signals sensed by the sensing electrode 209. The analyzer/controller unit 226 further includes a pacing core 230 for pacing the heart 200 through the pacing electrodes 210 (best seen in FIG. 19). The pacing core 230 may have it's own dedicated sensing electrode (not shown). However the pacing core 230 may use the MAP signal provided by the MAP amplifying unit 232 for controlling the timing of the pacing pulses of the pacing core 230 by feeding the digitized MAP signal from A/D 236 to appropriate sensing/triggering circuitry (not shown) included in the controller 238. It is noted that, the pacing core 230 may also use the sensing electrode 209 for delivering the pacing pulses, obviating the need for the pacing electrodes 210. The analyzer/controller unit 226 further includes a controller 238 connected to the electroporating unit 228 for synchronization of the electroporating pulse timing. The controller 238 is also connected to the pacing core 230 for controlling pacing pulse delivery. The MAP amplifying unit 232 is connected to an analog-to-digital converter unit (A/D) 236 for digitizing the amplified MAP signals. The analyzer/controller unit 226 further includes an ECG amplifier 234 for amplifying the ECG signals sensed by the ECG electrodes 224. The ECG amplifier 234 is connected to the A/D converter unit 236 for digitizing the ECG signals.

The analyzer/controller unit 226 further includes a processor unit 240 connected to the A/D converter unit 236 and to the controller 238. The processor unit 240 may be used for processing, storing and/or analyzing the output of the A/D converter unit 236 to obtain data representing MAP and ECG parameters. The processing of the data can be performed on-line or off-line after storing the data. It is noted that, in accordance with a preferred embodiment of the present invention (not shown), the processor unit 240 may be directly connected to the electroporating unit 228 and the pacing core 230 obviating the need for the controller 238. In such a case the processor unit 240 performs all the functions of the controller 238.

The processor unit 240 can be a central processing unit (CPU) such as a suitable microprocessor or micro-controller.

The analyzer/controller 226 may be a personal computer, a workstation, a mainframe or any other suitable type of computing device. The processing unit 240 may also be connected to a display device (not shown in FIG. 21) for displaying the ECG and/or the MAP signals, and/or any desired calculated MAP and ECG parameter. The processor unit 240 may also be used to control the pacing and the electroporation parameters through the controller 238. If the controller 238 is a programmable controller, the processor unit 240 may also be used for reprogramming the controller 238.

Figure 22A:
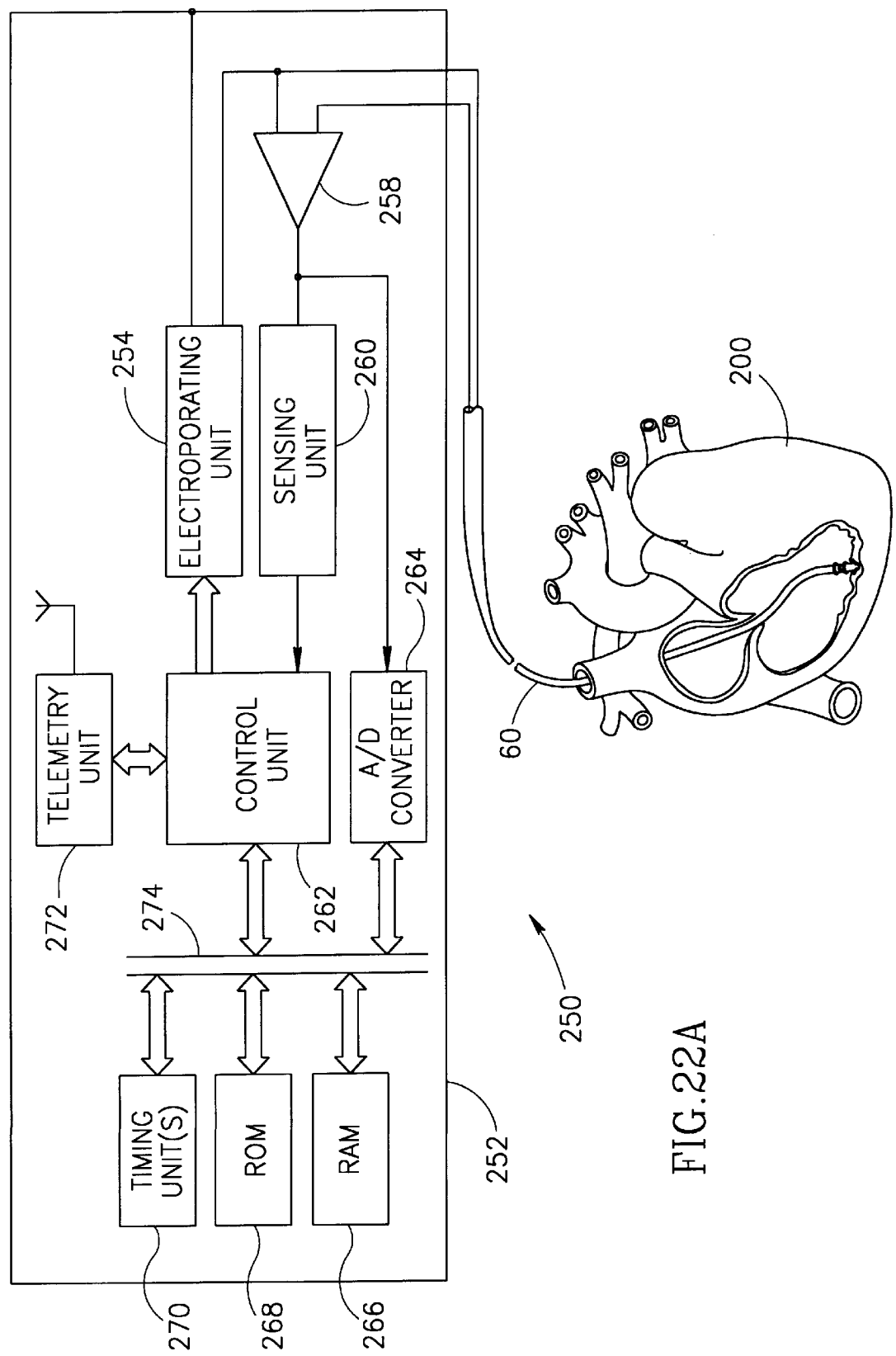
FIG. 22A is a schematic diagram illustrating an implantable device capable of chronically recording MAP signals, in accordance with another preferred embodiment of the present invention.

Reference is now made to FIG. 22A which is a schematic diagram illustrating an implantable device capable of chronically recording MAP signals, in accordance with another preferred embodiment of the present invention. The device 250 includes an implantable housing 252 connected to an implantable lead 60 (best seen in FIG. 6). The lead 60 includes a reference electrode 55 and a probe electrode 52. The probe electrode 52 is used for sensing of unipolar intracardiac electrogram (IEGM) signals and MAP signals as disclosed in detail hereinabove.

The device 250 further includes an electroporating unit 254 suitably connected to an amplifier 258 and to the reference electrode 55 and the probe electrode 52 of lead 60 for delivering electroporating current pulses to the myocardium as disclosed in detail hereinabove. The electroporating unit 254 may be identical to the electroporating unit 30 of FIGS. 3 and 4 or may be any other suitable circuit for delivering current pulses capable of causing membrane electroporation in the tissue subjacent the probe electrode 52. The amplifier 258 is electrically connected to a sensing unit 260 for providing the sensing unit 260 with the amplified sensed signal. Prior to the initiation of electroporation this signal is an IEGM signal. The sensing unit 260 is connected to a control unit 262. The sensing unit 260 receives the amplified unipolar IEGM signals and generates trigger signals indicating tissue activation. The trigger signals are received by the control unit 262 which generates a properly timed control signals for activating the electroporating unit 254 to generate electroporating current pulses.

The timing of the electroporating pulses is important, since the electroporating current pulses have the capability of exciting electrically-viable tissue, and may be arrhythmogenic if applied in an inappropriate manner. The application of the electroporating current pulses is thus timed to fall within the absolute refractory period of the cardiac action potential. The timing is performed similarly to the timing of the generation of plateau-control pulses performed by the devices for the control of excitable tissue disclosed by International Publication number WO 97/25098 to Ben-Haim et al. referenced hereinabove.

The amplifier 258 is connected to an analog to digital (A/D) converter 264 which digitizes the amplified signals and stores the digitized data in a random access memory (RAM) device 266. The control unit 262 is connected to the RAM device 266 through a data bus 274. The control unit 262 is also connected to a timing unit(s) 270 and to a read only memory (ROM) device 268 over the data bus 274. The ROM device 268 may be programmed with software for operating the device 250. The timing unit(s) 270 provides one or more clock signals for operating and synchronization of the various components of the device 250. The control unit 262 is also connected to a telemetry unit 272. The control unit 262 can access the digitized data stored in RAM device 266 and send this stored data to the telemetry unit 272 for wireless transmission of the stored data to a telemetry receiver (not shown) outside the body of the patient.

After implantation of the device 250 in the patient, the device 250 may be used to deliver appropriately timed electroporation pulses to the cardiac tissue and to record MAP signals as disclosed hereinabove. The stored MAP signals may be then transmitted to an external telemetry receiver (not shown) and stored in an analyzing system (not shown) such as a computer or any other processing system for further processing and analysis of the stored MAP signals to produce and display clinically relevant digitized MAP raw data, calculated MAP parameters and other MAP related data. Tissue electroporation and MAP recording may be initiated automatically by the software program stored in the ROM device 268. The automatic initiation of electroporation and MAP recording may be performed periodically at a suitable frequency which is empirically found not to cause excessive tissue damage and electrical uncoupling of excitable myocardial cells. The automatic initiation of electroporation may also be performed aperiodically at pre-programmed times. The initiation of electroporation and MAP recording may also be performed non-automatically at desired times by wirelessly transmitting an appropriate activation signal to the telemetry unit 272.

The device 250 of FIG. 22A is especially suited for chronic assessment of the progression of cardiomyopathy and heart transplant rejection, precise titration of pharmaceutical myocardial therapies, and for predicting life-threatening arrhythmic events. The device 250, in the configuration shown, is capable of providing an attending physician with MAP parameter data for evaluation as disclosed hereinabove. Additionally, if the patient has access to a monitoring device (not shown), the patient can access the MAP recordings and processed data or real-time digitized signals obtained by the implanted device 250, and relay the information to the attending physician via telephone, the internet or by any other telemedicine means known in the art.

While the device 250 may be useful for chronically monitoring certain MAP parameters, it may be desirable to add a pacing capacity to the device to determination of the myocardial refractory period.

Figure 22B:
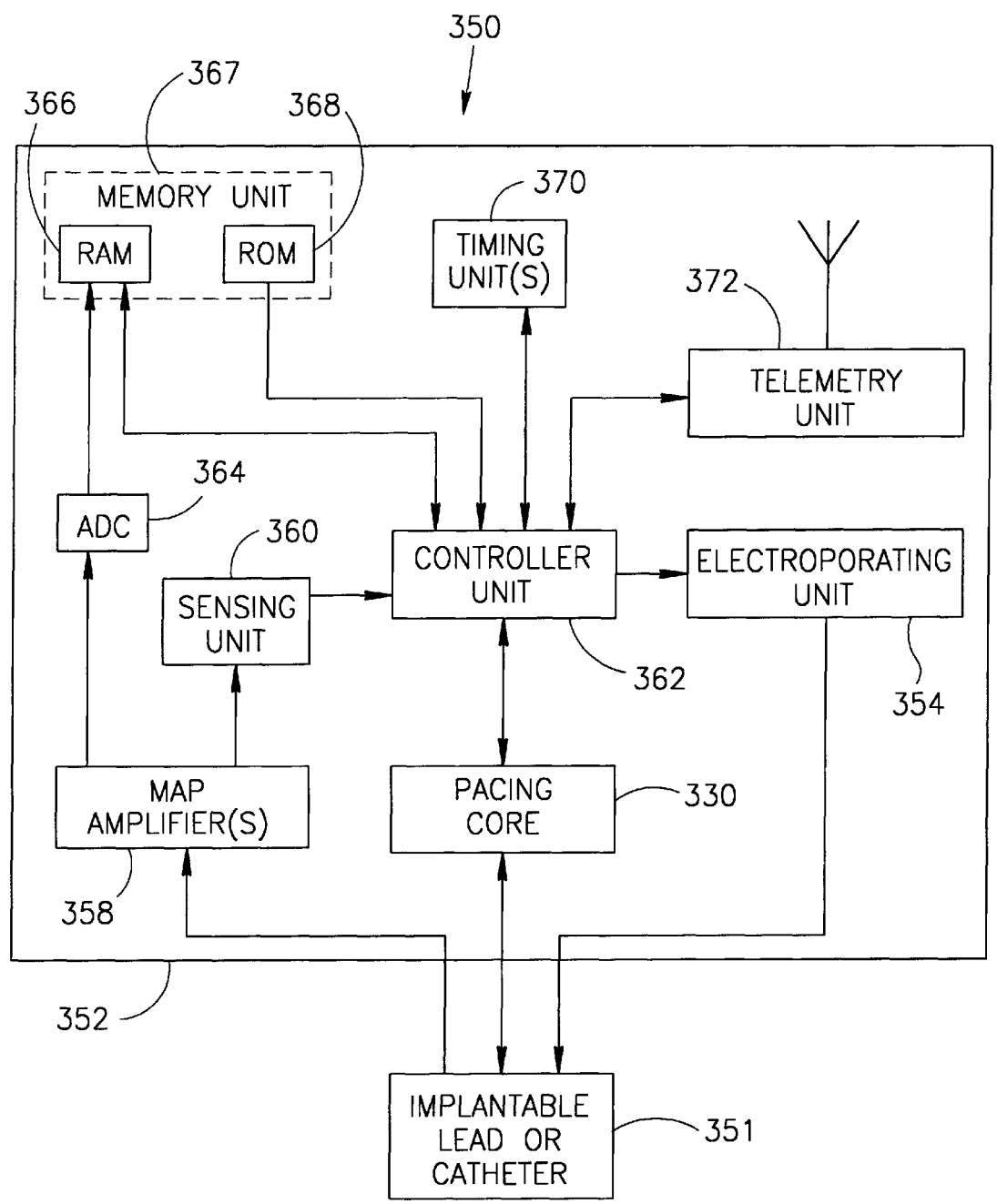
FIG. 22B is a schematic diagram illustrating an implantable pacing device for chronically recording MAP signals and for determining the duration of refractory periods, in accordance with another preferred embodiment of the present invention.

Reference is now made to FIG. 22B which is a schematic diagram illustrating an implantable pacing device for chronically recording MAP signals and for determining the duration of refractory periods, in accordance with a preferred embodiment of the present invention.

The device 350 of FIG. 22B includes an implantable housing 352 and an implantable lead or catheter 351 attached thereto. Preferably, the lead or catheter 351 may be similar to the lead 190 of FIGS. 18 and 19. However other types of implantable leads or catheters may also be used which include a plurality of electrodes (not shown) suitable for pacing, for electroporating and for sensing of unipolar intracardiac electrogram (IEGM) signals and MAP signals as disclosed in detail hereinabove.

The housing 352 includes therewithin an electroporating unit 354. The electroporating unit 354 may be electrically connected to an amplifier 358 (electrical connection not shown in FIG. 22B) as disclosed for the electroporating unit 254 and the amplifier 258 of FIG. 22A, respectively, for delivering electroporating current pulses to the myocardium (not shown). The amplifier 358 is electrically connected to a sensing unit 360 for providing the sensing unit 360 with the amplified sensed IEGM signal. The sensing unit 360 is connected to a controller 362. The sensing unit 360 receives the amplified unipolar IEGM signals and generates trigger signals indicating tissue activation. The trigger signals are received by the controller 362 which generates properly timed control signals for activating the electroporating unit 354 to generate electroporating current pulses as disclosed hereinabove.

The amplifier 358 is connected to an analog to digital converter (ADC) 364 which digitizes the signals amplified by the amplifier 358 and stores the digitized data in a random access memory (RAM) device 366 included in a memory unit 367. The controller 362 is also connected to the RAM device 366. The controller 362 is also connected to a timing unit(s) 370 and to a read only memory (ROM) device 368 which is included in the memory unit 367. The ROM device 368 may be programmed with software for operating the device 350. The timing unit(s) 370 provides one or more clock signals for operating and synchronization of the various components of the device 350. The controller 362 is also connected to a telemetry unit 372. The controller 362 can access the digitized data stored in the RAM device 366 and send this stored data to the telemetry unit 372 for wireless transmission of the stored data to a telemetry receiver (not shown) outside the body of the patient.

The device 350 further includes a pacing core 330. The pacing core 330 is connected to the controller unit 362 for controlling the timing of the pacing signals. The pacing core 330 is also suitably connected to the lead or catheter 351 for delivering the pacing signals to the pacing electrode(s) (not shown) of the lead or catheter 351. Preferably, the IEGM signal or the MAP signal sensed by the sensing electrode (not shown) of the lead or catheter 351 is used after amplification by the amplifier 358 as output to the sensing unit 360. The sensing unit 360 sends trigger signals to the controller 362. The controller 362 sends control signals to the pacing core 330 to activate the pacing core 330 which sends pacing signals to the myocardial muscle through the pacing electrode(s) (not shown).

Thus, the device 350 may function as an implantable pacer device having chronic MAP recording and telemetry capabilities similar to the chronic MAP recording and telemetry capabilities of the device 250 of FIG. 22A. In addition to the pacing function, the device 350 has the additional capability to determine the effective refractory period (ERP). The device 350 can determine the duration of refractory periods by controllably imposing pacing pulses at various different times during the various phases of the recorded MAP signals. Methods for determining the duration of the refractory periods of cardiac muscle by delivering stimulating pulses at different times within the MAP phases are known in the art and are not the subject of the present invention. Such methods are disclosed by Koller, et al., in an article titled "RELATION BETWEEN REPOLARIZATION AND REFRACTORINESS DURING PROGRAMMED ELECTRICAL STIMULATION IN THE HUMAN RIGHT VENTRICLE", published in Circulation, 91(9), 2378–2384, 1995, incorporated herein by reference.

After implantation of the device 350 in the patient, the device may be used to deliver appropriately timed electroporation pulses to the cardiac tissue and to record MAP signals as disclosed hereinabove. The stored MAP signals may be then transmitted to an external telemetry receiver or transceiver (not shown) and stored in an analyzing system (not shown) such as a computer or any other processing system for further processing and analysis of the stored data to produce and display clinically relevant digitized MAP raw data, calculated MAP parameters and other MAP related data such as the determined ERP. Tissue electroporation and MAP recording may be initiated automatically by the software program stored in the ROM device 368. The automatic initiation of electroporation and MAP recording may be performed periodically at a suitable frequency which is empirically found not to cause excessive tissue damage or excessive electrical uncoupling of myocardial cells. The automatic initiation may also be performed aperiodically at pre-programmed times. The initiation of electroporation and MAP recording may also be performed non-automatically at desired times by wirelessly transmitting an appropriate activation signal to the telemetry unit 372.

While the device 350 of FIG. 22B may be used for long term clinical follow-up of the ERP at a single site of the myocardium such as the ventricular myocardium or other cardiac sites, in certain patients with increased risk of developing arrhythmias it may be advantageous to determine the duration of refractoriness at various sites within a heart chamber for assessing the dispersion of refractoriness within the heart chamber.

Figure 22C:
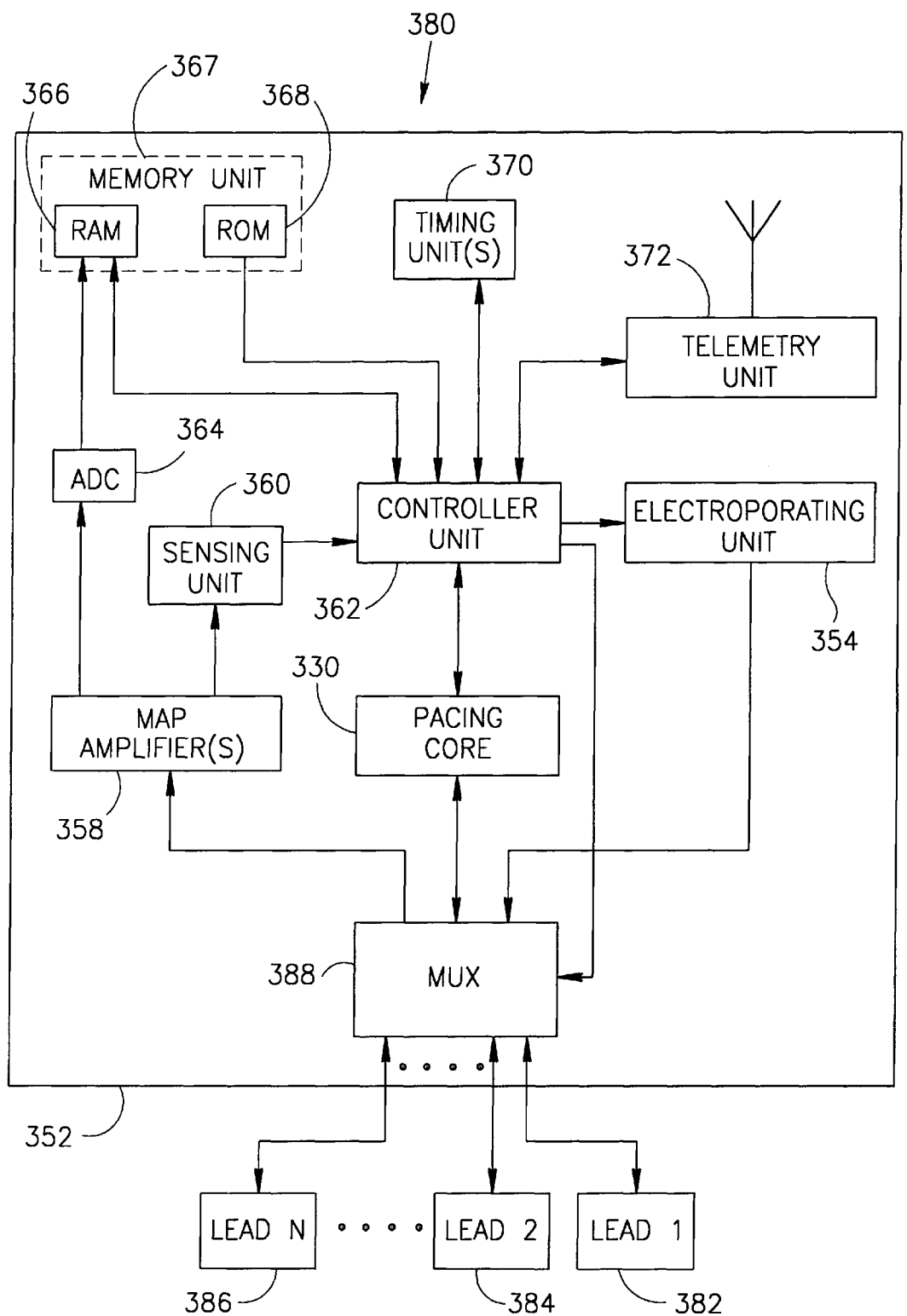
FIG. 22C which is a schematic diagram illustrating an implantable pacing device for chronically recording MAP signals and for determining the duration of refractory periods at multiple sites within the heart, in accordance with a preferred embodiment of the present invention.

Reference is now made to FIG. 22C which is a schematic diagram illustrating an implantable pacing device for chronically recording MAP signals and for determining the duration of refractory periods at multiple sites within the heart, in accordance with a preferred embodiment of the present invention.

The device 380 is similar to the device 350 of FIG. 22B except that while the device 350 includes a single lead 351, the device 380 includes a plurality of N leads 382, 384 and 386 and a multiplexer (MUX) 388 connected to the plurality of the leads 382, 384 and 386. The multiplexer 388 is connected to the pacing core 330, the MAP amplifier(s) 358, the electroporating unit 354 and the controller unit 362 of the device 380. The controller 362 controls the multiplexer 388 to select which lead of the plurality of N leads 382, 384 and 386 is connected to the pacing core 330, the MAP amplifier(s) 358 and the electroporating unit 354 at any particular time during the operation of the device 380. Thus, electroporation and MAP measurements can be performed from any selected single lead of the plurality of leads 382, 384 and 386 as disclosed in detail hereinabove.

Typically, the device 380 includes two leads (N=2) which will be implanted at two different sites of the right ventricle. However, the device 380 may also include a number of leads which is greater than 2 and the lead implantation sites may vary within the heart.

After implantation, the device 380 may operated to monitor MAP parameters including ERP as disclosed hereinabove for the device 350 of FIG. 22B. For example, the lead 382 may first be used to perform a series of ERP measurements at the site of implantation thereof. The measurement series includes the delivery of pacing pulses at different times during MAP repolarizations as disclosed in detail hereinabove. The controller 362 may then control the multiplexer 388 to disconnect the lead 382 from the pacing core 330, the MAP amplifier(s) 358 and the electroporating unit 354, and to connect the lead 384 to the pacing core 330, the MAP amplifier(s) 358 and the electroporating unit 354. The lead 384 is then used for performing another series of ERP measurements at the site of implantation thereof. If desired, this procedure may be repeated for other leads. The data representing each of the series of measurements is stored and transmitted as disclosed in detail for the device 350 of FIG. 22B hereinabove. The data may then be stored and processed by an analysis system (not shown) such as the analyzer/controller 226 of FIGS. 20–21 or a personal computer or another suitable analysis system, to obtain the ERP values of the myocardial muscle at the different lead implantation sites. It is noted that, the indicated sequence of performing the measurements at the different lead implantation sites is used by way of example only and that other different sequences may be used.

Permanent monitoring of local activation and repolarization characteristics by the device 380 is advantageous. The device 380 can be used to monitor the effects of antiarrhythmic drugs on myocardial repolarization at specific intervals following antiarrhythmic drug therapy.

Another advantage of chronic MAP recording using the device 380 is that it enables the monitoring of myocardial changes related to the onset of proarrhythmic events. Progression of cardiomyopathy and heart transplant rejection are other fields that would benefit from continuously available chronic MAP recording. As understanding of the cellular basis of arrhythmias grows, abnormal changes of MAP signals recorded by permanently implanted electrodes and transmitted by telemetry may become predictors and warning signals of life-threatening arrhythmic events.

The ERP values obtained may be also clinically used for assessing the dispersion of refractoriness within the heart chamber yielding information suitable for predicting life-threatening arrhythmic events.

It is noted that, while in the method and the devices disclosed hereinabove for chronically recording MAPs the injury-like currents and depolarization of myocardial tissue was induced by electroporating current pulses, other methods and devices may be used for inducing injury-like currents and depolarization of myocardial tissue for chronically recording MAPs.

Figure 23:
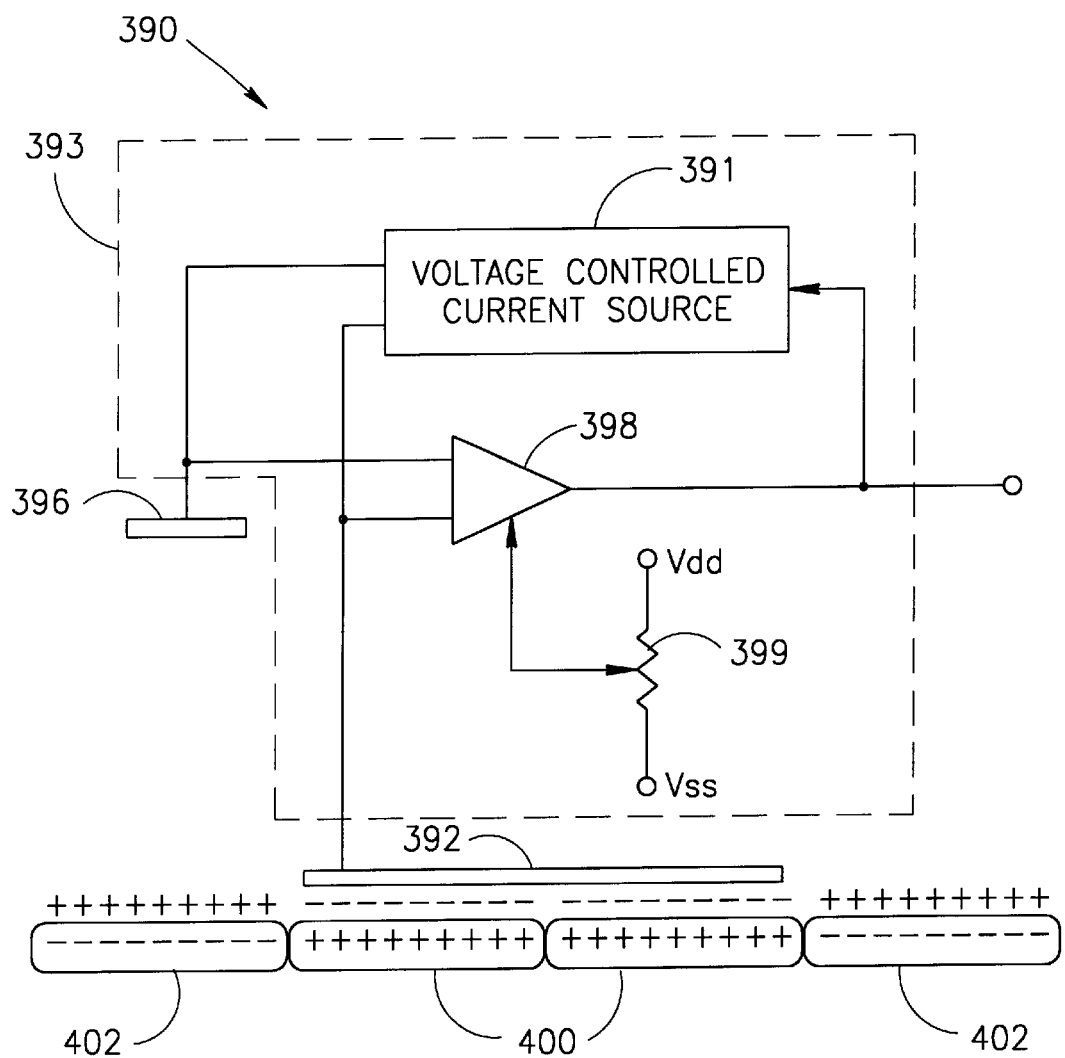
FIG. 23 is a schematic diagram illustrating a device for chronic MAP recording by electrostatic induction, in accordance with a preferred embodiment of the present invention.

Reference is now made to FIG. 23 which is a schematic diagram illustrating a device for chronic MAP recording by electrostatic induction, in accordance with a preferred embodiment of the present invention.

The device 390 includes a voltage-clamp unit 393 electrically connected to a probe electrode 392 and to a reference electrode 396. The voltage-clamp unit 393 includes a voltage controlled current source 391 electrically connected to the probe electrode 392 and to the reference electrode 396. The probe electrode 392 and the reference electrode 396 are similar to the probe electrode 22 and the reference electrode 26 of FIG. 3. The voltage-clamp unit 393 further includes an amplifier 398. The probe electrode 392 and the reference electrode 396 are also electrically connected to the amplifier 398.

The voltage-controlled current source 391 is electrically connected to the amplifier 398 such that it attempts to maintain the potential between the probe electrode 392 and the reference electrode 396 at a constant non-zero voltage. The value of this holding voltage is determined by the offset voltage which is fed to the amplifier 398 by an offset potentiometer 399.

The voltage imposed on the probe electrode 392 causes a depolarization in the excitable tissue subjacent the probe electrode 392 and induces injury-like currents in the electrically-coupled cells 400. The electrostatic induction of electrical charges by the probe electrode 392 is sufficiently strong to induce a depolarization in the cells 400 underlying the probe electrode 392. The cells 402 which are not underlying the probe electrode 392 are not substantially depolarized. Since the cells are 400 and 402 are electrically coupled, injury-like currents (not shown) flow into the cells 400 and between the cells 400 and the cells 402 as disclosed hereinabove.

The cells 400 of the tissue region subjacent the electrode 392 are inactivated and thus create an electrostatically-depolarized zone of substantially stable injury-like currents which enables the recording of MAPs as disclosed in detail hereinabove. As action potentials propagate through the electrostatically-depolarized zone, the current invested by the voltage controlled current source 391 to maintain the potential difference between the electrodes 392 and 396 tracks the cellular currents in excitable tissue regions adjacent the inactivated electrostatically depolarized zone. This current signal represents the MAP signal.

The electrostatic-depolarization action of the device 390 may be controllably stopped by zeroing the potential difference imposed by the voltage-clamp unit 393 between the probe electrode 392 and the reference electrode 396. The device 390 enables chronic MAP recording since the potential difference imposed between the probe electrode 392 and the reference electrode 396 may be modified to compensate for electrode encapsulation induced changes in the tissue subjacent the probe electrode 392 and for other post-implantation changes such as electrical de-coupling of some of the cell layers under the electrode from the rest of the excitable tissue as disclosed in detail hereinabove.

U.S. Pat. No. 5,156,149 to Hudrlik discloses a sensor for detecting cardiac depolarizations adapted for use in cardiac pacemaker. The sense amplifier disclosed by Hudrlik includes active circuitry which establishes and maintains a constant field density between two electrode poles, effectively clamping them together at a substantially fixed potential difference. The amount of current or power required to maintain this condition in the steady state is monitored and forms the basis for detection of the passing depolarization wavefront. In contrast, the voltage clamp unit 393 of the present invention specifically forces the potential difference between the probe electrode 392 and the reference electrode 396 to a non-zero value sufficient to electrically depolarize the electrically coupled tissue subjacent the electrode and to induce injury-like current therein which serves as the basis of recording of the MAP signal.

It will be appreciated by those skilled in the art that, the voltage clamp unit 393 of the device 390 of FIG. 23 may replace the electroporating unit 228 and the MAP amplifying unit 232, of FIG. 21, the electroporating unit 254 and the MAP amplifier 258 of FIG. 22A, the electroporating unit 354 and the MAP amplifier 358 of FIG. 22B, and the electroporating unit 354 and the MAP amplifier 358 of FIG. 22C, with appropriate electrical modifications, for chronic MAP recording by electrostatic-depolarization.

Figure 24:
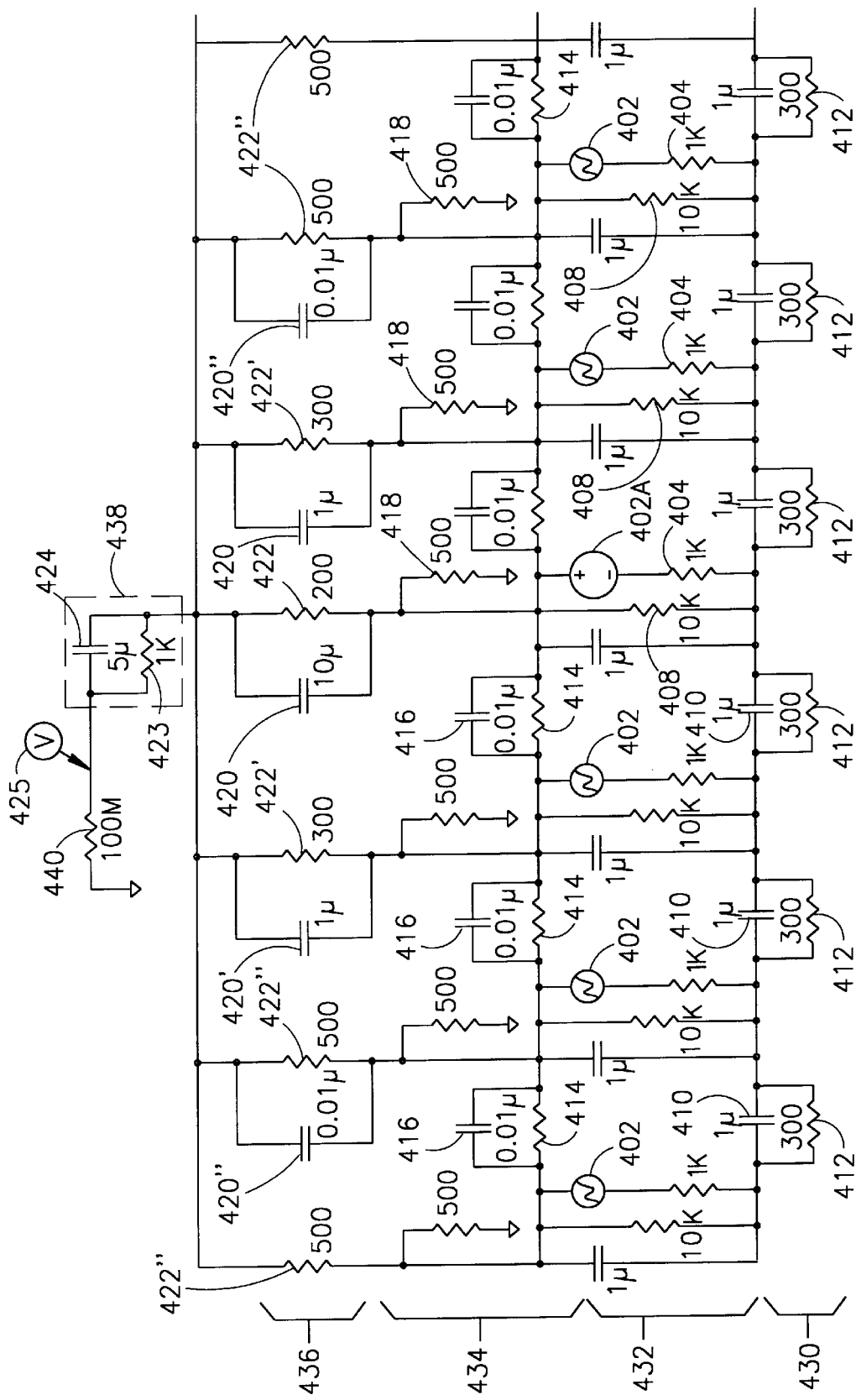
FIGS. 24–26 are schematic diagrams illustrating a "cable" model of the myocardium used for simulation of IEGM, TAP, pressure induced MAP, and electrostatically induced MAP recordings.
Figure 25:
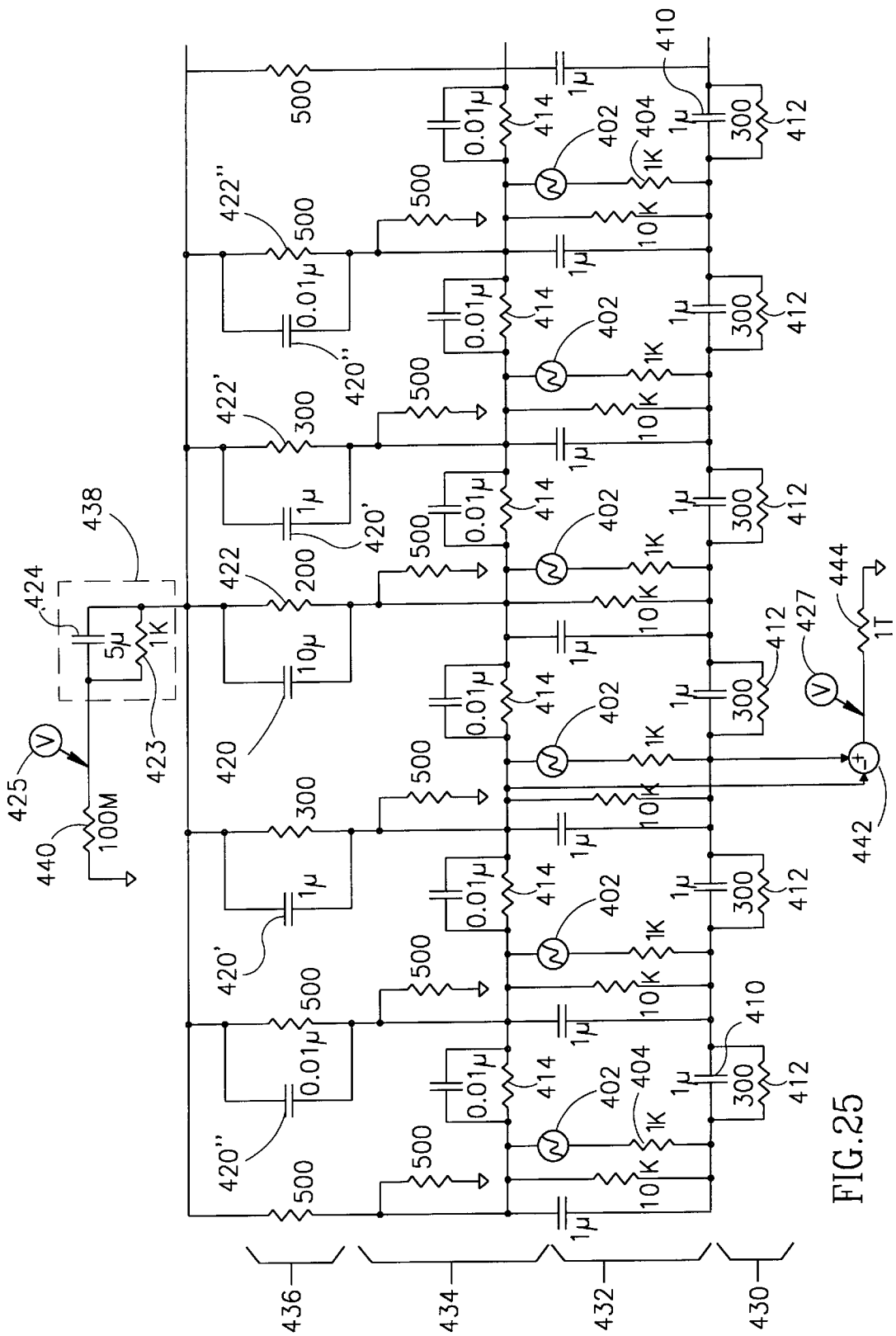
Figure 26:
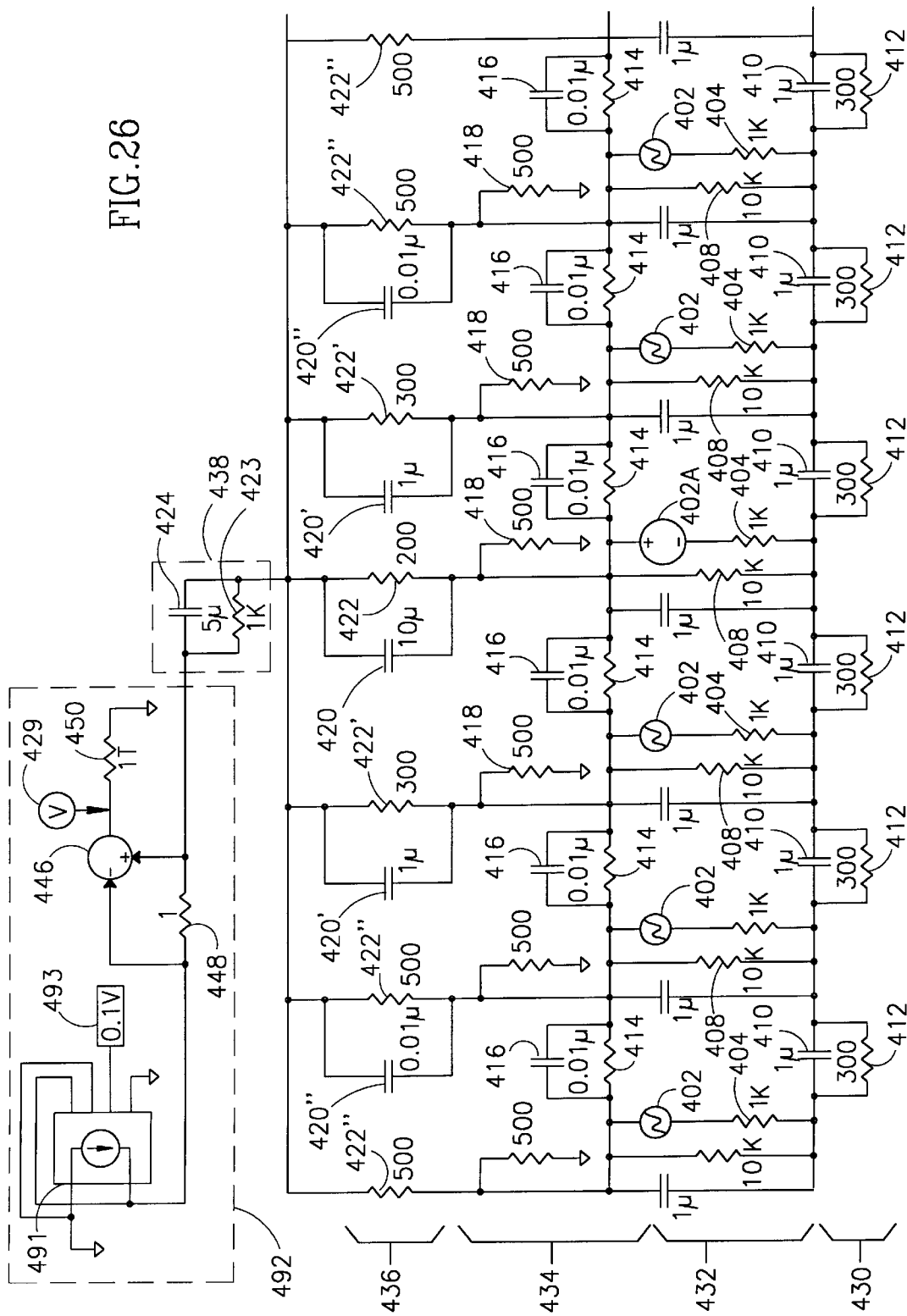

Reference is now made to FIGS. 24–26 which are schematic diagrams illustrating a "cable" model of the myocardium used for simulation of IEGM, TAP, pressure induced MAP, and electrostatically induced MAP recordings.

FIGS. 24–26 illustrate a simple cable model of a the myocardium used for simulation of the generation of the TAP, standard unipolar IEGM, pressure induced bipolar MAP and electrostatically induced bipolar MAP. The simulations were performed using the software program Micro-Sim Pspice, commercially available from OrCAD Inc. OR, U.S.A. In FIGS. 24–26, resistor values are given in ohms unless otherwise labeled, capacitor values are given in microfarads and voltage values are in volts.

In the model illustrated in FIG. 24, The cell membrane is represented by the model part indicated by the open brackets 432. The piecewise voltage sources 402 in series with 1 KΩ resistors 404 simulate the membrane activity. Passive properties of a membrane section are simulated by 1 $\mu$F capacitors 406 in parallel with 10 KΩ resistors 408. The Intra-cell and inter-cell coupling is represented by the model part indicated by the open bracket labeled 430 and is simulated using 1 $\mu$F capacitors 410, each in parallel with a 300Ω resistor 412. The extracellular fluid properties are represented by the model part indicated by the open bracket labeled 434 and are simulated by a chain of 500Ω resistors 414, each in parallel with a 0.01 $\mu$F capacitor 416.

Passive model parameters follow the results disclosed in the article by P. Fu and B. J. Bardakjian, titled "SYSTEM IDENTIFICATION OF ELECTRICALLY COUPLED SMOOTH MUSCLECELLS: THE PASSIVE ELECTRICAL PROPERTIES", published in IEEE Transactions on Biomedical Engineering, 38(11), pp. 1130–1140, 1991, incorporated herein by reference.

Briefly, the impedance between each element of extracellular fluid and the overall reference point (ground) is simulated by 500Ω resistors 418. Electrode coupling is represented by the model part indicated by the open bracket labeled 436 and is simulated by a logarithmically-distributed network of capacitors, 420, 420', 420", (0 to 10 $\mu$F range) shunted by relatively low value resistors, 422, 422' and 422", respectively (200Ω to 500Ω range). The electrode-tissue interface is represented by the model part 438 and is represented by a simplified Helmholz network including a 1 KΩ resistor 423 in parallel with a 5 $\mu$F capacitor 424. The DC-coupled amplifier input impedance is represented by a 100 MΩ resistor 440 across which the output signal representing the simulated pressure-induced MAP is measured by the simulated voltage probe 425.

In the MAP cable model of FIG. 24, one of the piecewise voltage sources 402 has been replaced by a constant voltage source 402A simulating the depolarization caused by pressing the MAP-recording catheter against the tissue.

FIG. 25 illustrates the model used to simulate the standard monopolarly recorded IEGM. The model components are similar to the components illustrated in FIG. 24, except that the voltage source 402A is now replaced by an active piecewise voltage source 402. The trans-cellular action potential (TAP) is differentially measured through an ideal differential measurement device simulated by a differential block 442 connected across the simulated cell membrane represented by the open bracket 432. The output signal of the differential block 442 develop across a 1 TΩ (1 TΩ=$10^{12}$Ω) resistor 444 and is measured by a voltage probe 427.

It is noted that this value for the resistor 444 is arbitrarily chosen to satisfy the simulation program requirements and that other values of the resistor 444 such as 100 MΩ may be used without significantly affecting the results of the simulation.

FIG. 26 illustrates the model used for simulating an electrostatically induced MAP recorded using devices similar to the device 390 of FIG. 23. The model components are similar to the components illustrated in FIGS. 24, except that the capacitor 424 is connected to a voltage clamp circuit 492 instead of being connected to the 100 MΩ resistor 440 of FIG. 24. The voltage clamp circuit 492 includes a voltage controlled current source 491 which has a fixed offset 493 of 100 millivolts. The voltage drop across the 1Ω resistor 448 represents the electrostatically-induced MAP and is measured by a voltage probe 429 at the output of a differential block 446 connected across the resistor 448. For convenience, the resistance value of the resistor 448 was chosen to be 1Ω so that a clamping current of 1.0 ampere flowing through it will develop a voltage difference of 1.0 volt across the resistor 448. It is noted that the 1 TΩ value for the resistor 450 connected to the output of the differential block 446 is arbitrarily chosen to satisfy the simulation program requirements and that other values of the resistor 450 such as 100 MΩ may be used without significantly affecting the results of the simulation.

Figure 27A:
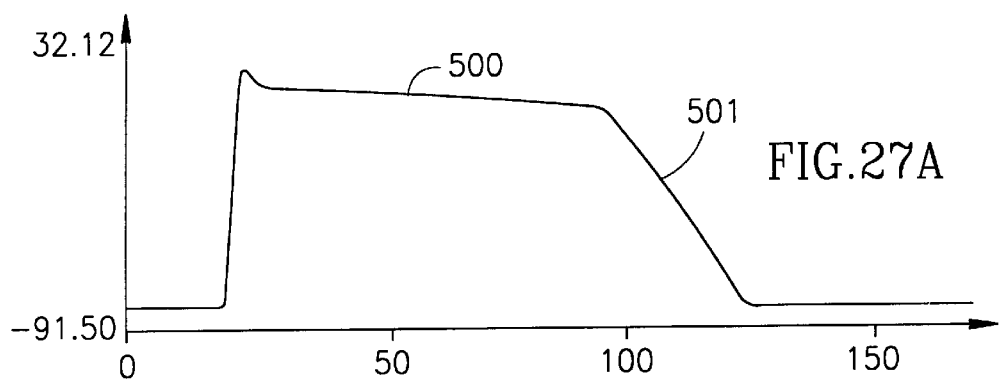
FIGS. 27A–27D are schematic graphs illustrating the results of the simulations performed using the cable models of FIGS. 24–26.

Reference is now made to FIGS. 27A–27D which are schematic graphs illustrating the results of the simulations performed using the cable models illustrated in FIGS. 24–26. FIG. 27A is a graph illustrating a curve 500 representing an idealized cardiac transcellular potential signal. The vertical axis represents the signal's amplitude in millivolts and the horizontal axis represents time in milliseconds.

Figure 27B:
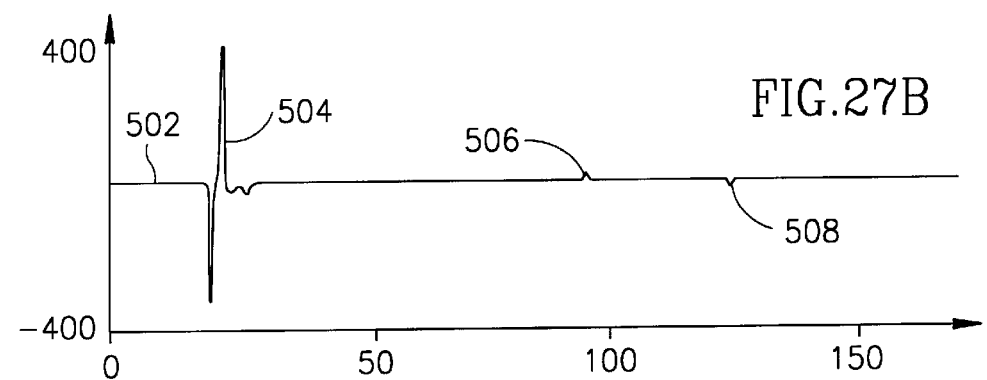

FIG. 27B is a graph illustrating a curve 502 representing the IEGM signal simulated using the model illustrated in FIG. 25. The curve 502 includes a multi-phasic disturbance 504 representing the signal caused by the leading-edge of the propagating action potential of FIG. 27A. The vertical axis represents the signal's amplitude in microvolts and the horizontal axis represents time in milliseconds. Small disturbances 506 and 508 in the curve 502 are seen at the times corresponding with the beginning and the end respectively, of the fast repolarization phase 501 of the curve 500 of the idealized simulated cardiac transcellular potential signal of FIG. 27A.

Figure 2:
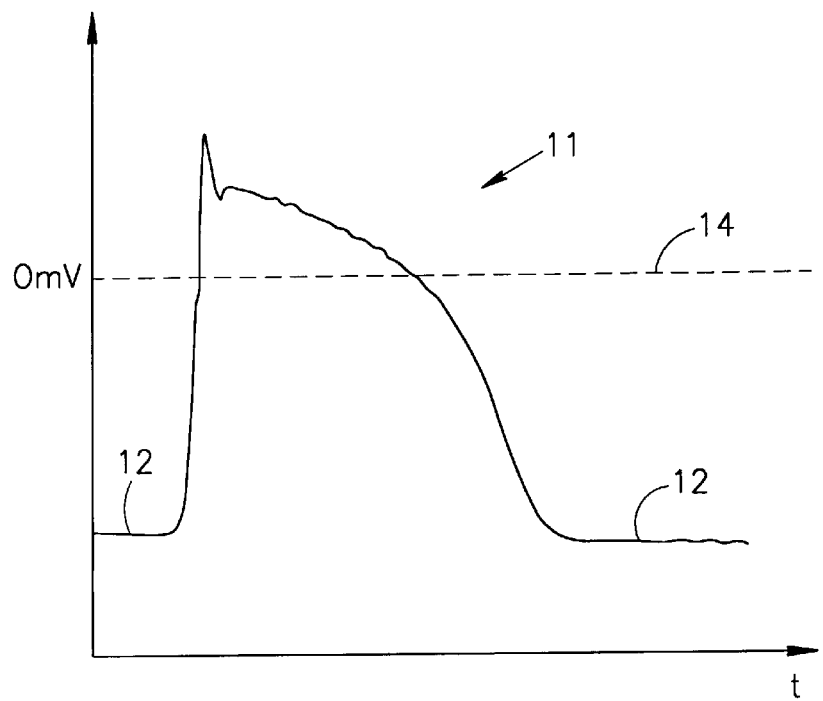
FIG. 2 is a schematic is a graph schematically illustrating the shape of a cardiac MAP signal recorded using a prior art contact electrode.
Figure 27C:
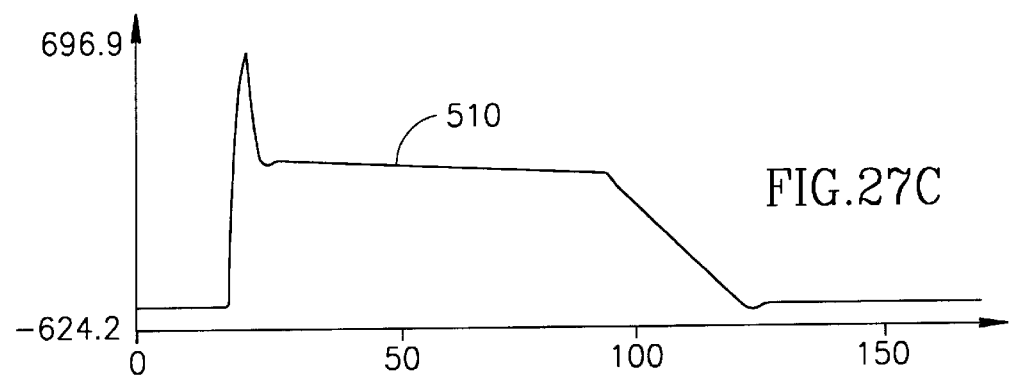

FIG. 27C is a graph illustrating a pressure induced MAP signal simulated using the model illustrated in FIG. 24 corresponding to the transcellular action potential illustrated in FIG. 27A and simulated using the model parameters illustrated in FIG. 25. The vertical axis represents the signal's amplitude in microvolts and the horizontal axis represents time in milliseconds. The curve 510 representing the simulated pressure induced MAP signal closely resembles the curve 500 of FIG. 27A representing the simulated trans-cellular action potential. It is noted that, the simulated MAP signal is characterized, inter alia, by a non-zero DC level of the baseline as illustrated in the baseline 12 of the recorded MAP signal of FIG. 2.

Figure 27D:
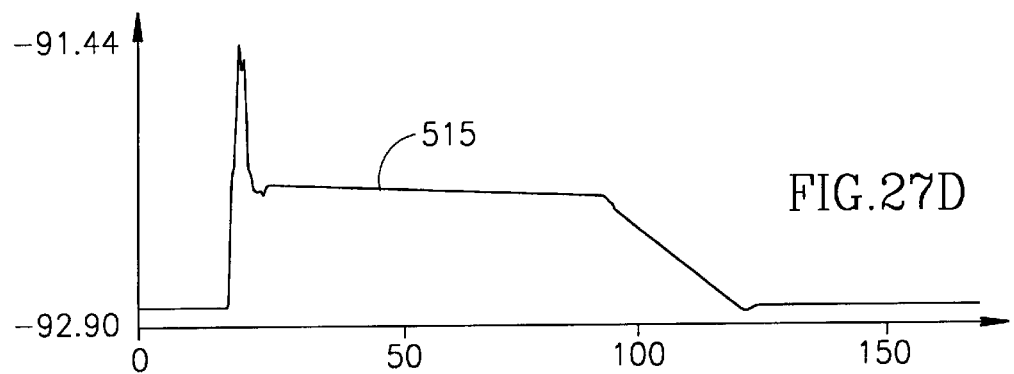

FIG. 27D is a graph illustrating a simulated electrostatically induced MAP signal, simulated using the model of FIG. 26. This electrostatically induced MAP signal corresponds to the transcellular action potential illustrated in FIG. 27A and simulated using the model parameters of FIG. 25. The vertical axis represents the signal's amplitude in microvolts and the horizontal axis represents time in milliseconds. The curve 515 representing the simulated electrostatically induced MAP signal closely resembles the curve 500 of FIG. 27A, and the curve 510 of FIG. 27C representing the simulated trans-cellular action potential and the simulated pressure induced MAP, respectively.

It will be appreciated by those skilled in the art that, the simulations illustrated in FIGS. 27A–27D using the membrane models of FIGS. 25–26 assume only a very small number of participating cells. Consequently, the amplitude of the simulated IEGM and MAP signals is much lower than that obtained from real hearts. Recorded IEGM signals are typically in the 0.1 mV–10 mV range, and recorded MAP signals are typically in the 5 mV–20 mV range.

While the electroporation and electrostatic methods may be used for chronic MAP recording as disclosed in detail hereinabove, other methods may also be used which are based on controlled reversible localized induction of injury-like currents and depolarization in myocardial tissue.

Thermal-Induction of Localized Myocardial Depolarization

Similarly to frank traumatic tissue injury, thermal damage of the myocardium can create injury currents which serve as the basis for recording MAPs. Although tissue burns were used at the beginning of the century to generate injury currents, non-destructive thermal stimulation may be used for generating reversible injury-like currents suitable for MAP recording. For example, in an article titled "CELLULAR PHYSIOLOGICAL EFFECTS OF HYPERTHERMIA ON ISOLATED GUINEA PIG PAPILLARY MUSCLE; IMPLICATIONS FOR CATHETER ABLATION", published by Nath et al. in Circulation, Vol. 88;4 part 1, pp. 1826–1831, 1993, incorporated herein by reference, the authors disclose a depolarization and loss of excitability caused by brief hypothermia in the temperature range of 38°–56 ° C. in guinea pig papillary muscle cells. The loss of cellular excitability was found to be reversible for hypothermia in the temperature range of 42.7°–51.3° C.

Figure 28:
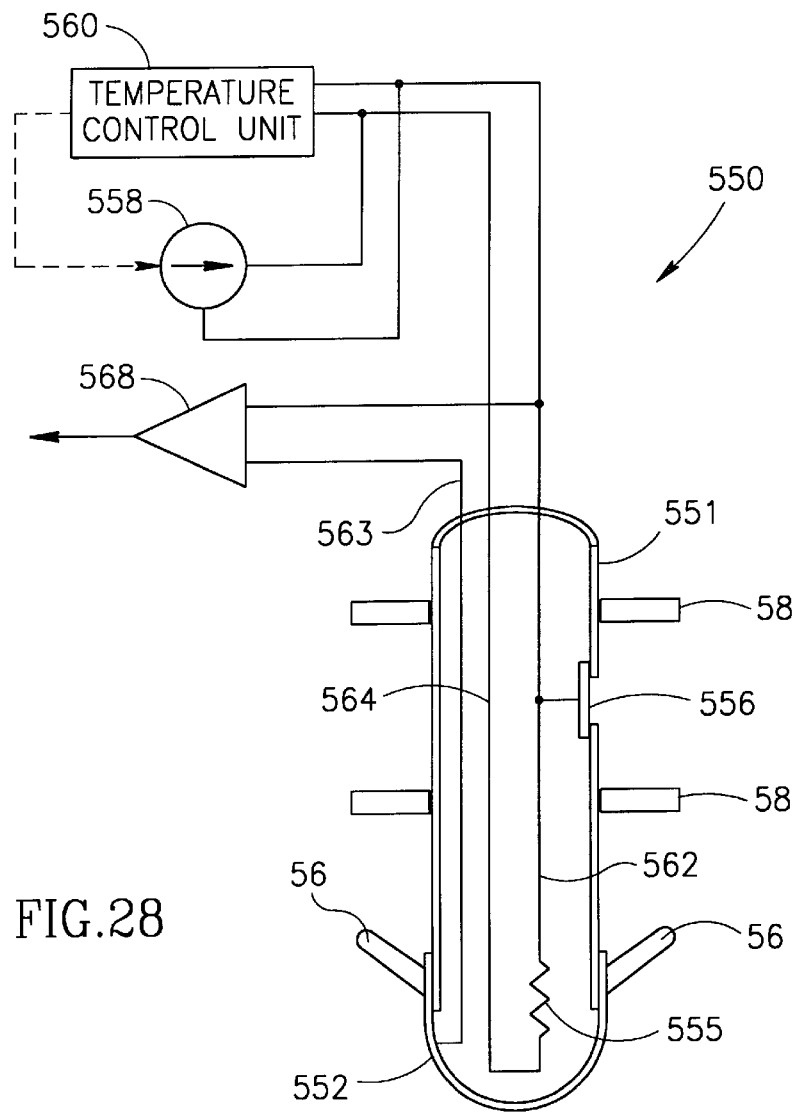
FIG. 28 is a schematic diagram of a device for chronic MAP recording using resistive heating of the myocardium, in accordance with another preferred embodiment of the present invention.

Reference is now made to FIG. 28 which is a schematic diagram of a device 550 for chronic MAP recording using resistive heating of the myocardium, in accordance with another preferred embodiment of the present invention.

The device 550 includes an implantable lead or catheter like member 551. The lead 551 includes a probe electrode 552 attached to the distal end thereof. The lead 551 further includes a reference electrode 556 attached thereto. The attachment of the reference electrode 556 to the lead 551 is similar to the attachment of reference electrode 54 to the lead 50 of FIG. 5. The lead 551 further includes contact guards 58, and tines 56. The lead 551 further includes a resistive element 555 disposed within the probe electrode 552 for heating the probe electrode 552. The resistive element 555 may be a carbon cylinder resistor or a ceramic coated fine coiled MP32N wire of about 100Ω resistance. However, the resistive element 555 may also be any other suitable resistive element.

The resistive element 555 is electrically insulated from the probe electrode 552 and is thermally coupled to the probe electrode 552 by a thermally conducting paste (not shown) or a thermally conducting glue (not shown) or by any other suitable means for thermal coupling. The resistive element 555 is electrically connected to a current source 558 and to a temperature control unit 560 by a pair of electrically insulated electrically conducting wires 562 and 564. The current source 558 heats the resistive element 555 by controllably flowing an electrical current therethrough. The current may be a continuous current or pulses of current having a fixed or variable duration and frequency. The temperature control unit 560 is connected to the current source 558 and controls the currents flowing through the resistive element 555 by controlling the current source 558. Preferably, the temperature control unit 560 determines the temperature of the resistive element 555 by determining the change of resistance value as current is passed through the resistive element 555. Methods and devices of determining the temperature of a resistor from it's resistance are well known in the art and will not be discussed in detail.

The device 550 further includes an amplifier 568 for amplifying the potential difference between the probe electrode 552 and the reference electrode 556. The probe electrode 552 is connected to one input terminal of the amplifier 568 by an electrically insulated electrically conducting wire 563. The reference electrode 556 is electrically connected to the other input terminal of the amplifier 568 through the electrically insulated electrically conducting wire 562.

It is noted that, while the design of the device 550 of FIG. 28 is a preferred design for minimizing the number of wires required within the lead 551, other alternative designs may be used for the device 550. For example, the temperature sensing may be performed by a thermistor (not shown) thermally coupled to the probe electrode and electrically connected to the temperature control unit 560.

After implantation of the lead 551, MAP signals will gradually disappear and/or distort as electrode encapsulation and cell decoupling occur as disclosed hereinabove. When MAP signal recording is desired, an electrical current is passed through the resistive element 555 at the distal MAP sensing electrode. This current causes the resistive element 555 to heat the probe electrode 552 which will heat the underlying tissue, causing injury-like currents to appear, thus enabling long-term chronic MAP recordings. In operation, the temperature of the probe electrode 562 is slowly increased by the temperature control unit 560 to a value at which the recorded signals change in morphology from IEGM-like signals to stable MAP-like signals. The temperature of the probe electrode 552 would then be maintained at this value for the desired duration of the recording.

The temperature control unit 560 ensures that the current applied to the resistive element 555 is of a value suitable for the application. Electrode temperatures in the range of 42° to 48° C., if applied for only a few minutes per day, are suitable for producing injury like currents suitable for enabling MAP recording without causing permanent damage to the tissue.

It is noted that, thermal induction of depolarization in myocardial tissue can be achieved in other ways. For example, tissue temperature elevation can be achieved by passing a high-frequently current at sufficient current density to directly heat the tissue for causing thermally-induced depolarization.

Figure 29:
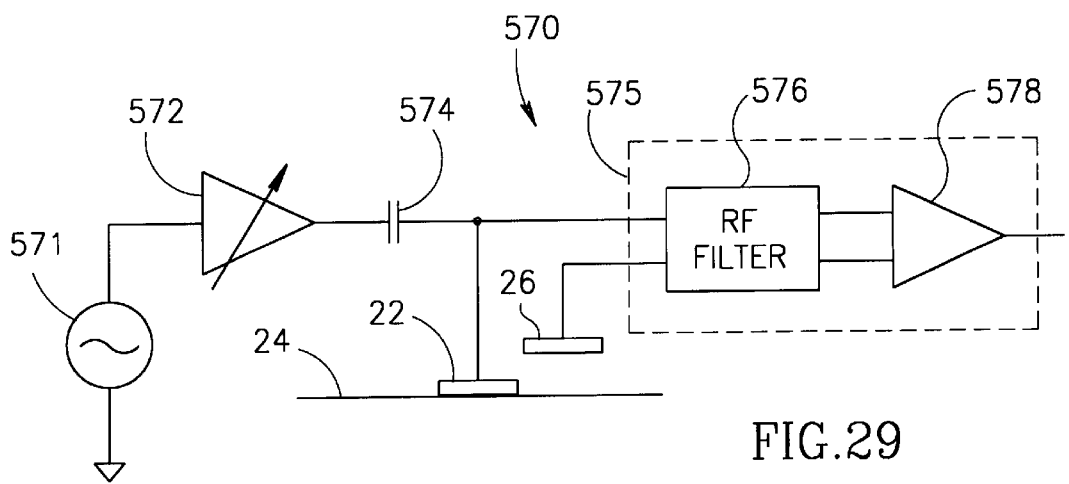
FIG. 29 is a schematic diagram of a device for chronic MAP recording using radio frequency (RF) induced heating of the myocardium, in accordance with a preferred embodiment of the present invention.

Reference is now made to FIG. 29 which is a schematic diagram of a device 570 for chronic MAP recording using radio frequency (RF) induced heating of the myocardium, in accordance with a preferred embodiment of the present invention. The device 570 includes an RF oscillator 571 for generating an radio frequency signal. The device 570 also includes a variable gain RF amplifier 572 connected to The RF oscillator 571 for controlling the amplitude of the RF signal. The device 570 also includes a probe electrode 22 connected to the RF amplifier 572 through a coupling capacitor 574. The probe electrode 22 is shown in contact with the cardiac muscle tissue 24. The device 570 also includes a reference electrode 26. The probe electrode 22 and the reference electrode 26 are included in a lead or catheter (not shown) such as the implantable lead 50 of FIG. 5 or in any other suitable implantable lead or catheter. The device 570 also includes a signal amplification unit 575 connected to the probe electrode 22 and to the reference electrode 26. The signal amplification unit 575 includes an RF filter 576 and an amplifier 578 connected to the RF filter 576. The RF filter 576 filters the RF signal component of the RF amplifier 572 from the signal sensed by the probe electrode 22 prior to amplification of the sensed signal by the amplifier 578. The coupling capacitor 574 prevents DC signals developed at the output of the RF amplifier 572 from reaching the tissue 24 and the RF filter 576 of the signal amplification unit 575.

It is noted that, the device 570 of FIG. 29 does not require any means to heat the probe electrode 22 such as the resistor 555 of FIG. 27, since heating is caused directly at the tissue's cellular level. The radio frequency used by the device 570 is approximately 100 KHz. However, other suitable high frequencies in the range of 10–1200 KHz may be used. The use of high frequency electromagnetic energy for heating, cauterization and ablation of tissue is known in the art. For example, U.S. Pat. No. 5,398,683 to Edwards et al. discloses a system using a combination catheter for recording MAPs by the contact method and for ablating tissue by providing electromagnetic energy thereto. The design of the signal amplification unit 575 of FIG. 29 is known in the art. For example, a design similar to the design illustrated in FIG. 7 of U.S. Pat. No. 5,398,683 to Edwards et al. may be used in implementing the signal amplification unit 575 of FIG. 29.

In operation, the lead (not shown) including the probe electrode 22 and the reference electrode 26 is implanted in the heart of a patient. After implantation, MAP signals will gradually disappear and/or distort as electrode encapsulation and cell decoupling occur as disclosed hereinabove. When MAP signal recording is desired, the recording of IEGM-like signals is initiated while electromagnetic energy is applied to the probe electrode 22 for gradually heating the tissue under the probe electrode 22. The heating is controlled by continuously applying RF frequency currents to the tissue through the probe electrode 22 and gradually increasing the amplitude of the RF currents applied to the tissue until the recorded IGEM-like signals change into MAP-like signals. A stable recording of MAP-like signals may be achieved by maintaining the RF currents' amplitude at a level sufficient for record acceptable MAPs for the required time period. The application of RF currents to the tissue is terminated after the recording session is finished.

It is noted that, while the device 570 uses RF electromagnetic energy for heating the cardiac tissue, other frequencies of electromagnetic radiation may also be used for tissue heating in additional embodiments of the present invention. For example, microwaves at the frequency range of 0.7–100.0 GHz may be used with appropriate adaptations to the design of the appropriate electrical circuits of the device 570. Such adaptations include replacing the RF oscillator, the variable gain RF amplifier 572 and the coupling capacitor 574 of FIG. 29 by a suitable source of microwave radiation (not shown). Additionally, this source of microwave radiation is coupled to the portion of tissue 24 by a suitable wave-guide (not shown) placed near the probe electrode 22. The wave-guide may be an elongated wave-guide positioned within a catheter like device (not shown). One end of the wave-guide (not shown) may be disposed within a hole or suitable passage (not shown) passing within the probe electrode 22, through which it can be coupled to the cardiac muscle tissue 24. It is further noted that the heating of the tissue by microwave radiation is due to vibrational absorption of energy by various molecular components comprising the cardiac tissue.

Figure 30:
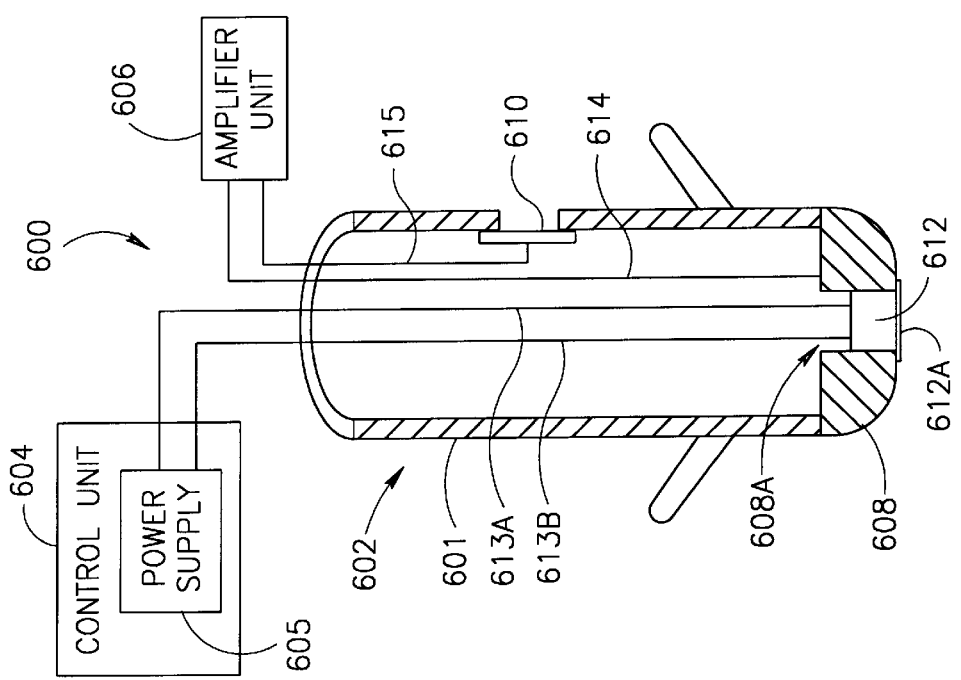
FIG. 30 is a schematic diagram of a device for chronic MAP recording using light induced heating of the myocardium, in accordance with another preferred embodiment of the present invention.

Reference is now made to FIG. 30 which is a schematic diagram of a device 600 for chronic MAP recording using light induced heating of the myocardium, in accordance with another preferred embodiment of the present invention. The device 600 includes a lead 602, a control unit 604 and an amplifier unit 606. The lead 602 includes a housing 601. A probe electrode 608 is attached to the distal end of the housing 601. The lead 602 further includes a reference electrode 610 attached to the housing 601.

The arrangement of the probe electrode 608 and the reference electrode 610 is similar to the arrangement of the probe electrode 132 and the reference electrode 133 of the lead 140 of FIG. 11 and are suitable for MAP recording. The probe electrode 608 has a hole 608A passing therethrough. A light emitting diode (LED) 612 is disposed within the hole 608A and sealingly attached to the probe electrode 608. An optical window 612A is attached to the LED 612 for protecting the surface of the LED 612. The LED 612 is electrically connected to a power supply 605 included within the control unit 604 by insulated electrical conducting wires 613A and 613B. The probe electrode 608 and the reference electrode 610 are connected to the amplifier unit 606 by electrically insulated electrically conducting wires 614 and 615, respectively. The amplifier unit 606 may be any amplifier capable of amplifying MAP signals such as the amplifier 28 of FIG. 3, or any other suitable type of amplifier.

After the lead 602 is implanted and the probe electrode 608 is placed in contact with the myocardial tissue, the LED 612 may be used for heating the region of the myocardium under the optical window 612A. The LED 612 may be an infra-red light emitting diode capable of emitting infra-red light at a wavelength and intensity which are sufficient for heating a region of myocardium under the LED 612 to a temperature sufficient for inducing localized depolarization and injury-like currents in this underlying region of myocardium. The optical window 612A is transparent to the wavelengths of light emitted by the LED 612.

When MAP signal recording is desired, the recording of IEGM-like signals by the amplifier unit 606 is initiated and pulsed or continuous infrared light is applied to the myocardium underlying the LED 612 for gradually heating the tissue under the probe electrode 22. The heating is controlled to gradually increase the temperature of the tissue underlying the LED 612 until the recorded IGEM-like signals change into MAP-like signals. A stable recording of MAP-like signals may be achieved by maintaining the heating rate at a level sufficient for recording acceptable MAPs for the required time period. The heating of the tissue is terminated after the recording session is finished by switching off the supply of power from the power supply 605 to the LED 612. The control of heating is achieved by controlling the light intensity of the continuous or pulsed light applied to the tissue by the LED 612 or by using pulsed light of a constant light intensity level and varying the duration and/or frequency of the light pulses delivered to the tissue.

The LED 612 of FIG. 30 is operated by electrical current withdrawn from the power supply 605. The power supply 605 may be any suitable type of power supply. For example, the power supply 605 may be a battery which is included together with the control unit 604 within an implantable case (not shown), in which case the device of FIG. 30 becomes fully implantable. In such a device the case (not shown) may also include all the circuitry needed to operate the implantable device including control and telemetry circuits (not shown) similar to the circuits disclosed for the systems of FIGS. 20 and 22.

Figure 31:
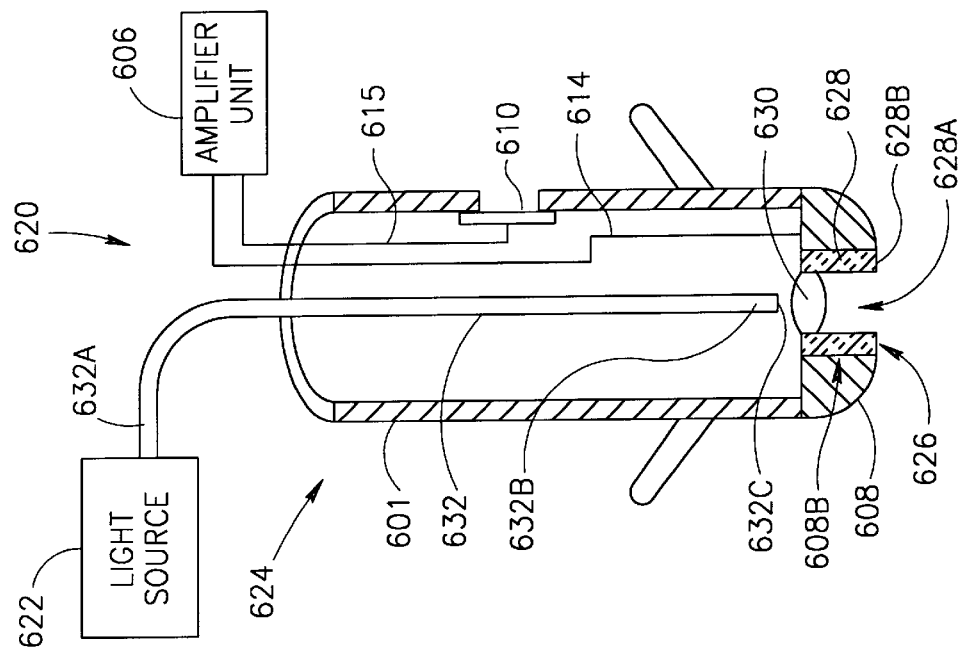
FIG. 31 is a schematic diagram of a device for chronic MAP recording using light induced heating of the myocardium, in accordance with another preferred embodiment of the present invention.

Reference is now made to FIG. 31 which is a schematic diagram of a device 620 for chronic MAP recording using light induced heating of the myocardium, in accordance with another preferred embodiment of the present invention. The device 620 includes a lead 624, a light source 622 and an amplifier unit 606. The lead 624 includes a housing 601. A probe electrode 608 is attached to the distal end of the housing 601. The lead 624 further includes a reference electrode 610 attached to the housing 601.

The arrangement of the probe electrode 608 and the reference electrode 610 is similar to the arrangement of the probe electrode 132 and the reference electrode 133 of the lead 140 of FIG. 11 and are suitable for MAP recording. The probe electrode 608 has a passage 608B passing therethrough. An optical coupler 626 is attached within the passage 608B. The optical coupler 626 includes a cylindrical tube 628 having a hollow passage 628A therein, and an optical element 630 attached to one end of the cylindrical tube 628. The device 620 further includes an optical fiber 232 optically coupled to the light source 622 at its distal end 632A. A part of the optical fiber 632 is disposed within the housing 601 of the lead 621. The proximal end 632B of the optical fiber 632 is optically coupled to the optical element 630. The optical element 630 may be a lens or a combination of a number of lenses (not shown) and/or other optical elements (not shown) suitable for directing the light from the optical fiber 632 towards the region of tissue (not shown) underlying the passage 628. Alternatively, the proximal end 632B of the optical fiber 632 may be directly and sealingly attached within the passage 628 obviating the need for the optical element 630. In this latter case (not shown), the surface 632C of the proximal end 632B of the optical fiber 632 is attached flush with the surface 628B of the cylindrical tube 628.

The probe electrode 608 and the reference electrode 610 are connected to the amplifier unit 606 by electrically insulated electrically conducting wires 614 and 615, respectively. The light source 622 is a controllable infra-red laser light source such as a infra-red laser diode, and the optical fiber 632 is an optical fiber capable of guiding infra-red light radiation.

The operation of the device 620 for MAP recording is similar to the operation of the device 600 of FIG. 30 and is based on controllably heating the myocardial tissue under the opening of the passage 628A by controlled activation of the light source 622. The light emitted by the light source 622 is guided by the optical fiber and directed by the optical element 630 to the surface of the myocardium where some of the light is absorbed and locally heats the myocardium to induce a depolarization and injury-like currents as disclosed hereinabove.

It is noted that, while the devices 600 and 620 include an infra-red LED and an infra-red diode laser, respectively, used as a light source for heating the myocardium, these infra-red light sources are given by way of example only and other types of light sources may also be used. For example, the light source 622 may be any light source emitting coherent or incoherent light radiation of a wavelength capable of being absorbed by myocardial tissue to cause sufficient heating thereof. The light source 622 may deliver continuous light radiation or pulsed light radiation in a controlled manner to the myocardium.

If the light source 622 is a small light source, for example a LED, the light source 622 may be placed within the housing (not shown) of an implantable case (not shown). Alternatively, the light source 622 may be placed outside the patient with the optical fiber 632 passing the skin of the patient to be coupled to the light source 622 only when MAP measurements need to be taken.

It will be appreciated that in accordance with additional preferred embodiment of the present invention, the devices 600 and 620 of FIGS. 30 and 31, respectively, may also be integrated, with appropriate modifications made thereto, within implantable pacemaker devices (not shown). Such pacemaker devices may be part of a system similar to the system 220 disclosed hereinabove and illustrated in FIG. 20, with appropriate modifications. For example, the electroporating unit 228 of the system 220 of FIG. 20 may be replaced by the control unit 604 of FIG. 30 and the lead 190 of system 220 may be replaced by the lead 604 of FIG. 30. If passage of an optical fiber through the skin is needed, the transcutaneous electrical access port 197 and the needle connector 198 of FIG. 20 may be suitably adapted for including two optically couplable optical fibers (not shown) instead of the single optical fiber 632 of FIG. 31.

It is noted that, an advantage of the above disclosed methods of thermal induction of depolarization is that tissue temperature can be maintained throughout the recording period by continuously heating the tissue to maintain stability of the recordings.

Light-induced Localized Myocardial Depolarization

Light has also been shown to cause non-thermal transitory changes in the level of excitable-tissue polarization. For example, in an article titled "EFFECT OF LIGHT ON CALCIUM TRANSPORT IN BULL SPERM CELLS", published by R. Lubart et al. in Journal of Photochemical Photobiology B, Vol 14, No. 4, pp. 337–341, 1992, incorporated herein by reference the authors report that laser light increases the calcium transport in bull sperm cells.

Therefore, in accordance with a preferred embodiment of the present invention, this property of light may be used to induce a non-thermal localized depolarization and injury-like currents at times when MAP recording is desired. For example, the devices 600 and 620 of FIGS. 30 and 31 may be adapted for the delivery of light pulses to the myocardium to induce non-thermal photic depolarization and injury-like currents by replacing the infra-red emitting LED 612 of FIG. 30 by a suitable LED or other small light source capable of producing light of a wavelength suitable for inducing non-thermal depolarization in the myocardium. Similarly, the light source 622 of FIG. 31 may be replaced by a suitable coherent or non-coherent light source such as a laser or a flash lamp, respectively, which produce light of a wavelength suitable for inducing non-thermal depolarization in the myocardium. Following such a replacement, the devices may be used to record MAPs by recording IEGM-like signals and irradiating the myocardium with light until MAP-like signals are stably recorded.

Induction of Localized Myocardial Depolarization by Ultrasound

Localized ultrasound application can cause sufficient localized myocardial depolarization to induce injury-like currents without causing permanent tissue damage and electrical uncoupling. For example, in an article titled "THE ACTION OF ULTRASOUND ON THE CONTRACTION STRENGTH AND ACTION POTENTIAL OF THE PAPILLARY MUSCLE OF THE RAT HEART" published by S. I. Zakharov et al. in Biull. Eksp. Biol. Med., vol 107, No. 4, pp. 423–426, 1989, incorporated herein by reference, the authors disclose that application of ultrasound at 0.88 MHz to rat papillary muscle produced a non-thermal depolarization of up to 20 millivolts.

Figure 32:
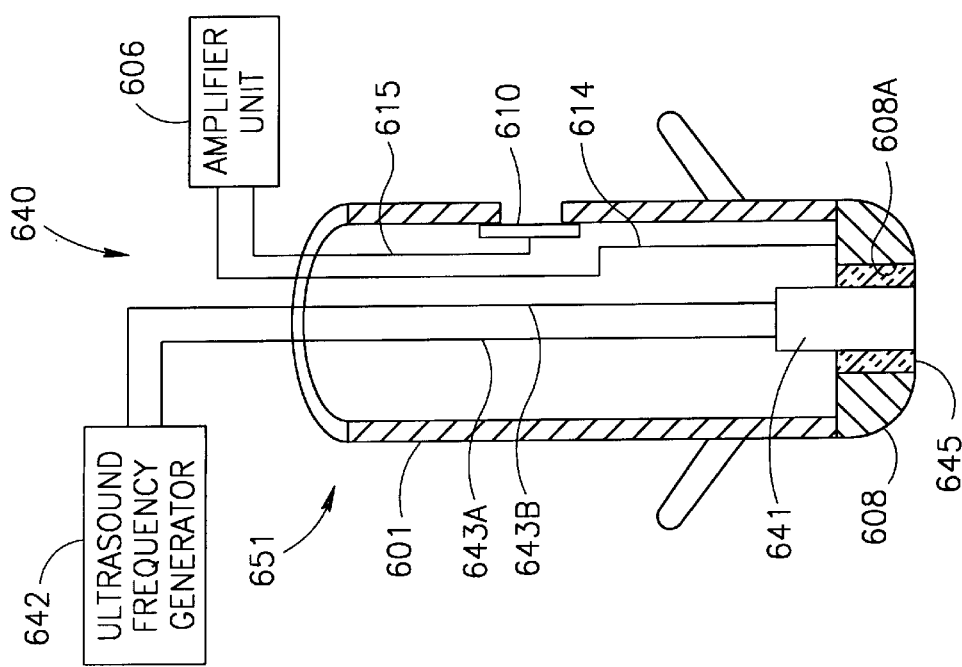
FIG. 32 is a schematic diagram of a device for chronic MAP recording using ultrasonically induced depolarization of the myocardium, in accordance with another preferred embodiment of the present invention.

Reference is now made to FIG. 32 which is a schematic diagram of a device 640 for chronic MAP recording using ultrasonically induced depolarization of the myocardium, in accordance with another preferred embodiment of the present invention. The device 640 includes an ultrasound frequency generator 642, an implantable lead 651 and an amplifier 606. The lead 651 includes a probe electrode 608 and a reference electrode 610 electrically connected to the amplifier 606 for MAP recording as disclosed in detail hereinabove. The probe electrode 608 has a passage 608A therewithin. The lead 651 also includes a cylindrical sleeve 645 attached within the passage 608A of the probe electrode 608. The lead 651 further includes an ultrasonic transducer 641 sealingly attached within the sleeve 645. The ultrasonic transducer 641 may include a small piezoelectric crystal (not shown) with the appropriate electrical contacts (not shown) connected to the ultrasonic frequency generator 642 by the electrically isolated electrically conducting wires 643A and 643B. The ultrasonic transducer 641 may be controllably energized by the ultrasound frequency generator 642 to generate ultrasonic radiation.

After implantation, MAP recording may be initiated by recording IEGM-like signals using the probe electrode 608 and the reference electrode 610 while ultasonically irradiating the myocardium underlying the ultrasonic transducer 641 using an irradiation intensity and duration sufficient to cause a local depolarization and injury-like currents in the myocardium region underlying the ultrasonic transducer 641. The IEGM-like signal turns into a MAP-like signal and MAPs may then be recorded. Sonic waves and ultrasonic waves in the range of approximately 30 KHz–5 MHz may be used at intensities which are clinically acceptable and would not cause significant myocardial damage. However, other sonic and ultrasonic frequencies outside of the above range may also be used provided that an appropriate intensity which is non-damaging to the tissue is used.

Induction of Localized Myocardial Depolarization by Chemical Means

Chemically depolarizing substances may also be used for inducing a localized transient depolarization and injury-like currents in myocardial tissue. The controlled release of such depolarizing substances from a chronically implanted catheter may be used for chronic recording of MAPs, in accordance with another preferred embodiment of the present invention.

It is well known in the art that certain substances may induce a depolarization of myocardial muscle cells. For example, application to a region of myocardium of a physiological solution including potassium chloride (KCl) in a concentration larger than about 4 millimolar induces a depolarization in the myocardial cells exposed to this solution. The amplitude of the KCl induced depolarization depends on the concentration of potassium ions in the applied solution. This depolarization may be reversed by removing the applied solution from the depolarized myocardial region by washing or by diffusion. If a small amount of such a KCL solution is locally applied from a hollow catheter-like device (not shown), the resulting depolarization and injury-like currents be used for MAP recording in a way similar to the methods disclosed hereinabove. Care must be taken to avoid excessive application of KCl amounts which may induce excessive myocardial depolarization which may lead to ventricular tachycardia and ventricular fibrillation.

Figure 33:
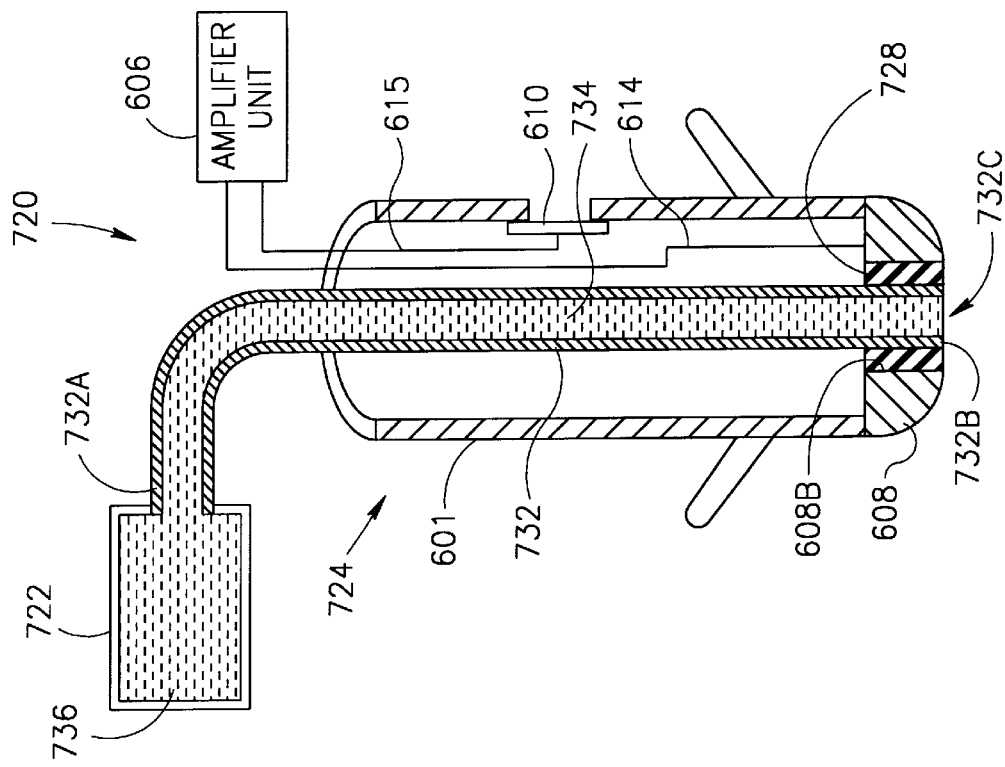
FIG. 33 is a schematic diagram of a device for chronic MAP recording using chemically induced depolarization of the myocardium, in accordance with another preferred embodiment of the present invention.

Reference is now made to FIG. 33 which is a schematic diagram of a device 720 for chronic MAP recording using chemically induced local myocardial depolarization, in accordance with a preferred embodiment of the present invention.

The device 720 includes a fluid reservoir 722, a catheter 724 and an amplifier unit 606. The reservoir 722 may be an external reservoir which is not implanted in the patient or may be an implantable reservoir included within a housing or a case (not shown) of an implantable device. The catheter 724 includes a housing 601, a probe electrode 608 and a reference electrode 610. The probe electrode 608 and the reference electrode 610 are connected to the amplifier unit 606 as disclosed in detail hereinabove, and may be used for bipolar MAP recording as disclosed in detail hereinabove.

The catheter 724 further includes a flexible hollow tube-like member 732 having a hollow lumen 734 therein. The distal end 732A of the tube-like member 732 is connected to the fluid reservoir 722. The proximal end 732B of the tube-like member 732 is sealingly attached to a cylindrical gasket 728 within is sealingly attached to a hollow passage 608B passing through the probe electrode 608. The lumen 734 of the tube-like member 732 is filled with a solution 736 which is contained within the reservoir 722. The proximal end 732B of the tube-like member 732 has an opening 732C therein. When the device 720 is chronically implanted within a heart, the solution 736 may be applied to the myocardial tissue (not shown) adjacent the opening 732C by controllably pushing or pumping a small amount of the solution 736 through the opening 732C using a suitable fluid pump (not shown).

The application of the solution 736 may also be done by other methods such as controlled diffusion through a closable valve-like device (not shown) attached at the proximal end 732B of the tube-like member 732, by iontophoresis, or by other suitable methods. The solution 736 may be a physiological solution containing KCl at a concentration sufficient to induce a myocardial cell depolarization of approximately 20 millivolts. The solution 736 may also be a physiological solution containing another substance or substances capable of inducing a localized reversible non-toxic myocardial cell depolarization. For example, small amounts of natural or artificial ionophores or substances capable of forming ionic channels within membranes may be used provided that their depolarizing effects may be reversed.

In operation, the recording of IGEM-like signals is initiated and a small amount of the solution 736 is applied to the myocardium subjacent the probe electrode 608. The myocardial depolarization will caused the IEGM-like signal to gradually turn into MAP-like signals which may be then recorded. Stopping the application of the solution 736 to the tissue will restore the tissue to it's former non-depolarized state by removing the KCl or other depolarizing substance by the blood perfusing the myocardium.

It is noted that, while in the preferred embodiment disclosed hereinabove the depolarizing substance is KCl, a combination of depolarizing substances may also be used. For example, the solution in the reservoir 722 may be a physiological solution including KCl at a myocardial depolarizing concentration and another depolarizing substance such as an ionophore or ionic channel former compound.

It is noted that, although some of the devices disclosed hereinabove are designed solely for recording measuring and monitoring MAP signals, all the methods disclosed hereinabove for chronic MAP recording may be used for constructing MAP recording devices which are incorporated as part of an implantable pacemaker, a defibrillator, a drug delivery system and an excitable tissue controller. Such integrated devices are believed to be within the scope of the present invention.

For example, devices for chronically recording MAPs, in accordance with preferred embodiments of the present invention, may be used for MAP recording in devices for the control of excitable tissue, such as the excitable tissue controllers disclosed in PCT applications, International Publication Numbers WO 97/25098, WO 98/10828 and WO 98/10829 to Ben-Haim et al., incorporated herein by reference.

The devices for chronically recording MAPs, in accordance with preferred embodiments of the present invention, or certain parts thereof may also be integrated as MAP recording devices in pacemaker devices such as the pacemaker device disclosed in International Publication No. WO 98/10832 to Ben Haim et al., or in other pacemaker devices known in the art.

The devices for chronically recording MAPs, in accordance with preferred embodiments of the present invention, or certain parts thereof may also be integrated as devices for MAP recording in drug delivery systems such as the drug delivery system disclosed in U.S. Pat. No. 5,556,421 to Prutchi et al. or in other drug delivery devices and systems known in the art, wherein the devices may be used for monitoring various MAP parameters to monitor drug effects and/or to control drug delivery. Such MAP sensing drug delivery devices include external non-automatic, semiautomatic and fully automatic drug delivery systems and implantable drug delivery systems.

The devices for chronically recording MAPs, in accordance with preferred embodiments of the present invention, may also be used as event sensors for defibrillator devices such as the defibrillator device disclosed in U.S. Pat. No. 5,531,764 to Adams et al., or other defibrillator devices known in the art. The chronic MAP recording devices of the present invention may be particularly advantageous when integrated with defibrillators for distinguishing between ventricular tachycardia (VT) and ventricular fibrillation (VF). This advantage stems from the fact that, in contrast to the commonly used ECG recordings, DC coupled MAP recordings are minimally affected by the currents used to induce tachyarrhythmia applied during the testing of an implantable defibrillator and by the defibrillator discharge currents used to terminate the tachyarrhythmia.

These methods and devices for chronic monitoring of MAPs may enable expanding these applications to the chronic assessment of the progression of cardiomyopathy and heart transplant rejection, precise titration of pharmaceutical myocardial therapies, and as a method for predicting life-threatening arrhythmic events.

It will be appreciated that, while the present invention is particularly adapted to the chronic measuring of cardiac MAPs in-situ, the invention may also be applied to the chronic measuring of MAPs in other excitable tissues such as nerve tissue, smooth muscle tissue including uterine muscle, bladder muscle, intestinal muscle, and other excitable tissue types.

It is noted that, while some the preferred embodiments of the MAP recording methods and devices of the present invention are adapted for chronic MAP recording using chronic cardiac device implantation, other preferred embodiments of the present invention may be adapted for non-chronic MAP recording using insertable MAP recording devices. Such devices may be simpler to operate in comparison to the contact electrode method known in the art since less stringent electrode positioning and tissue contact are required by the methods and devices of the present invention.

It is further noted that while the preferred embodiments of FIGS. 23 and 28–33, of the present invention disclosed hereinabove are particularly adapted for endocardial use, other embodiments may be adapted for epicardial use, mid-myocardial use and for any combination of endocardial, epicardial and mid-myocardial recording by suitably modifying the structure of the implantable catheter or lead used for MAP recording. For example, the implantable lead 651 of FIG. 32 may be modified by shaping it in a form suitable for mid-myocardial insertion (not shown) and by including a plurality of spatially separated probe electrodes along the lead's insertable part and a plurality of ultrasonic transducers (not shown), similar to the ultrasonic transducer 641, each of the ultrasonic transducers is disposed proximate one of the plurality of probe electrodes. Similar such arrangements are possible for other preferred embodiments of the invention and are included within the scope of the present invention.

While the invention has been described with respect to a limited number of embodiments, it will be appreciated that many variations, modifications and other applications of the invention may be made which are within the scope and spirit of the invention.

What is claimed is:

1. A method for measurement of monophasic action potentials from an excitable tissue including a plurality of cells, the method comprising the steps of:
   providing at least one sensing electrode adjacent to or in contact with a portion of said excitable tissue and at least one reference electrode in proximity to said at least one sensing electrode;
   intermittently inducing a transient depolarization in at least some of said cells adjacent said sensing electrode, said depolarization lasting for a first time interval; and
   measuring a signal representing the potential difference between said sensing electrode and said reference electrode within at least part of said first time interval.

2. The method according to claim 1 wherein said excitable tissue is cardiac muscle of an in-vivo heart of a patient and said plurality of cells includes cardiac muscle cells.

3. The method according to claim 2 wherein said cardiac muscle is selected from endocardial muscle, epicardial muscle, mid-myocardial muscle and any combination thereof.

4. The method according to claim 1 wherein said step of intermittently inducing comprises applying an electrical current pulse through said at least one sensing electrode and said at least one reference electrode to said at least some of said cells, said current pulse having a pulse duration, pulse shape, pulse magnitude and pulse polarity sufficient for causing electroporation of cell membranes of said at least some of said cells.

5. The method according to claim 1 further including, prior to said step of intermittently inducing, the step of providing at least one electroporating electrode in contact with at least a portion of said excitable tissue adjacent to said sensing electrode, wherein said step of intermittently inducing comprises intermittently applying a current pulse through said at least one electroporating electrode and said at least one reference electrode to said at least some of said cells, said current pulse having a pulse duration, pulse shape, pulse magnitude and pulse polarity sufficient for causing electroporation of cell membranes of said at least some of said cells.

6. The method according to claim 1 wherein said step of intermittently inducing comprises the step of intermittently increasing the temperature of at least part of said portion of said excitable tissue adjacent to or in contact with said at least one sensing electrode to a temperature value sufficient to produce a depolarization and injury-like currents in said at least part of said portion.

7. The method according to claim 6 wherein said temperature value is in the range of 42°–48° C.

8. The method according to claim 7 wherein said step of intermittently increasing the temperature further includes the step of determining the temperature of said resistive element by measuring the resistance of said resistive element.

9. The method according to claim 6 wherein said step of intermittently increasing the temperature comprises the step of controllably heating said at least one sensing electrode by controllably passing an electrical current through a resistive element thermally coupled to said at least one sensing electrode.

10. The method according to claim 6 wherein said step of intermittently increasing the temperature comprises the step of controllably heating said portion of said excitable tissue by controllably passing a high frequency alternating current therethrough.

11. The method according to claim 10 wherein said high frequency alternating current is applied to said portion of said excitable tissue by said at least one sensing electrode and wherein said method further includes prior to said step of measuring the step of filtering said signal for removing high frequency signal components from said signal.

12. The method according to claim 10 wherein said high frequency alternating current is a radio frequency alternating current having a frequency in the range of 10–1200 KHz.

13. The method according to claim 6 wherein said step of intermittently increasing the temperature comprises the step of controllably heating at least part of said portion of excitable tissue by controllably irradiating at least part of said portion with microwaves having a frequency in the range of 0.7–100 GHz.

14. The method according to claim 6 wherein said step of intermittently increasing the temperature comprises the step of controllably irradiating at least part of said portion of said excitable tissue with light to heat said portion.

15. The method according to claim 14 wherein said light is infra-red light.

16. The method according to claim 1 wherein said step of intermittently inducing comprises the step of intermittently applying to at least part of said portion of said excitable tissue adjacent to or in contact with said at least one sensing electrode mechanical waves having a frequency and intensity suitable for inducing a localized depolarization in at least some cells of said excitable tissue.

17. The method according to claim 16 wherein said mechanical waves are selected from sonic waves and ultrasonic waves.

18. The method according to claim 16 wherein said excitable tissue is cardiac muscle of an in-vivo heart of a patient and said plurality of cells includes cardiac muscle cells.

19. The method according to claim 18 wherein said cardiac muscle is selected from endocardial muscle, epicardial muscle, mid-myocardial muscle and any combination thereof.

20. The method according to claim 1 wherein said step of intermittently inducing comprises the step of intermittently irradiating at least part of said portion of said excitable tissue adjacent to or in contact with said at least one sensing electrode with light having a frequency and intensity suitable for inducing a non-thermal localized depolarization in at least some cells of said excitable tissue.

21. The method according to claim 1 wherein said step of intermittently inducing comprises the step of intermittently applying to at least part of said portion of said excitable tissue adjacent to or in contact with said at least one sensing electrode at least one substance capable of inducing a depolarization in at least some of the cells of said excitable tissue.

22. The method according to claim 21 wherein said excitable tissue is cardiac muscle of an in-vivo heart of a patient and said plurality of cells includes cardiac muscle cells.

23. The method according to claim 22 wherein said cardiac muscle is selected from endocardial muscle, epicardial muscle, mid-myocardial muscle and any combination thereof.

24. The method according to claim 21 wherein said substance is a physiological solution including KCl at a concentration sufficient to cause a depolarization of 5–20 millivolts in myocardial cells in situ.

25. A method for measurement of a signal representing monophasic action potentials of an excitable tissue including a plurality of cells, the method comprising the steps of:
   providing a sensing electrode adjacent to or in contact with a portion of said excitable tissue and a reference electrode in proximity to said sensing electrode;
   intermittently inducing a transient depolarization and injury-like currents in at least some of said cells of said excitable tissue adjacent said sensing electrode by clamping the potential difference between said sensing electrode and said reference electrode at a value sufficient to electrostatically modify the electrical charge distribution across at least portions of the membranes of said at least some of said cells, said clamping lasting for a first time interval; and
   measuring the clamping current required to maintain said value of said potential difference within at least part of said first time interval to obtain said signal.

26. The method according to claim 25 wherein said excitable tissue is cardiac muscle of an in-vivo heart of a patient and said plurality of cells includes cardiac muscle cells.

27. The method according to claim 26 wherein said cardiac muscle is selected from endocardial muscle, epicardial muscle, mid-myocardial muscle and any combination thereof.

28. A method for measurement of signals representing monophasic action potentials from an excitable tissue including a plurality of cells, the method comprising the steps of:
   providing at least one sensing electrode adjacent to or in contact with a portion of said excitable tissue and at least one reference electrode in proximity to said sensing electrode;
   intermittently inducing a depolarization and injury-like currents in at least some of said cells of said excitable tissue adjacent said at least one sensing electrode by clamping the potential difference between said at least one sensing electrode and said at least one reference electrode at a value sufficient to electrostatically modify the electrical charge distribution across at least portions of the membranes of said at least some of said cells, said clamping lasting for a first time interval; and
   measuring the clamping current required to maintain said value of said potential difference within at least part of said first time interval to obtain at least one of said signals.

29. The method according to claim 28 wherein said excitable tissue is cardiac muscle of an in-vivo heart of a patient and said plurality of cells includes cardiac muscle cells.

30. The method according to claim 29 wherein said cardiac muscle is selected from endocardial muscle, epicardial muscle, mid-myocardial muscle and any combination thereof.

31. A method for measurement of signals representing monophasic action potentials from an excitable tissue, the method comprising the steps of:
   providing at least one sensing electrode adjacent to or in contact with a portion of said excitable tissue and at least one reference electrode in proximity to said at least one sensing electrode;
   clamping the potential difference between said at least one sensing electrode and said at least one reference electrode at a first value;
   measuring the clamping current required to maintain said first value of said potential difference to obtain biphasic or polyphasic signals representing biphasic or polyphasic action potentials in said excitable tissue;
   increasing said potential difference to a second value sufficient to obtain substantially monophasic signals representing said monophasic action potentials;
   maintaining said second value for a time interval sufficient for measuring at least one of said substantially monophasic signals; and
   measuring the clamping current required to maintain said second value of said potential difference to obtain at least one of said substantially monophasic signals.

32. The method according to claim 31 wherein said excitable tissue is cardiac muscle of an in-vivo heart of a patient and said plurality of cells includes cardiac muscle cells.

33. The method according to claim 32 wherein said cardiac muscle is selected from endocardial muscle, epicardial muscle, mid-myocardial muscle and any combination thereof.

34. The method according to claim 31 wherein said step of increasing comprises gradually increasing said potential difference to a second value sufficient to obtain substantially monophasic signals representing said monophasic action potentials.

35. Apparatus for measurement of monophasic action potentials from an excitable tissue including a plurality of cells, the apparatus comprising:
   at least one probe electrode placeable adjacent to or in contact with a portion of said excitable tissue;
   at least one reference electrode placeable proximate said at least one probe electrode;
   an electroporating unit electrically connected to said at least one probe electrode and said at least one reference electrode for controllably applying to at least some of said cells subjacent said at least one probe electrode electrical current pulses suitable for causing electroporation of cell membranes of said at least some of said cells; and
   an amplifier unit electrically connected to said at least one probe electrode and to said at least one reference electrode for providing an output signal representing the potential difference between said probe electrode and said reference electrode.

36. The apparatus according to claim 35 wherein said excitable tissue is an in-vivo heart, said cells are cardiac muscle cells and said monophasic action potentials are cardiac monophasic action potentials.

37. The apparatus according to claim 36 wherein said cardiac muscle cells are selected from endocardial muscle cells, epicardial muscle cells, mid-myocardial muscle cells and any combination thereof.

38. The apparatus according to claim 37 further including an analog to digital converter for digitizing the output signal of said amplifier to provide a digitized signal and a processing unit connected to said analog to digital converter and to said electroporating unit for controlling the activation of said electroporating unit and for processing said digitized signal to provide data representing at least one of said monophasic action potentials.

39. The apparatus according to claim 38 further including a telemetry unit in communication with said processing unit for wirelessly transmitting said data.

40. The apparatus according to claim 39 wherein said telemetry unit is capable of wirelessly receiving signals for externally controlling said apparatus.

41. The apparatus according to claim 39 wherein said telemetry unit is capable of wirelessly receiving signals for reprogramming said processing unit.

42. The apparatus according to claim 35 wherein said at least one probe electrode and said at least one reference electrode are disposed within an implantable lead or catheter-like device disposed within a cardiac chamber.

43. The apparatus according to claim 35 further including a sensing unit electrically connected to said at least one probe electrode and to said at least one reference electrode for receiving the output signal of said amplifier and for generating a trigger signal representing the detection of a monophasic action potential in said output signal.

44. The apparatus according to claim 35 wherein said excitable tissue is myocardial tissue of a heart and wherein said apparatus further includes a pacing device electrically connected to said at least one probe electrode for in-vivo pacing of said heart.

45. Apparatus for measurement of monophasic action potentials from an excitable tissue including a plurality of cells, the apparatus comprising:
   at least one sensing electrode placeable adjacent to or in contact with a portion of said excitable tissue for sensing the potential of said portion;
   at least one reference electrode placeable proximate said at least one sensing electrode for sensing a reference potential;
   at least one electroporating electrode adjacent to said sensing electrode, said at least one electroporating electrode is placeable adjacent said portion of said excitable tissue or in contact with a part thereof; and
   an electroporating unit electrically connected to said at least one electroporating electrode for controllably applying to at least some of said cells adjacent said at least one electroporating electrode electrical current pulses suitable for causing electroporation of cell membranes of said at least some of said cells.

46. The apparatus according to claim 45 wherein said excitable tissue is an in-vivo heart, said cells are cardiac muscle cells and said monophasic action potentials are cardiac monophasic action potentials.

47. The apparatus according to claim 46 wherein said cardiac muscle cells are selected from endocardial muscle cells, epicardial muscle cells, mid-myocardial muscle cells and any combination thereof.

48. Apparatus for measurement of monophasic action potentials from an excitable tissue including a plurality of cells, the apparatus comprising:
   a probe electrode placeable adjacent to or in contact with a portion of said excitable tissue;
   a reference electrode disposed proximate said probe electrode; and
   a voltage clamp unit electrically connected to said probe electrode and to said reference electrode for intermittently clamping the potential difference between said probe electrode and said reference electrode at a value sufficient to electrostatically modify the electrical charge distribution across at least portions of the membranes of said at least some of said cells to generate injury-like currents in at least some of said cells adjacent said probe electrode, and for providing a signal representing the clamping current required to maintain said value of said potential difference, said signal includes at least one of said monophasic action potentials.

49. The apparatus according to claim 48 wherein said excitable tissue is an in-vivo heart, said cells are cardiac muscle cells and said monophasic action potentials are cardiac monophasic action potentials.

50. The apparatus according to claim 49 wherein said cardiac muscle cells are selected from endocardial muscle cells, epicardial muscle cells, mid-myocardial muscle cells and any combination thereof.

51. The apparatus according to claim 48 further including a sensing unit electrically connected to said at least one probe electrode and to said at least one reference electrode for receiving the output signal of said voltage clamp unit and for generating a trigger signal representing the detection of a monophasic action potential in said output signal.

52. The apparatus according to claim 51 further including an analog to digital converter for digitizing the output signal of said voltage clamp unit to provide a digitized signal, and a processing unit connected to said analog to digital converter and to said voltage clamp unit for controlling the activation of said voltage clamp unit and for processing said digitized signal to provide data representing at least one of said monophasic action potentials.

53. The apparatus according to claim 52 further including a telemetry unit in communication with said processing unit for wirelessly transmitting said data.

54. The apparatus according to claim 53 wherein said telemetry unit is capable of wirelessly receiving signals for externally controlling said apparatus.

55. The apparatus according to claim 53 wherein said telemetry unit is capable of wirelessly receiving signals for reprogramming said processing unit.

56. The apparatus according to claim 48 wherein said at least one probe electrode and said at least one reference electrode are disposed within an implantable lead or catheter-like device disposed within a cardiac chamber.

57. The apparatus according to claim 48 wherein said excitable tissue is the myocardium of a heart and wherein said apparatus further includes a pacing device electrically connected to said at least one probe electrode for in-vivo pacing of said heart.

58. Apparatus for measurement of monophasic action potentials from an excitable tissue including a plurality of cells, the apparatus comprising:
   at least one probe electrode placeable adjacent to or in contact with a portion of said excitable tissue;
   at least one reference electrode disposed proximate said at least one probe electrode; and
   a voltage clamping unit electrically connected to said at least one probe electrode and to said at least one reference electrode for intermittently clamping the potential difference between said at least one probe electrode and said at least one reference electrode at a value sufficient to electrostatically modify the electrical charge distribution across at least portions of the membranes of said at least some of said cells to induce a transient depolarization in at least some of said cells adjacent said at least one probe electrode, and for providing a signal representing the clamping current required to maintain said value of said potential difference, said signal includes at least one of said monophasic action potentials.

59. Apparatus for measurement of monophasic action potentials from an excitable tissue including a plurality of cells, the apparatus comprising:

at least one sensing electrode placeable adjacent to or in contact with a portion of said excitable tissue;

at least one reference electrode disposed proximate said at least one probe electrode;

a controllable depolarizing unit for intermittently inducing a transient depolarization in at least some of said plurality of cells of said portion; and an amplifier unit electrically connected to said at least one sensing electrode and to said at least one reference electrode for providing an output signal representing the potential difference between said at least one probe electrode and said at least one reference electrode.

60. The apparatus according to claim 59 wherein said excitable tissue is an in-vivo heart, said cells are cardiac muscle cells and said monophasic action potentials are cardiac monophasic action potentials.

61. The apparatus according to claim 59 wherein said cardiac muscle cells are selected from endocardial muscle cells, epicardial muscle cells, mid-myocardial muscle cells and any combination thereof.

62. The apparatus according to claim 59 wherein said controllable depolarizing unit is a controllable heating device capable of controllably heating at least some of said plurality of cells of said portion to induce said transient depolarization.

63. The apparatus according to claim 62 wherein said heating device includes a resistive element thermally coupled to said at least one sensing electrode and a controllable current source electrically connected to said resistive element for controllably flowing electrical current through said resistive element to controllably heat said resistive element and said at least one sensing electrode.

64. The apparatus according to claim 63 wherein said heating device further includes a temperature control unit for determining the temperature of said resistive element by measuring the resistance of said resistive element and for controlling current flow through said resistive element based on said temperature.

65. The apparatus according to claim 63 wherein said heating device further includes a temperature sensor thermally coupled to said at least one sensing electrode, and a temperature control unit electrically connected to said temperature sensor, for determining the temperature of said at least one sensing electrode and for controlling current flow through said resistive element based on said temperature.

66. The apparatus according to claim 62 wherein said heating device includes a high frequency electromagnetic energy source coupled to said portion of said excitable tissue for heating said portion.

67. The apparatus according to claim 66 wherein said high frequency electromagnetic energy source includes a high frequency oscillator and a variable gain high frequency amplifier electrically connected to said oscillator, said high frequency amplifier is electrically coupled to said at least one sensing electrode by a capacitor for passing high frequency alternating electrical currents therethrough.

68. The apparatus according to claim 67 wherein said high frequency alternating electrical current is a radio frequency alternating current having a frequency in the range of 10–1200 KHz.

69. The apparatus according to claim 67 further including a high frequency filter electrically connected to said at least one sensing electrode, said at least one reference electrode and said amplifier unit for filtering out high frequency signal components generated by said high frequency amplifier.

70. The apparatus according to claim 66 wherein said high frequency electromagnetic energy source is a microwave energy source coupled to said excitable tissue by a waveguide and capable of producing microwave radiation having a frequency in the range of 0.7–100 GHz for controllably heating at least part of said portion.

71. The apparatus according to claim 62 wherein said heating device includes a controllable light source for controllably directing light onto at least part of said portion of said excitable tissue to heat said portion.

72. The apparatus according to claim 71 wherein at least some of the wavelengths of said light are absorbable by said portion to heat said portion.

73. The apparatus according to claim 72 wherein said light emitting diode is an infra-red light emitting diode.

74. The apparatus according to claim 71 wherein said light source includes a light emitting diode electrically connected to a control unit for controlling the emission of light by said light emitting diode.

75. The apparatus according to claim 71 wherein said light source is optically coupled to said portion by an optical fiber.

76. The apparatus according to claim 75 wherein said light source is selected from a coherent light source and an incoherent light source.

77. The apparatus according to claim 75 wherein said apparatus is an implantable apparatus and said light source is an implantable light source.

78. The apparatus according to claim 75 wherein said apparatus is implantable in a patient and wherein said light source is an external light source disposed out of said patient.

79. The apparatus according to claim 75 wherein said apparatus is implantable in a patient and wherein said light source is an internal light source disposed within the implantable apparatus.

80. The apparatus according to claim 75 wherein said optical fiber is optically coupled to said portion by at least one optical element.

81. The apparatus according to claim 59 wherein said controllable depolarizing unit comprises a source of mechanical waves.

82. The apparatus according to claim 81 wherein said source of mechanical waves is selected from a source of sonic waves and a source of ultrasonic waves.

83. The apparatus according to claim 81 wherein said source of mechanical waves includes an ultrasound frequency generator and an ultrasonic transducer electrically connected to said ultrasound frequency generator and mechanically coupled to said portion of said excitable tissue.

84. The apparatus according to claim 59 wherein said controllable depolarizing unit comprises a light source for controllably directing light onto at least part of said portion of said excitable tissue to induce a non-thermal localized depolarization in said portion.

85. The apparatus according to claim 84 wherein at least some of the wavelengths of said light are absorbable by said excitable tissue to induce a non-thermal depolarization in at least part of said portion.

86. The apparatus according to claim 84 wherein said light source includes a light emitting diode electrically connected to a control unit for controlling the emission of light by said light emitting diode.

87. The apparatus according to claim 84 wherein said light source is optically coupled to said portion by an optical fiber.

88. The apparatus according to claim 87 wherein said light source is selected from a coherent light source and an incoherent light source.

89. The apparatus according to claim 87 wherein said apparatus is an implantable apparatus and said light source is an implantable light source.

90. The apparatus according to claim 87 wherein said apparatus is implantable in a patient and wherein said light source is an external light source disposed out of said patient.

91. The apparatus according to claim 87 wherein said optical fiber is optically coupled to said portion by at least one optical element.

92. The apparatus according to claim 59 wherein said controllable depolarizing unit comprises a controlled release unit capable of releasing at least one substance capable of depolarizing said excitable tissue near at least part of said portion of said excitable tissue.

93. The apparatus according to claim 92 wherein said controlled release unit includes a reservoir for storing a fluid including said at least one substance and a hollow member having one end connected to said reservoir and a second end disposed near at least part of said portion for applying at least some of said fluid to said at least part of said portion.

94. The apparatus according to claim 93 wherein said controlled release unit further includes a controllable valve disposed at said second end of said hollow member for controlling the applying of said fluid from said second end.

95. The apparatus according to claim 93 wherein said controlled release unit further includes a controllable pump for assisting said applying of said fluid from said second end.

96. The apparatus according to claim 92 wherein said excitable tissue is an in-vivo heart, said cells are cardiac muscle cells and said monophasic action potentials are cardiac monophasic action potentials and wherein said fluid comprises a physiological solution including a concentration of potassium chloride suitable for inducing a depolarization in said portion, said depolarization being sufficient for recording at least one of said cardiac monophasic action potentials.

* * * * *